(12) United States Patent
Myung et al.

(10) Patent No.: US 10,752,768 B2
(45) Date of Patent: *Aug. 25, 2020

(54) ORTHOPEDIC IMPLANTS HAVING GRADIENT POLYMER ALLOYS

(71) Applicant: Hyalex Orthopaedics, Inc., Lexington, MA (US)

(72) Inventors: David Myung, Santa Clara, CA (US); Michael J. Jaasma, San Francisco, CA (US); Lampros Kourtis, Cambridge, MA (US); Curtis W. Frank, Cupertino, CA (US)

(73) Assignee: Hyalex Orthopaedics, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/811,997

(22) Filed: Mar. 6, 2020

(65) Prior Publication Data

US 2020/0239678 A1 Jul. 30, 2020

Related U.S. Application Data

(63) Continuation of application No. 16/579,375, filed on Sep. 23, 2019, which is a continuation of application
(Continued)

(51) Int. Cl.
*A61F 2/30* (2006.01)
*C08L 33/02* (2006.01)
(Continued)

(52) U.S. Cl.
CPC ............... *C08L 33/02* (2013.01); *A61F 2/30* (2013.01); *C08F 220/06* (2013.01);
(Continued)

(58) Field of Classification Search
CPC ............................................ A61F 2002/30004
See application file for complete search history.

(56) References Cited

U.S. PATENT DOCUMENTS 3,030,327 A  4/1962 Hosch
3,053,251 A  9/1962 Black et al.
(Continued)

FOREIGN PATENT DOCUMENTS

EP  0650707 A1  5/1995
EP  1779875 A1  5/2007
(Continued)

OTHER PUBLICATIONS

Balamurugan et al.; Development and spectral characterization of poly(methyl methacrylate)/hydroxyapatite composite for biomedical applications; Trenads Biomater. Artif. Organs; 18(1); pp. 41-45; Jul. 2004.
(Continued)

*Primary Examiner* — Michael F Pepitone
(74) *Attorney, Agent, or Firm* — Clark & Elbing LLP

(57) ABSTRACT

Orthopedic implants having a bone interface member and a water swellable IPN or semi-IPN with a stiffness, hydration, and/or composition gradient from one side to the other and physically attached to the bone interface member. The invention also includes an orthopedic implant system including an implant that may conform to a bone surface and a joint capsule. The invention also includes orthopedic implants with water swellable IPN or semi-IPNs including a hydrophobic thermoset or thermoplastic polymer first network and an ionic polymer second network, joint capsules, labral components, and bone interface members. The invention also includes a method of inserting an orthopedic implant having a metal portion and a flexible polymer portion into a joint, including inserting the implant in a joint in a first shape and changing the implant from a first shape to a second shape to conform to a shape of a bone.

19 Claims, 62 Drawing Sheets

Related U.S. Application Data

No. 15/394,297, filed on Dec. 29, 2016, now Pat. No. 10,457,803, which is a continuation of application No. 13/347,647, filed on Jan. 10, 2012, now abandoned, which is a continuation-in-part of application No. 13/219,348, filed on Aug. 26, 2011, now Pat. No. 8,883,915, which is a continuation-in-part of application No. 12/499,041, filed on Jul. 7, 2009, now abandoned.

(60) Provisional application No. 61/566,567, filed on Dec. 2, 2011, provisional application No. 61/383,705, filed on Sep. 16, 2010, provisional application No. 61/377,844, filed on Aug. 27, 2010, provisional application No. 61/166,194, filed on Apr. 2, 2009, provisional application No. 61/095,273, filed on Sep. 8, 2008, provisional application No. 61/079,060, filed on Jul. 8, 2008, provisional application No. 61/078,741, filed on Jul. 7, 2008, provisional application No. 61/454,957, filed on Mar. 21, 2011, provisional application No. 61/431,327, filed on Jan. 10, 2011.

(51) Int. Cl.

| | | |
|---|---|---|
| *C08G 18/83* | (2006.01) | |
| *C08G 18/44* | (2006.01) | |
| *C08F 236/06* | (2006.01) | |
| *C08F 220/14* | (2006.01) | |
| *C08F 220/06* | (2006.01) | |
| *C08G 18/48* | (2006.01) | |
| *C08G 18/76* | (2006.01) | |
| *C08L 75/16* | (2006.01) | |
| *C08L 75/06* | (2006.01) | |
| *C08G 77/38* | (2006.01) | |
| *C08L 75/04* | (2006.01) | |
| *A61F 2/42* | (2006.01) | |
| *A61F 2/44* | (2006.01) | |
| *A61F 2/40* | (2006.01) | |
| *A61F 2/38* | (2006.01) | |
| *A61F 2/32* | (2006.01) | |

(52) U.S. Cl.
CPC .......... *C08F 220/14* (2013.01); *C08F 236/06* (2013.01); *C08G 18/44* (2013.01); *C08G 18/4854* (2013.01); *C08G 18/7671* (2013.01); *C08G 18/831* (2013.01); *C08G 18/837* (2013.01); *C08G 77/38* (2013.01); *C08L 75/06* (2013.01); *C08L 75/16* (2013.01); *A61F 2/3099* (2013.01); *A61F 2/30988* (2013.01); *A61F 2/32* (2013.01); *A61F 2/3804* (2013.01); *A61F 2/3859* (2013.01); *A61F 2/3872* (2013.01); *A61F 2/3877* (2013.01); *A61F 2/4081* (2013.01); *A61F 2/4202* (2013.01); *A61F 2/4225* (2013.01); *A61F 2/4241* (2013.01); *A61F 2/4261* (2013.01); *A61F 2/442* (2013.01); *A61F 2002/30998* (2013.01); *A61F 2002/4205* (2013.01); *A61F 2002/4238* (2013.01); *A61F 2002/4256* (2013.01); *A61F 2310/00011* (2013.01); *A61F 2310/00179* (2013.01); *C08G 2270/00* (2013.01); *C08L 75/04* (2013.01); *C08L 2205/04* (2013.01)

(56) References Cited

U.S. PATENT DOCUMENTS

| | | |
|---|---|---|
| 3,702,611 A | 11/1972 | Fishbein |
| 3,826,678 A | 7/1974 | Hoffman et al. |
| 3,833,404 A | 9/1974 | Sperling et al. |
| 3,939,049 A | 2/1976 | Ratner et al. |
| 4,035,848 A | 7/1977 | Wagner |
| 4,128,600 A | 12/1978 | Skinner et al. |
| 4,192,827 A | 3/1980 | Mueller et al. |
| 4,224,699 A | 9/1980 | Weber |
| 4,302,553 A | 11/1981 | Frisch et al. |
| 4,312,079 A | 1/1982 | Dorre et al. |
| 4,320,709 A | 3/1982 | Hladun |
| 4,391,797 A | 7/1983 | Folkman et al. |
| 4,423,099 A | 12/1983 | Mueller et al. |
| 4,439,583 A | 3/1984 | Gould et al. |
| 4,452,925 A | 6/1984 | Kuzma et al. |
| 4,468,499 A | 8/1984 | Siegfried et al. |
| 4,477,604 A | 10/1984 | Oechsle, III |
| 4,487,865 A | 12/1984 | Balazs et al. |
| 4,500,676 A | 2/1985 | Balazs et al. |
| 4,502,161 A | 3/1985 | Wall |
| 4,536,554 A | 8/1985 | Lim et al. |
| 4,575,539 A | 3/1986 | DeCrosta et al. |
| 4,621,637 A | 11/1986 | Fishbein |
| 4,657,941 A | 4/1987 | Blackwell et al. |
| 4,678,468 A | 7/1987 | Hiroyoshi |
| 4,680,336 A | 7/1987 | Larsen et al. |
| 4,693,715 A | 9/1987 | Abel, Jr. |
| 4,693,721 A | 9/1987 | Ducheyne |
| 4,816,495 A | 3/1989 | Blackwell et al. |
| 4,836,884 A | 6/1989 | McAuslan |
| 4,846,841 A | 7/1989 | Oh |
| 4,865,601 A | 9/1989 | Caldwell et al. |
| 4,913,144 A | 4/1990 | Del Medico |
| 4,931,287 A | 6/1990 | Bae et al. |
| 4,966,934 A | 10/1990 | Huang et al. |
| 4,973,493 A | 11/1990 | Guire |
| 4,978,352 A | 12/1990 | Fedorov et al. |
| 5,030,230 A | 7/1991 | White |
| 5,061,270 A | 10/1991 | Aboczky |
| 5,067,961 A | 11/1991 | Kelman et al. |
| 5,087,392 A | 2/1992 | Burke et al. |
| 5,091,205 A | 2/1992 | Fan |
| 5,094,876 A | 3/1992 | Goldberg et al. |
| 5,100,689 A | 3/1992 | Goldberg et al. |
| 5,112,350 A | 5/1992 | Civerchia et al. |
| 5,115,056 A | 5/1992 | Mueller et al. |
| 5,122,133 A | 6/1992 | Evans |
| 5,133,769 A | 7/1992 | Wagner et al. |
| 5,171,318 A | 12/1992 | Gibson et al. |
| 5,258,024 A | 11/1993 | Chavel et al. |
| 5,264,495 A | 11/1993 | Irie et al. |
| 5,276,070 A | 1/1994 | Arroyo |
| 5,282,851 A | 2/1994 | Jacob-LaBarre |
| 5,290,548 A | 3/1994 | Goldberg et al. |
| 5,300,116 A | 4/1994 | Chirila et al. |
| 5,314,478 A | 5/1994 | Oka et al. |
| 5,374,515 A | 12/1994 | Parenteau et al. |
| 5,403,893 A | 4/1995 | Tanaka et al. |
| 5,476,515 A | 12/1995 | Kelman et al. |
| 5,554,665 A | 9/1996 | Tateosian et al. |
| 5,556,429 A | 9/1996 | Felt |
| 5,562,738 A | 10/1996 | Boyd et al. |
| 5,576,072 A | 11/1996 | Hostettler et al. |
| 5,587,406 A | 12/1996 | Yamamoto et al. |
| 5,589,563 A | 12/1996 | Ward et al. |
| 5,591,170 A | 1/1997 | Spievack et al. |
| 5,643,390 A | 7/1997 | Don et al. |
| 5,644,049 A | 7/1997 | Giusti et al. |
| 5,645,592 A | 7/1997 | Nicolais et al. |
| 5,656,210 A | 8/1997 | Hill et al. |
| 5,660,692 A | 8/1997 | Nesburn et al. |
| 5,674,942 A | 10/1997 | Hill et al. |
| 5,693,034 A | 12/1997 | Buscemi et al. |
| 5,716,633 A | 2/1998 | Civerchia |
| 5,733,289 A | 3/1998 | Seedhom et al. |
| 5,763,529 A | 6/1998 | Lucas |
| 5,770,669 A | 6/1998 | Robertson et al. |
| 5,800,412 A | 9/1998 | Zhang et al. |
| 5,824,079 A | 10/1998 | Siegler et al. |
| 5,834,532 A | 11/1998 | Yamamoto et al. |
| 5,836,313 A | 11/1998 | Perez et al. |

(56) References Cited

U.S. PATENT DOCUMENTS

| | | |
|---|---|---|
| 5,837,752 A | 11/1998 | Shastri et al. |
| 5,856,366 A | 1/1999 | Shiveley et al. |
| 5,904,927 A | 5/1999 | Amiji |
| 5,913,858 A | 6/1999 | Calandruccio et al. |
| 5,962,005 A | 10/1999 | Saga et al. |
| 5,976,648 A | 11/1999 | Li et al. |
| 6,001,894 A | 12/1999 | Ottersbach et al. |
| 6,005,160 A | 12/1999 | Hsiue et al. |
| 6,019,766 A | 2/2000 | Ling et al. |
| 6,027,742 A | 2/2000 | Lee et al. |
| 6,030,606 A | 2/2000 | Holmes |
| 6,031,017 A | 2/2000 | Waki et al. |
| 6,057,406 A | 5/2000 | Pojman et al. |
| 6,120,904 A | 9/2000 | Hostettler et al. |
| 6,160,084 A | 12/2000 | Langer et al. |
| 6,171,300 B1 | 1/2001 | Adams |
| 6,210,438 B1 | 4/2001 | Sheets, Jr. et al. |
| 6,214,044 B1 | 4/2001 | Silverstrini |
| 6,221,467 B1 | 4/2001 | Nazarova et al. |
| 6,224,893 B1 | 5/2001 | Langer et al. |
| 6,231,605 B1 | 5/2001 | Ku |
| 6,231,611 B1 | 5/2001 | Mosseri |
| 6,239,209 B1 | 5/2001 | Yang et al. |
| 6,251,965 B1 | 6/2001 | Wang et al. |
| 6,254,637 B1 | 7/2001 | Lee et al. |
| 6,264,695 B1 | 7/2001 | Stoy |
| 6,265,016 B1 | 7/2001 | Hostettler et al. |
| 6,281,271 B1 | 8/2001 | Rumphorst et al. |
| 6,306,177 B1 | 10/2001 | Felt et al. |
| 6,306,424 B1 | 10/2001 | Vyakarnam et al. |
| 6,331,578 B1 | 12/2001 | Turner et al. |
| 6,368,315 B1 | 4/2002 | Gillis et al. |
| 6,372,815 B1 | 4/2002 | Sulc et al. |
| 6,376,742 B1 | 4/2002 | Zdrahala et al. |
| 6,388,043 B1 | 5/2002 | Langer et al. |
| 6,391,055 B1 | 5/2002 | Ikada et al. |
| 6,428,576 B1 | 8/2002 | Haldimann |
| 6,429,256 B1 | 8/2002 | Vandevoorde et al. |
| 6,437,018 B1 | 8/2002 | Gertzman et al. |
| 6,440,444 B2 | 8/2002 | Boyce et al. |
| 6,479,565 B1 | 11/2002 | Stanley |
| 6,482,209 B1 | 11/2002 | Engh et al. |
| 6,494,917 B1 | 12/2002 | McKellop et al. |
| 6,509,098 B1 | 1/2003 | Merrill et al. |
| 6,585,771 B1 | 7/2003 | Buttermilch et al. |
| 6,610,067 B2 | 8/2003 | Tallarida et al. |
| 6,629,997 B2 | 10/2003 | Mansmann |
| 6,632,235 B2 | 10/2003 | Weikel et al. |
| 6,632,246 B1 | 10/2003 | Simon et al. |
| 6,645,715 B1 | 11/2003 | Griffith et al. |
| 6,652,587 B2 | 11/2003 | Felt et al. |
| 6,673,079 B1 | 1/2004 | Kane |
| 6,673,112 B2 | 1/2004 | Nigam |
| 6,679,917 B2 | 1/2004 | Ek |
| 6,689,165 B2 | 2/2004 | Jacob et al. |
| 6,726,322 B2 | 4/2004 | Andino et al. |
| 6,733,533 B1 | 5/2004 | Lozier |
| 6,740,087 B2 | 5/2004 | Knox |
| 6,755,865 B2 | 6/2004 | Tarabishy |
| 6,759,449 B2 | 7/2004 | Kimura et al. |
| 6,846,875 B2 | 1/2005 | Pennings et al. |
| 6,852,125 B2 | 2/2005 | Simon et al. |
| 6,866,936 B2 | 3/2005 | Opolski |
| 6,911,212 B2 | 6/2005 | Gertzman et al. |
| 6,918,914 B2 | 7/2005 | Bauer |
| 6,921,264 B2 | 7/2005 | Mayer et al. |
| 6,949,251 B2 | 9/2005 | Dalal et al. |
| RE38,839 E | 10/2005 | Magnante |
| 6,953,594 B2 | 10/2005 | Lee et al. |
| 6,955,540 B2 | 10/2005 | Mayer et al. |
| 6,960,617 B2 | 11/2005 | Omidian et al. |
| 6,976,997 B2 | 12/2005 | Noolandi et al. |
| 7,008,226 B2 | 3/2006 | Mayer et al. |
| 7,008,635 B1 | 3/2006 | Coury et al. |
| 7,018,460 B2 | 3/2006 | Xu et al. |
| 7,019,192 B2 | 3/2006 | Gertzman et al. |
| 7,029,479 B2 | 4/2006 | Tallarida et al. |
| 7,037,984 B2 | 5/2006 | Lendlein et al. |
| 7,049,351 B2 | 5/2006 | Phelan et al. |
| 7,066,958 B2 | 6/2006 | Ferree |
| 7,067,194 B2 | 6/2006 | Mao et al. |
| 7,083,650 B2 | 8/2006 | Moskowitz et al. |
| 7,094,286 B2 | 8/2006 | Liu |
| 7,105,026 B2 | 9/2006 | Johnson et al. |
| 7,160,305 B2 | 1/2007 | Schmieding |
| 7,163,541 B2 | 1/2007 | Ek |
| 7,176,247 B1 | 2/2007 | Walker, Jr. |
| 7,204,897 B2 | 4/2007 | Stoy et al. |
| 7,217,294 B2 | 5/2007 | Kusanagi et al. |
| 7,220,491 B2 | 5/2007 | Rouns et al. |
| 7,235,592 B2 | 6/2007 | Muratoglu et al. |
| 7,279,174 B2 | 10/2007 | Pacetti et al. |
| 7,279,507 B2 | 10/2007 | Hu et al. |
| 7,303,814 B2 | 12/2007 | Lamberti et al. |
| 7,335,205 B2 | 2/2008 | Aeschlimann et al. |
| 7,341,593 B2 | 3/2008 | Auxepaules et al. |
| 7,371,257 B2 | 5/2008 | Sahatjian et al. |
| 7,387,810 B2 | 6/2008 | Hossainy |
| 7,468,075 B2 | 12/2008 | Lang et al. |
| 7,476,398 B1 | 1/2009 | Doillon et al. |
| 7,563,483 B2 | 7/2009 | Hossainy et al. |
| 7,618,462 B2 | 11/2009 | Ek |
| 7,678,151 B2 | 3/2010 | Ek |
| 7,713,305 B2 | 5/2010 | Ek |
| 7,824,666 B2 | 11/2010 | Wolff et al. |
| 8,252,851 B2 | 8/2012 | Young et al. |
| 8,497,023 B2 | 7/2013 | Myung et al. |
| 8,679,190 B2 | 3/2014 | Myung et al. |
| 8,853,294 B2 | 10/2014 | Myung et al. |
| 8,883,915 B2 | 11/2014 | Myung et al. |
| 9,114,024 B2 | 8/2015 | Kourtis et al. |
| 9,387,082 B2 | 7/2016 | Myung et al. |
| 9,750,842 B2 | 9/2017 | Kourtis et al. |
| 10,457,803 B2 * | 10/2019 | Myung ............... C08F 220/06 |
| 2001/0029399 A1 | 10/2001 | Ku |
| 2001/0044026 A1 | 11/2001 | Vaghefi et al. |
| 2002/0022884 A1 | 2/2002 | Mansmann |
| 2002/0055007 A1 | 5/2002 | Soane et al. |
| 2002/0082699 A1 | 6/2002 | Ward et al. |
| 2002/0091229 A1 | 7/2002 | Hubbell et al. |
| 2002/0173855 A1 | 11/2002 | Mansmann |
| 2002/0198280 A1 | 12/2002 | Baba et al. |
| 2003/0008396 A1 | 1/2003 | Ku |
| 2003/0022216 A1 | 1/2003 | Mao et al. |
| 2003/0028196 A1 | 2/2003 | Bonutti |
| 2003/0083389 A1 | 5/2003 | Kao et al. |
| 2003/0083433 A1 | 5/2003 | James et al. |
| 2003/0092777 A1 | 5/2003 | Leitner |
| 2003/0100666 A1 | 5/2003 | DeGroot et al. |
| 2003/0114936 A1 | 6/2003 | Sherwood et al. |
| 2003/0130741 A1 | 7/2003 | McMinn |
| 2003/0153981 A1 | 8/2003 | Wang et al. |
| 2003/0170308 A1 | 9/2003 | Cleary et al. |
| 2004/0028804 A1 | 2/2004 | Anderson et al. |
| 2004/0034437 A1 | 2/2004 | Schmieding |
| 2004/0044410 A1 | 3/2004 | Ferree et al. |
| 2004/0059425 A1 | 3/2004 | Schmieding |
| 2004/0116564 A1 | 6/2004 | Devlin et al. |
| 2004/0133275 A1 | 7/2004 | Mansmann |
| 2004/0134502 A1 | 7/2004 | Mizuno et al. |
| 2004/0138382 A1 | 7/2004 | Dous |
| 2004/0139382 A1 | 7/2004 | Kim |
| 2004/0147466 A1 | 7/2004 | Barman et al. |
| 2004/0147927 A1 | 7/2004 | Tsougarakis et al. |
| 2004/0153040 A1 | 8/2004 | Martineau et al. |
| 2004/0153079 A1 | 8/2004 | Tsougarakis et al. |
| 2004/0153163 A1 | 8/2004 | Posner |
| 2004/0167528 A1 | 8/2004 | Schantz |
| 2004/0171740 A1 | 9/2004 | Ruberti et al. |
| 2004/0199250 A1 | 10/2004 | Fell |
| 2004/0204760 A1 | 10/2004 | Fitz et al. |
| 2004/0214914 A1 | 10/2004 | Marmo |
| 2004/0230315 A1 | 11/2004 | Ek |
| 2004/0236424 A1 | 11/2004 | Berez et al. |

(56) References Cited

U.S. PATENT DOCUMENTS

| | | |
|---|---|---|
| 2004/0266941 A1 | 12/2004 | Houston et al. |
| 2004/0267363 A1 | 12/2004 | Fell et al. |
| 2005/0004306 A1 | 1/2005 | Lubnin et al. |
| 2005/0013793 A1 | 1/2005 | Beckman et al. |
| 2005/0027364 A1 | 2/2005 | Kim et al. |
| 2005/0033295 A1 | 2/2005 | Wisnewski |
| 2005/0038520 A1 | 2/2005 | Binette et al. |
| 2005/0049459 A1 | 3/2005 | Hern |
| 2005/0055044 A1 | 3/2005 | Kangas |
| 2005/0065616 A1 | 3/2005 | Ankorina-Stark et al. |
| 2005/0090612 A1 | 4/2005 | Soane et al. |
| 2005/0113836 A1 | 5/2005 | Lozier et al. |
| 2005/0113928 A1 | 5/2005 | Cragg et al. |
| 2005/0126680 A1 | 6/2005 | Aeschlimann et al. |
| 2005/0142162 A1 | 6/2005 | Hunter et al. |
| 2005/0147685 A1 | 7/2005 | Osada et al. |
| 2005/0171604 A1 | 8/2005 | Michalow |
| 2005/0186248 A1 | 8/2005 | Hossainy et al. |
| 2005/0187146 A1 | 8/2005 | Helmus et al. |
| 2005/0215660 A1 | 9/2005 | Tomikawa et al. |
| 2005/0218541 A1 | 10/2005 | Peng et al. |
| 2005/0228161 A1 | 10/2005 | Benz et al. |
| 2005/0251267 A1 | 11/2005 | Winterbottom et al. |
| 2005/0251268 A1 | 11/2005 | Truncale |
| 2005/0267482 A1 | 12/2005 | Hyde |
| 2005/0267584 A1 | 12/2005 | Burdulis et al. |
| 2005/0278025 A1 | 12/2005 | Ku et al. |
| 2005/0283255 A1 | 12/2005 | Geremakis et al. |
| 2005/0287187 A1 | 12/2005 | Mansmann |
| 2006/0008506 A1 | 1/2006 | Cipriano De Sousa et al. |
| 2006/0052878 A1 | 3/2006 | Schmieding |
| 2006/0083773 A1 | 4/2006 | Myung et al. |
| 2006/0093648 A1 | 5/2006 | Coury et al. |
| 2006/0105295 A1 | 5/2006 | Mayer et al. |
| 2006/0111726 A1 | 5/2006 | Felt et al. |
| 2006/0122543 A1 | 6/2006 | Mayer et al. |
| 2006/0134186 A1 | 6/2006 | Carlton et al. |
| 2006/0142406 A1 | 6/2006 | Schmitt et al. |
| 2006/0148985 A1 | 7/2006 | Karthauser |
| 2006/0188487 A1 | 8/2006 | Thomas et al. |
| 2006/0188940 A1 | 8/2006 | Cima et al. |
| 2006/0193899 A1 | 8/2006 | Sawhney |
| 2006/0224244 A1 | 10/2006 | Thomas et al. |
| 2006/0233855 A1 | 10/2006 | Seliktar et al. |
| 2006/0235517 A1 | 10/2006 | Hodorek |
| 2006/0235539 A1 | 10/2006 | Blunn et al. |
| 2006/0235542 A1 | 10/2006 | Hodorek et al. |
| 2006/0240478 A1 | 10/2006 | Nishimi et al. |
| 2006/0241629 A1 | 10/2006 | Krebs et al. |
| 2006/0241759 A1 | 10/2006 | Trieu |
| 2006/0246241 A1 | 11/2006 | Kruger et al. |
| 2006/0282169 A1 | 12/2006 | Felt et al. |
| 2006/0287721 A1 | 12/2006 | Myung et al. |
| 2006/0287730 A1 | 12/2006 | Segal et al. |
| 2007/0014828 A1 | 1/2007 | Fitzhugh et al. |
| 2007/0016211 A1 | 1/2007 | Botimer |
| 2007/0048382 A1 | 3/2007 | Meyer et al. |
| 2007/0067032 A1 | 3/2007 | Felt et al. |
| 2007/0068816 A1 | 3/2007 | Solomon et al. |
| 2007/0078388 A1 | 4/2007 | Kangas |
| 2007/0078518 A1 | 4/2007 | Lavi |
| 2007/0083266 A1 | 4/2007 | Lang |
| 2007/0087031 A1 | 4/2007 | Ashman et al. |
| 2007/0088444 A1 | 4/2007 | Hodorek et al. |
| 2007/0098675 A1 | 5/2007 | Elisseeff et al. |
| 2007/0099840 A1 | 5/2007 | Ulijn et al. |
| 2007/0100457 A1 | 5/2007 | Hyde |
| 2007/0118218 A1 | 5/2007 | Hooper |
| 2007/0126982 A1 | 6/2007 | Myung et al. |
| 2007/0134291 A1 | 6/2007 | Ting et al. |
| 2007/0135922 A1 | 6/2007 | Trieu |
| 2007/0141108 A1 | 6/2007 | Thomas et al. |
| 2007/0142914 A1 | 6/2007 | Jones et al. |
| 2007/0149441 A1 | 6/2007 | Aeschlimann et al. |
| 2007/0167541 A1 | 7/2007 | Ruberti et al. |
| 2007/0179605 A1 | 8/2007 | Myung et al. |
| 2007/0179607 A1 | 8/2007 | Hodorek et al. |
| 2007/0179622 A1 | 8/2007 | Denoziere et al. |
| 2007/0191963 A1 | 8/2007 | Winterbottom et al. |
| 2007/0198022 A1 | 8/2007 | Lang et al. |
| 2007/0202148 A1 | 8/2007 | Ringeisen et al. |
| 2007/0219640 A1 | 9/2007 | Steinberg |
| 2007/0224238 A1 | 9/2007 | Mansmann et al. |
| 2007/0225823 A1 | 9/2007 | Hawkins et al. |
| 2007/0233240 A1 | 10/2007 | Frank et al. |
| 2007/0233269 A1 | 10/2007 | Steines et al. |
| 2007/0265704 A1 | 11/2007 | Mayer et al. |
| 2007/0270783 A1 | 11/2007 | Zumsteg et al. |
| 2007/0276394 A1 | 11/2007 | Johnson et al. |
| 2008/0058954 A1 | 3/2008 | Trieu |
| 2008/0070086 A1 | 3/2008 | Fukuchi et al. |
| 2008/0077249 A1 | 3/2008 | Gradel |
| 2008/0103505 A1 | 5/2008 | Fransen |
| 2008/0124376 A1 | 5/2008 | Pruitt et al. |
| 2008/0139694 A1 | 6/2008 | Ratcliffe |
| 2008/0182919 A1 | 7/2008 | Saimi et al. |
| 2008/0241214 A1 | 10/2008 | Myung et al. |
| 2008/0269370 A1 | 10/2008 | Myung et al. |
| 2008/0317818 A1 | 12/2008 | Griffith et al. |
| 2009/0035344 A1 | 2/2009 | Thomas et al. |
| 2009/0062408 A1 | 3/2009 | Liu et al. |
| 2009/0062423 A1 | 3/2009 | Betz et al. |
| 2009/0088846 A1 | 4/2009 | Myung et al. |
| 2009/0142508 A1 | 6/2009 | Lai et al. |
| 2009/0163860 A1 | 6/2009 | Patrick et al. |
| 2009/0176891 A1 | 7/2009 | Chogle et al. |
| 2009/0209966 A1 | 8/2009 | Chandler |
| 2009/0221730 A1 | 9/2009 | Kowalski et al. |
| 2009/0233887 A1 | 9/2009 | Shalaby et al. |
| 2009/0234044 A1 | 9/2009 | Rheinberger et al. |
| 2009/0240337 A1 | 9/2009 | Myung et al. |
| 2009/0281545 A1 | 11/2009 | Stubbs |
| 2009/0312807 A1 | 12/2009 | Boudreault et al. |
| 2010/0010114 A1 | 1/2010 | Myung et al. |
| 2010/0032090 A1 | 2/2010 | Myung et al. |
| 2010/0056646 A1 | 3/2010 | Shalaby et al. |
| 2010/0125341 A1 | 5/2010 | Frauens |
| 2011/0152868 A1 | 6/2011 | Kourtis et al. |
| 2011/0184423 A1 | 7/2011 | Rushton et al. |
| 2011/0237705 A1 | 9/2011 | Leonard et al. |
| 2012/0045651 A1 | 2/2012 | Myung et al. |
| 2012/0116531 A1 | 5/2012 | Forsell |
| 2012/0209396 A1 | 8/2012 | Myung et al. |
| 2012/0232657 A1 | 9/2012 | Myung et al. |
| 2012/0277807 A1 | 11/2012 | Myung et al. |
| 2012/0308508 A1 | 12/2012 | Saunders et al. |
| 2013/0096691 A1 | 4/2013 | Myung et al. |
| 2013/0103157 A1 | 4/2013 | Kourtis et al. |
| 2013/0131741 A1 | 5/2013 | Kourtis et al. |
| 2013/0138210 A1 | 5/2013 | Myung et al. |
| 2013/0138211 A1 | 5/2013 | Myung et al. |
| 2013/0217829 A1 | 8/2013 | Myung et al. |
| 2014/0172098 A1 | 6/2014 | Myung et al. |
| 2015/0025161 A1 | 1/2015 | Myung et al. |
| 2015/0272599 A1 | 10/2015 | Kourtis et al. |
| 2015/0284654 A1 | 10/2015 | Myung et al. |
| 2016/0346089 A1 | 12/2016 | Myung et al. |
| 2017/0107370 A1 | 4/2017 | Myung et al. |
| 2017/0327624 A1 | 11/2017 | Kourtis et al. |
| 2017/0348011 A1 | 12/2017 | Kourtis et al. |
| 2019/0218386 A1 | 7/2019 | Kourtis et al. |
| 2019/0224367 A1 | 7/2019 | Kourtis et al. |
| 2020/0023098 A1 | 1/2020 | Kourtis et al. |
| 2020/0046880 A1 | 2/2020 | Kourtis et al. |

FOREIGN PATENT DOCUMENTS

| | | |
|---|---|---|
| EP | 2268331 A2 | 1/2011 |
| EP | 2626090 A2 | 8/2013 |
| GB | 2372707 A | 9/2002 |
| JP | H06-287443 A | 10/1994 |
| JP | H09-077809 A | 3/1997 |
| JP | H10-500038 A | 1/1998 |
| JP | 3176176 B2 | 6/2001 |

(56) References Cited

FOREIGN PATENT DOCUMENTS

| | | |
|---|---|---|
| JP | 2002514233 A | 5/2002 |
| JP | 2002518564 A | 6/2002 |
| JP | 2002518565 A | 6/2002 |
| JP | 2003171475 A | 6/2003 |
| JP | 2004512079 A | 4/2004 |
| JP | 2004515311 A | 5/2004 |
| JP | 2005305162 A | 11/2005 |
| JP | 2006517842 A | 8/2006 |
| JP | 2007501674 A | 2/2007 |
| WO | WO-94/01468 A1 | 1/1994 |
| WO | WO-95/30388 A1 | 11/1995 |
| WO | WO-98/06768 A1 | 2/1998 |
| WO | WO-99/45978 A1 | 9/1999 |
| WO | WO-99/67311 A1 | 12/1999 |
| WO | WO-99/67312 A1 | 12/1999 |
| WO | WO-00/02937 A1 | 1/2000 |
| WO | WO-00/043050 A1 | 7/2000 |
| WO | WO-02/026848 A2 | 4/2002 |
| WO | WO-03/009337 A2 | 1/2003 |
| WO | WO-2004/032767 A1 | 4/2004 |
| WO | WO-2004/055057 A1 | 7/2004 |
| WO | WO-2004/073563 A2 | 9/2004 |
| WO | WO-2004/091685 A2 | 10/2004 |
| WO | WO-2007/067697 A2 | 6/2007 |
| WO | WO-2007/068625 A1 | 6/2007 |
| WO | WO-2007/112305 A2 | 10/2007 |
| WO | WO-2008/100617 A1 | 8/2008 |
| WO | WO-2009/071937 A1 | 6/2009 |
| WO | WO-2010/037685 A1 | 4/2010 |
| WO | WO-2010/059495 A2 | 5/2010 |
| WO | WO-2012/096997 A2 | 7/2012 |
| WO | WO-2015/023569 A1 | 2/2015 |

OTHER PUBLICATIONS

Barszczewska-Rybarek, Izabela M.; Quantitative determination of degree of conversion in photocured poly (urethane-dimethacrylate)s by Fourier transform infrared spectroscopy; Journal of Applied Polymer Science; vol. 123; issue 3; pp. 1604-1611; Feb. 5, 2012.
Bobyn et al., The optimum pore size for the fixation of porous-surfaced metal implants by the ingrowth of bone. Clin Orthop Relat Res, Jul./Aug. 1980(150): p. 263-70.
Borden et al.; The sintered microsphere matrix for bone tissue engineering: In vitroosteoconductivity studies; J. Biomed. Mat. Res.; 61(3); pp. 421-429; Sep. 2002.
Brodbeck et al., Biomaterial adherent macrophage apoptosis is increased by hydrophilic and anionic substrates in vivo. Proc Natl Acad Sci U S A, Aug. 6, 2002. 99(16): p. 10287-92.
Brown et al.; Solvent/Non-solvent sintering: A novel route to create porous microsphere scaffolds for tissue regeneration; J. Biomed. Mat. Res. (Part B: Applied Biomaterials); 86B(2); pp. 396-406; Aug. 2008.
Causton et al.; Dental materials: 1981 literature review Part 1; Journal of Dentistry; vol. 12; Issue 1; pp. 1R28; Mar. 1984.
Charnley, J.; Anchorage of the femoral head prosthesis to the shaft of the femur; J Bone Joint Surg Br.; 42-B:28-30; Feb. 1960.
Chen et al.; Mechanical Properties of Polyepichlorohydrin Polyurethane/Poly(methyl methacrylate) IPNs; Chinese J Appl Chem; 12(4):66-69; Aug. 1995 (wEngAbs).
Christenson et al., "Antioxidant inhibition of poly(carbonate urethane) in vivo biodegradation," J Biomed Mater Res A. 76(3): 480-490 (2006).
Covert et al.; Friction characteristics of a potential articular cartilage biomaterial. Wear, Aug. 2003. 255: p. 1064-1068.
Depuy Orthopaedics; Bone Cement Time Setting Chart; product file; date of publication unknown; available to applicants at least as of Jul. 2012.
Dror et al.; Gradient interpenetrating polymer networks. I. Poly(ether urethane) and polyacrylamide IPN; J of Applied Polymer Science; 26; pp. 1741-1757; Jun. 1981.

Elbert; Liquid-liquid two phase systems for the production of porous hydrogels and hydrogel microsphers for biomedical applications: A tutorial review; Acta Biomater; 7(1); pp. 31-56; Jan. 31, 2011.
Elmer's Products Inc.; Material Safety Data Sheet; "Elmer's Nano Glue"; Jun. 13, 2007.
Elsabee et al.; Gradient interpenetrating polymer networks. II. Polyacrylamide gradients in poly(ether urethane); J of Applied Polymer Science; 28(7); pp. 2151-2166; Jun. 1983.
Esstech, Inc.; Urethane Dimethacrylate (product specification); 1 pg.; Note: this document was available to applicant(s) at least as of (Apr. 8, 2015).
Evans et al.; The use of corneal organ culture in biocompatibility studies; Biomaterials; vol. 23; pp. 1359-1367; Mar. 2002.
Forsell; U.S. Appl. No. 61/229,735 entitled "Hip Joint Method," filed Jul. 30, 2009.
Frank, Curt; Structure-property relationships for hydrogels with applications to biomedical devices; Presentation at American Chemical Society Mtg; San Francisco, CA; Sep. 11, 2006.
Gao et al.; Grafting of hydrophilic monomers onto polyurethane membranes by solution or pre-absorbing methods for acceleration of cell compatibility; Chinese Journal of Polymer Science; vol. 19; No. 5; pp. 493-498; Oct. 20, 2001.
Gong et al.; Double-network hydrogels with extremely high mechanical strength; Adv. Mater.; vol. 15; No. 14; pp. 1155-1158; Jul. 17, 2003.
Gorna et al., "Biodegradable porous polyurethane scaffolds for tissue repair and regeneration," J Biomed Mater Res A. 79(1):128-38 (2006).
Gorna et al.; Preparation, degradation, and calcification of biodegradable polyurethane foams for bone graft substitutes; J Biomed Mater Res A. 67(3): 813-827 (2003).
Goswami et al.; Engineering properties of novolac resin-PMMA {Poly(methyl methacrylate)} IPN system; Journal of Applied Science; 93(6); pp. 2764-2774; Jul. 16, 2004.
Guelcher et al.; Synthesis and in vitro biocompatibility of injectable polyurethane foam scaffolds; Tissue Engineering; 12(5); pp. 1247-1259; May 2006.
Guelcher et al.; Synthesis of biocompatible segmented polyurethanes from aliphatic diisocyanates and diurea diol chain extenders; Acta biomaterialia; 1(4); pp. 471-484; Jul. 2005.
Gunatillake et al.; Designing biostable polyurethane elastomers for biomedical implants; Aust. J. Chem.; vol. 56; pp. 545-557; Jun. 2003.
Hern et al.; Incorporation of adhesion peptides into nonadhesive hydrogels useful for tissue resurfacing; J. Biomed. Materials Research; vol. 39; No. 1; pp. 266-276; Feb. 1998.
Hsieh et al.; Compatibility and Morphology in Polyurethane and Polystyrene Ionomeric Interpenetrating Polymer Networks; Polymer Journal; 21(1); pp. 1-10; Jan. 15, 1989.
International Search Report for International Application No. PCT/US08/01642, dated May 16, 2008 (1 page).
International Search Report for International Application No. PCT/US16/46350, dated Oct. 14, 2016 (3 pages).
International Search Report for International Application No. PCT/US19/42193, dated Sep. 27, 2019 (3 pages).
International Search Report for International Application No. PCT/US2008/004976, dated Oct. 15, 2009 (4 pages).
Ithaca College Gross Anatomy; Joints of the Back; ; 4 pgs. (downloaded Dec. 1, 2013 from http://www.ithaca.edu/faculty/lahr/LE2000/Back/Jointpage.htm).
Iwasaki et al., Hydrogel like elastic membrane consisting of semi-interpenetrating polymer networks based on a phosphorylcholine polymer and a segmented polyurethane; J. Polym. Sci Part A: Polym Chem; 41; pp. 68-75; Jan. 2003.
Jones et al.; Sequential Polyurethane-Poly(Methylmethacrylate) Interpenetrating Polymer Networks as Ureteral Biomaterials: Mechanical Properties and Comparative Resistance to Urinaryencrustation; J Mater Sci Mater Med; 8(11):713-717; Nov. 1997.
Kagata et al., "Friction of Gels. 6. Effects of Sliding Velocity and Viscoelastic Responses of the Network," J Phys Chem B. 106(18):4596-601 (2002).

(56) References Cited

OTHER PUBLICATIONS

Kaneko et al., "Mechanically Strong Hydrogels with Ultra-Low Frictional Coefficients," Advanced Materials. 17(5):535-8 (2005).
Kanie et al.; Flexural properties of ethyl or methyl methacrylate-UDMA blend polymers; Dent Mater J; 29(5); pp. 575-581; Oct. 2010.
Khan et al., Analysis and evaluation of a biomedical polycarbonate urethane tested in an in vitro study and an ovine arthroplasty model. Part I: materials selection and evaluation. Biomaterials, Feb. 2005. 26(6): p. 621-31.
Kim et al.; Adhesion and growth of endothelial cell on amphiphilic PU/PS IPN surface: effect of amphiphilic balance and immobilized collagen; Journal of Biomedical Materials Research; 62(4); pp. 613-621; Sep. 6, 2002.
Kim et al.; Electrical/pH Responsive Properties of Poly(2-acrylamido-2-methylpropane sulfonic acid)/Hyaluronic Acid Hydrogels; Journal of Applied Polymer Science; vol. 92; issue 3; pp. 1731-1736; May 2004.
Kim et al.; Electrochemical behavior of an interpenetrating polymer network hydrogel composed of poly (propylene glycol) and poly(acrylic acid); Journal of Applied Polymer Science; vol. 89; pp. 2301-2305; Aug. 2003.
Kim et al.; Water sorption of ploy(propylene glycol)/poly(acrylic acid) interpenetrating polymer network hydrogels; Reactive & Functional Polymers; vol. 55; pp. 69-73; Feb. 2003.
Kourtis et al., U.S. Appl. No. 13/573,788, entitled "Polymeric adhesive for anchoring compliant materials to another surface," filed Oct. 3, 2012 (103 pages).
Kourtis et al., U.S. Appl. No. 13/683,731, entitled "Systems, Devices, and Methods for Anchoring Orthopaedic Implants to Bone," filed Nov. 21, 2012 (130 pages).
Kourtis et al.; U.S. Appl. No. 14/831,746 entitled "Systems, devices, and methods for anchoring orthopaedic implants to bone," filed Aug. 20, 2015.
Kourtis et al.; U.S. Appl. No. 15/442,413, entitled "Method, device, and system for shaving and shaping of a joint," filed Feb. 24, 2017 (69 pages).
Kourtis et al.; U.S. Appl. No. 15/668,547, entitled "Polymeric adhesive for achoring compliant materials to another surface," filed Aug. 3, 2017 (109 pages).
Kourtis et al.; U.S. Appl. No. 15/752,168, entitled "Interpenetrating polymer networks," filed Feb. 12, 2018 (109 pages).
Kourtis et al.; U.S. Appl. No. 12/973,829, entitled "Method, device, and system for shaving and shaping of a joint," filed Dec. 20, 2010 (69 pages).
Kwong et al.; A comparison of the shrinkage of commercial bone cements when mixed under vacuum; J Bone Joint Surg Br.; 88(1):120-2; Jan. 2006.
Lam et al.; Update on Ureteral Stents; Urology; 64:9-15; Jul. 2004.
Lamba et al.; Polyurethanes in Biomedical Application; CRC Press; pp. 11, 14, 16, 18-20, 57-59, 73, 79 & 104; Nov. 1997.
Lee et al.; Interpenetrating polymer network hydrogels based on poly (ethylene glycol) macromer and chitosan; Carbohydrate Polymer; vol. 41; No. 2; pp. 197-205; Feb. 2000.
Lewis G.; Properties of acrylic bone cement: state of the art review; J Biomed Mater Res.; 38(2):155-82; Summer Jun.-Aug. 1997.
Lipatov et al.; Gradient interpenetrating polymer networks; Journal of Materials Science; 30(4); pp. 1095-1104; Feb. 1995.
Lu et al.; Release behavior of high molecular weight solutes from poly(ethylene glycol)-based degradable networks; Macromolecules; vol. 33(7); pp. 2509-2515; Mar. 2000.
Maroudas et al.; Permeability of articular cartilage; Nature; vol. 219(5160); pp. 1260-1261; Sep. 21, 1968.
Matinlinna et al., "Isocyanato- and Methacryloxysilanes Promote Bis-GMA Adhesion to Titanium," J Dent Res. 84(4):360-364 (2005).
MIT.edu; Material Modulus Properties; 2pgs.; Feb. 8, 2007 (downloaded Nov. 27, 2013 from http://web.archive.org/web/*/http://web.mit.edu/course/3/3.11/www/modules-/props.pdf).
Morgan et al.; Dependence of yield strain of human trabecular bone on anatomic site; J Biomech.; 34(5):569-77; May 2001.
Mow et al., Basic Orthopaedic Biomechanics and Mechano-Biology, Lippincot Williams and Wilkins, 3rd Edition, Apr. 2005, pp. 459-461.
Myung et al.; Biomimetic strain hardening in interpenetrating polymer network hydrogels; Polymer,; vol. 48; No. 18; pp. 5376-5387; Jun. 2007.
Myung et al.; U.S. Appl. No. 12/409,359, entitled "Methods, devices and compositions for adhering hydrated polymer implants to bone," filed Mar. 23, 2009 (45 pages).
Myung et al.; U.S. Appl. No. 12/499,041, entitled "Hydrophilic Interpenetrating Polymer Networks Derived From Hydrophobic Polymers," filed Jul. 7, 2009 (95 pages).
Myung et al.; U.S. Appl. No. 12/536,233, entitled "Polyurethane-grafted hydrogels," filed Aug. 5, 2009 (51 pages).
Myung et al.; U.S. Appl. No. 13/347,647, entitled "Orthopedic implants having gradient polymer alloys," filed Jan. 10, 2012 (144 pages).
Myung et al.; U.S. Appl. No. 13/418,294, entitled "Hydrogel Anthroplasty Device," filed Mar. 12, 2012 (99 pages).
Myung et al.; U.S. Appl. No. 13/542,464, entitled "Methods, Devices and Compositions for Adhering Hydrated Polymer Implants to Bone," filed Jul. 5, 2012 (48 pages).
Myung et al.; U.S. Appl. No. 13/748,573, entitled "Hydrophilic Interpenetrating Polymer Networks Derived From Hydrophobic Polymers," filed Jan. 23, 2013 (99 pages).
Myung et al.; U.S. Appl. No. 13/748,576, entitled "Hydrophilic Interpenetrating Polymer Networks Derived From Hydrophobic Polymers," filed Jan. 23, 2013 (103 pages).
Myung et al.; U.S. Appl. No. 13/816,537, entitled "Hydrophobic and Hydrophilic Interpenetrating Polymer Networks Derived From Hydrophobic Polymers and Methods of Preparing the Same," filed Apr. 24, 2013 (153 pages).
Myung et al.; U.S. Appl. No. 13/905,028, entitled "Polyurethane-grafted hydrogels," filed May 29, 2013 (58 pages).
Myung, David; Structure, properties, and medical device applications of mechanically enhanced, biometric hydrogel alloys; Doctoral Thesis; Stanford University; Dec. 2007.
Nanci et al., "Chemical modification of titanium surfaces for covalent attachment of biological molecules," J Biomed Mater Res. 40(2):324-35 (1998) (13 pages).
Neurosurgical.com; Spinal Anatomy: The Regions of the Spine; 5pgs. (downloaded Dec. 1, 2013 http://www.neurosurgical.com/neuro_medical_info/spinal_anatomy.htm).
Ohman et al.; Mechanical testing of cancellous bone from the femoral head: experimental errors due to off-axis measurements; J Biomech.; 40(11):2426-33; (year of publication is sufficiently earlier than the effective U.S. filing date and any foreignpriority date) 2007.
Orr et al.; Shrinkage stresses in bone cement; Biomaterials; 24(17):2933-40; Aug. 2003.
Pan et al., "A study on the friction properties of poly (vinyl alcohol) hydrogel as articular cartiliage against titanium alloy," Wear. 262(7-8):1021-5 (2007).
Park et al.; Synthesis of PVA/PVP hydrogels having two-layer by radiation and their physical properties; Radiation Physics and Chemistry; 67(3-4); pp. 361-365; Jun. 2003.
Puska et al.; Exothermal Characteristics and Release of Residual Monomers from Fiber-reinforced Oligomer-modified Acrylic Bone Cement; J Biomat App; 20:51-64; Jul. 2005.
Realdictionary; Definition of Implant; 4pgs. (downloaded Dec. 1, 2013 from www.realdictionary.com/?q=implant).
Revzin et al., "Fabrication of Poly(ethylene glycol) Hydrogel Microstructures Using Photolithography," Langmuir. 17(18):5440-7 (2001).
Saito et al.; Preparation and properties of transparent cellulose hydrogels; J. Applied Polymer Science; 90(11); pp. 3020-3025; Dec. 2003.
Scholes et al.; Compliant layer acetabular cups: friction tsting of a range of materials and designs for a new generation of prosthesis that mimics the natural joint; Proc. IMechE; vol. 220(5); Part H; J. Engineering in Medicine; pp. 583-596, Jul. 2006.
Shalaby; U.S. Appl. No. 61/069,046 entitled "Hydroswellable, segmented, aliphatic polyurethanes and polyurethane ureas," filed Mar. 12, 2008.

(56) References Cited

OTHER PUBLICATIONS

Sigma-Aldrich; Methyl Methacrylate (product specification); 1 pg.; Note: this document was available to applicant(s) at least as of (Jun. 19, 2014).
Simon et al., "Study of two Grafting Methods for Obtaining a 3-Aminopropyltriethoxysilane Monolayer on Silica Surface," J Colloid Interface Sci. 251(2):278-83 (2002).
Spector et al.; Porous polymers for biological fixation. Clin Orthop Relat Res, Oct. 1988 (235): p. 207-19.
Stammen et al., Mechanical properties of a novel PVA hydrogel in shear and unconfined compression. Biomaterials, Apr. 2001. 22(8): p. 799-806.
Stryker Orthopaedics; SimplexTM P Bone Cement; Product Literature LSB Rev. 3, Mar. 2006.
Swieszkowski et al., "An elastic material for cartilage replacement in an arthritic shoulder joint," Biomaterials. 27(8):1534-41 (2006).
Tanaka et al.; Polymer properties on resins composed of UDMA and methacrylates with the carboxyl group; Dental Materials Journal; 20(3); pp. 206-215; Sep. 2001.
Tariq et al.; (Abstract) Sodium benzoate attenuates iminodipropionitrile-induced behavioral syndrome in rats. Behav pharmacol; Dec. 2004.
Tawfik, Dan; Amidation of carboxyl groups; The Protein Protocols Handbook, 2nd Ed.; Humana Press; pp. 477-478; Feb. 2002.
The Engineering Toolbox; Polyurethane insulation: {http://www.engineeringtoolbox.com/polyurethane-insulation-k-values-d_117-4.html} pp. 1-3; printed Oct. 21, 2011.
The Engineering Toolbox;Thermal conductivity of some common materials and gases: {http://www.engineeringtoolbox.com/thrmal-conductivity-d_429.html} pp. 1-2; printed Oct. 21, 2011.
The Gorilla Glue Company; Material Safety Data Sheet; "New Fast Cure-Dries White Gorilla Glue.RTM."; Jan. 30, 2007.
The Gorilla Glue Company; Material Safety Data Sheet; "New Stronger-Faster Gorilla Glue.RTM."; Jan. 26, 2007.
Van Landuyt et al.; Reinforcement of Osteosynthesis Screws with Brushite Cement; Bone; 25(2)(Suppl 1):95S-98S; Aug. 1999.
Wittemann et al.; Adsorption of proteins on spherical polyelectrolyte brushes in aqueous solution; Phys. Chem. Chem. Phys., Mar. 2003, vol. 5(8), pp. 1671-1677.
Wright et al., Wear studies on prosthetic materials using the pin-on-disc machine. Biomaterials, vol. 3, Issue 1, Jan. 1982, pp. 41R48.
Written Opinion for International Application No. PCT/US08/01642, dated May 16, 2008 (5 pages).
Written Opinion for International Application No. PCT/US16/46350, dated Oct. 14, 2016 (8 pages).
Written Opinion for International Application No. PCT/US19/42193, dated Sep. 27, 2019 (6 pages).
Written Opinion for International Application No. PCT/US2008/004976, dated Oct. 15, 2009 (6 pages).
Xiao et al., "Covalent Attachment of Cell-Adhesive, (Arg-Gly-Asp)-Containing Peptides to Titanium Surfaces," Langmuir.14(19):5507-16 (1998).
Yang et al.; Preparation of poly(acrylic acid) modified polyurethane membrane for biomaterial by UV radiation without degassing; J. Biomed. Mater. Res.; vol. 45(2); pp. 133-139; May 1999.
Yim et al., Biocompatibility of poly(ethylene glycol)/poly(acrylic acid)interpenetrating polymer network hydrogel particles inRAW 264.7 macrophage and MG-63 osteoblast cell lines. Journal of Biomedical Materials Research, 91A(3); pp. 894-902; Dec. 1, 2009.
Zhu et al.; (Abstract) Promoting the cytocompatibility of polyurethane scaffolds via surface photo-grafting polymerization of acrylamide; J. Mater. Sci. Mater. Med.; vol. 15; No. 3; pp. 283-289; Mar. 2004.

\* cited by examiner

FIG. 4B

SUPERFICIAL

| | gradient semi-IPN | osteochondral graft |
|---|---|---|
| Coefficient of Friction | 0.015 - 0.05 | 0.02 - 0.06 |
| Young's Modulus | 18 MPa | 12 MPa |
| Water Content | 50% | ~70% |
| Failure Stress | 48 MPa | 10 MPa |
| Failure Strain | 140% | 50% |

DEEP

| | gradient semi-IPN | osteochondral graft |
|---|---|---|
| Young's Modulus* | 100 - 1800 MPa | 200 - 2200 MPa |
| Water Content | <1% | N/A |
| Failure Stress | >16 MPa | 15 MPa |
| Failure Strain | >15% | <1% |
| Mean Pore Size | ~250 μm | 410 μm | hydration ← / → stiffness negative charge (gradient semi-IPN)

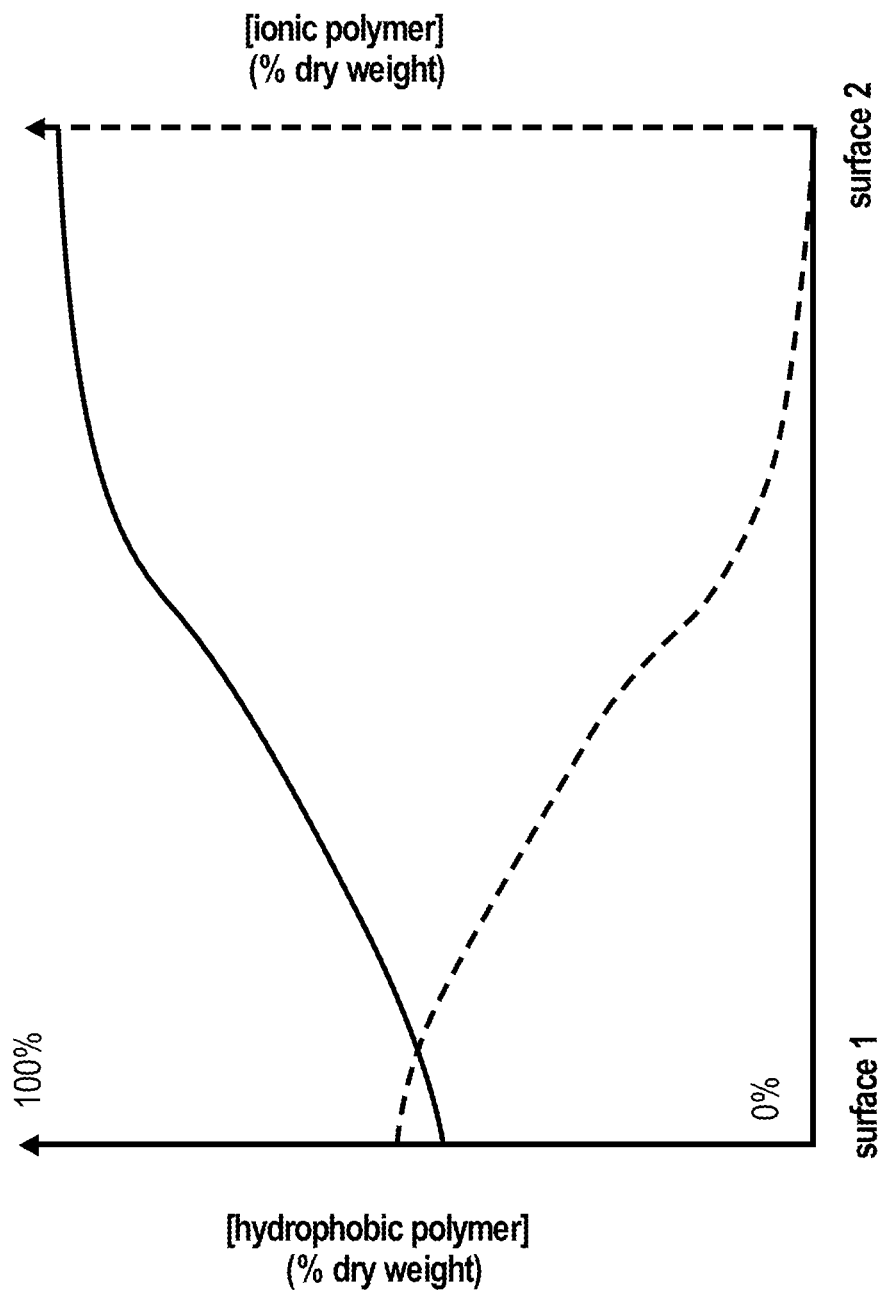

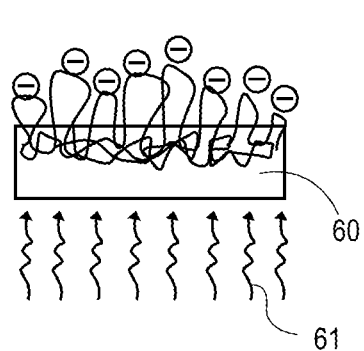 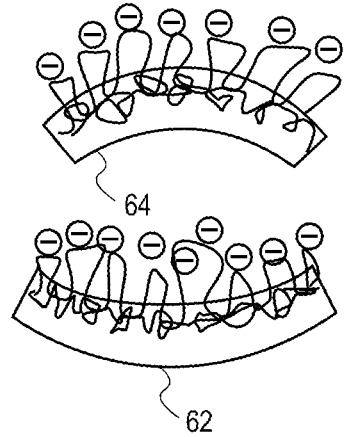
FIG. 6A  FIG. 6B
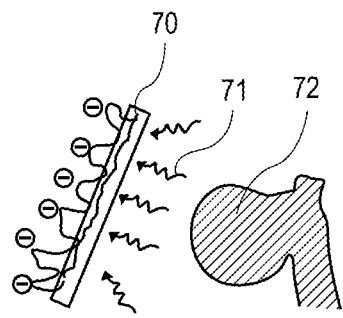 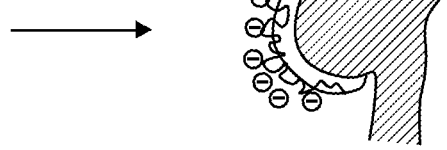
FIG. 7A  FIG. 7B
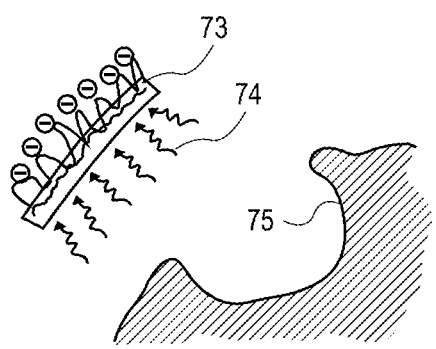 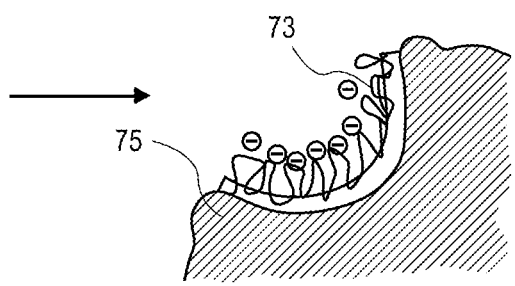
FIG. 7C  FIG. 7D

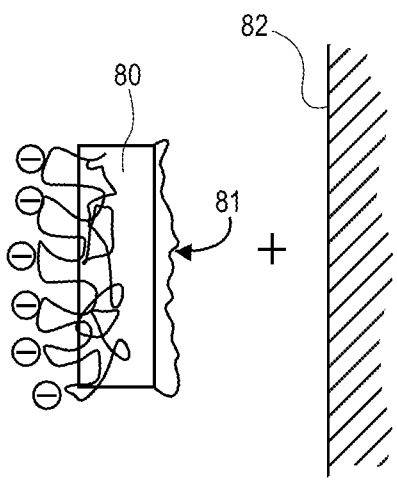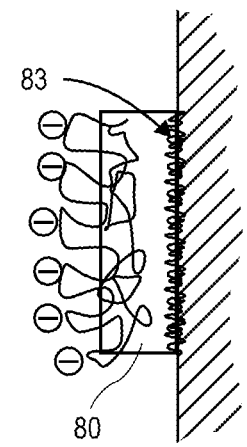
FIG. 8A      FIG. 8B
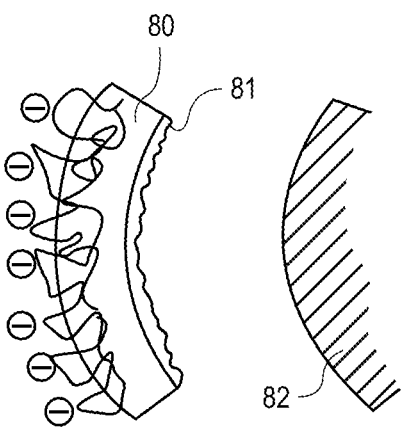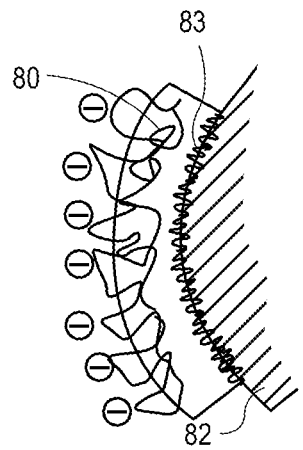
FIG. 8C      FIG. 8D

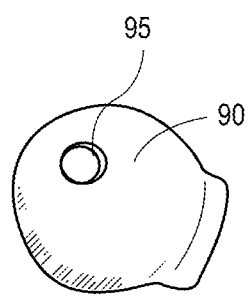
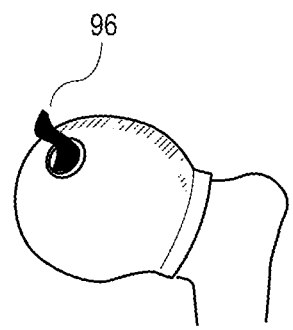
FIG. 10A    FIG. 10B
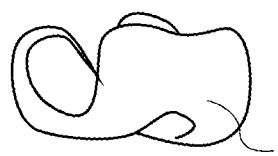
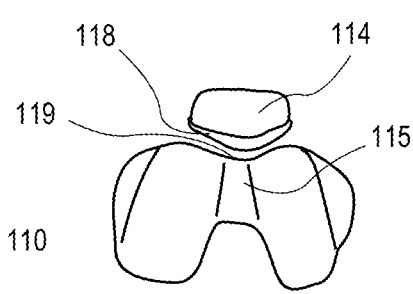
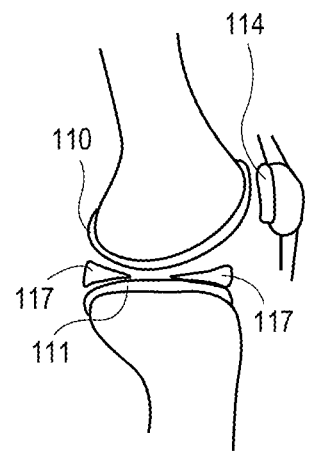
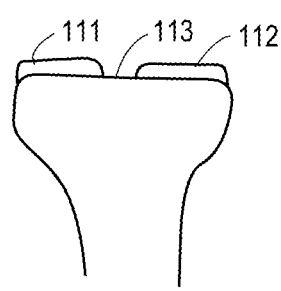
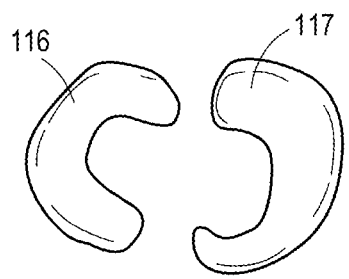
FIG. 11A    FIG. 11C
FIG. 11B    FIG. 11D    FIG. 11E

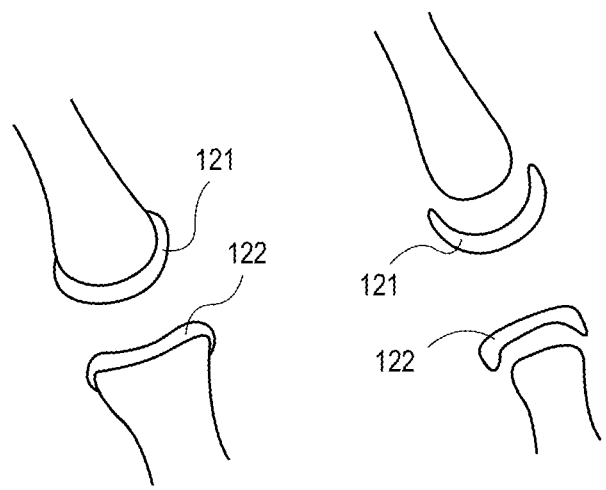
FIG. 12A  FIG. 12B
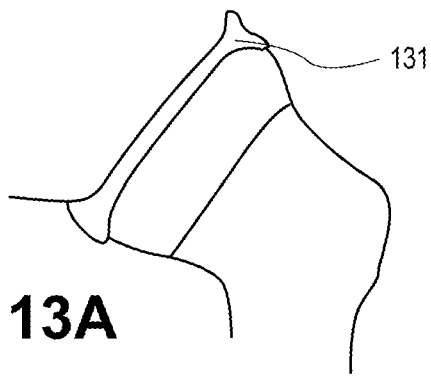
FIG. 13A
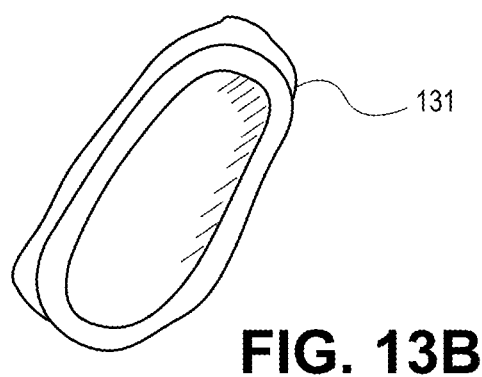
FIG. 13B

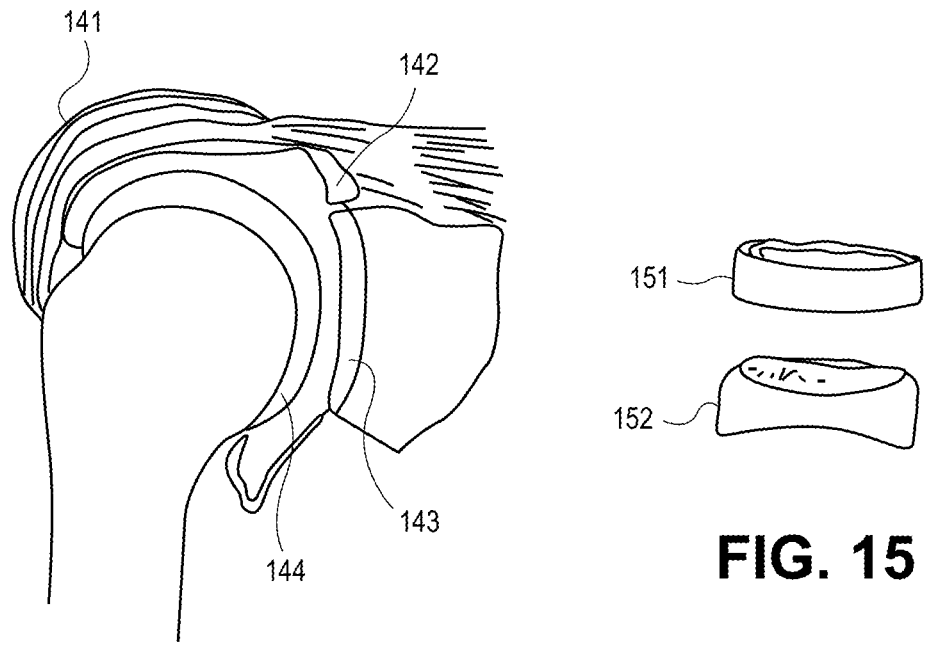
FIG. 14
FIG. 15
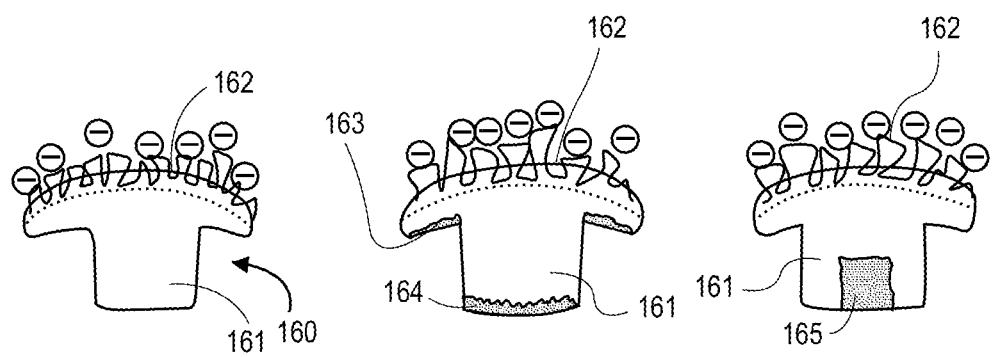
FIG. 16A  FIG. 16B  FIG. 16C
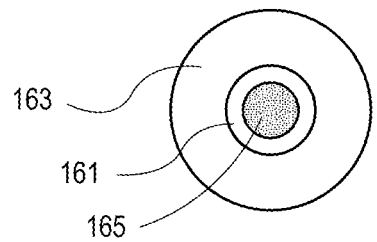
FIG. 16D

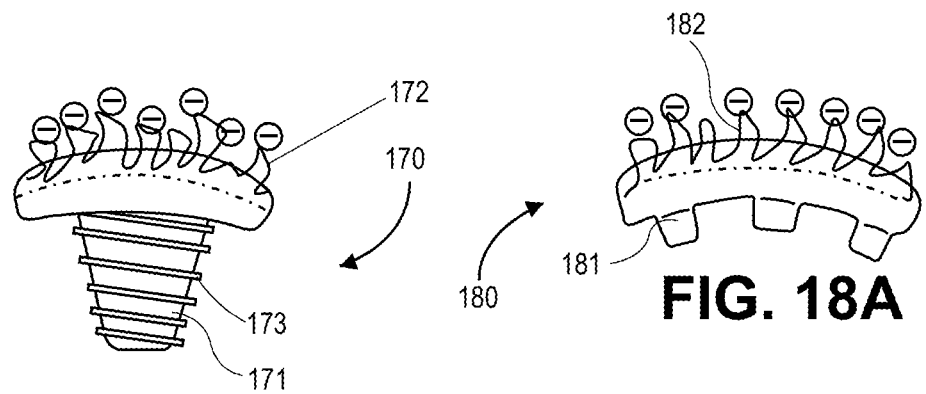
FIG. 17
FIG. 18A
FIG. 18B
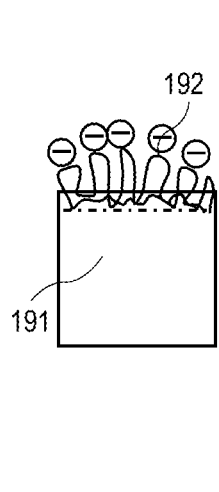 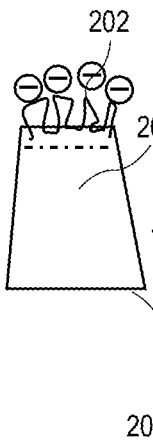 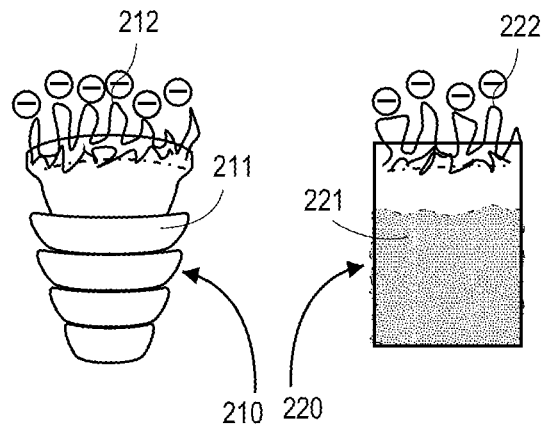
FIG. 19    FIG. 20    FIG. 21    FIG. 22

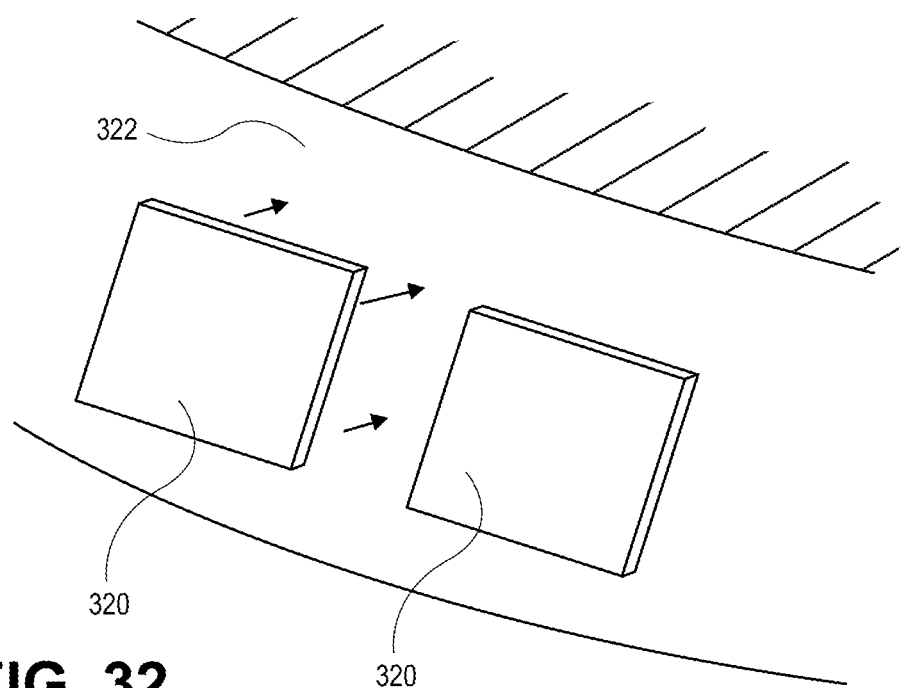
FIG. 32
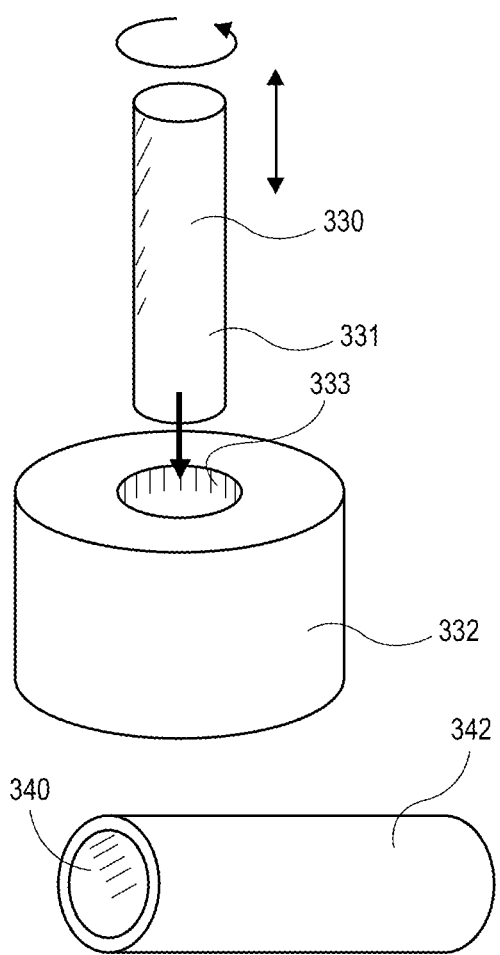
FIG. 33
FIG. 34

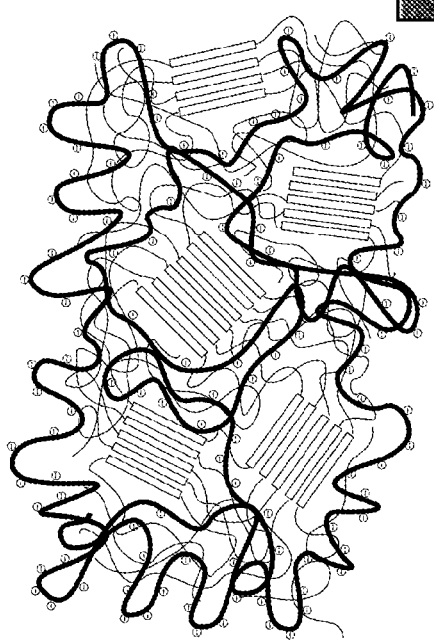
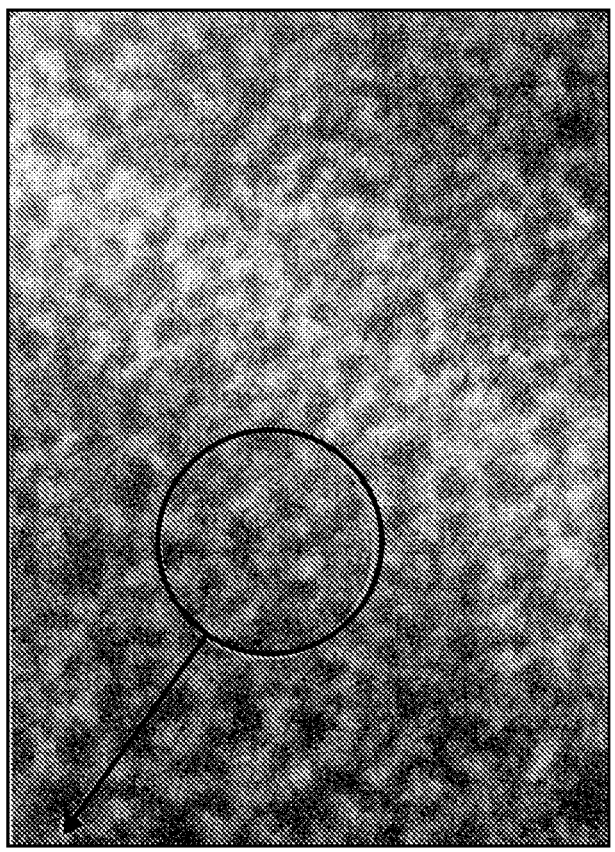
FIG. 38

| Sample ID | Heating Rate (°C per min) | Tg (°C) | Tm (°C) | Crystallization (°C) |
|---|---|---|---|---|
| PEU (Control) | 10 | - | 176 186 | 92 |
| PEU/PAA (Sample) | 10 | -20 | 154 | 79 |
| PEU (Control) | 40 | -22 | 178 | 93 |
| PEU/PAA (Sample) | 40 | -21 | 164 | 90 |

FIG. 41

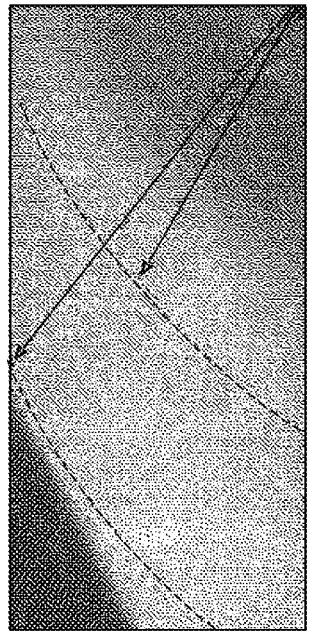
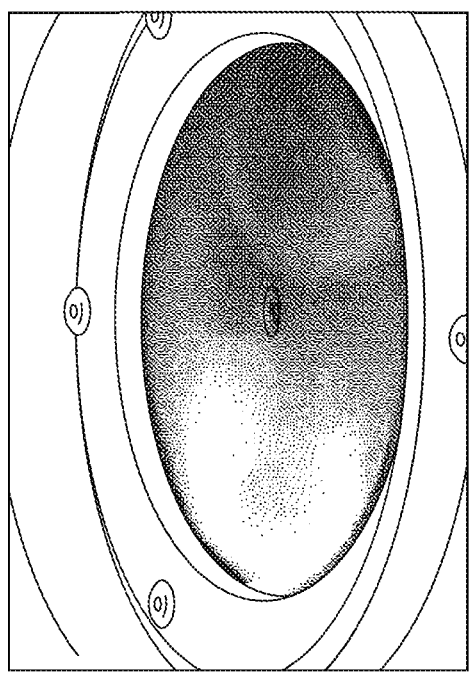
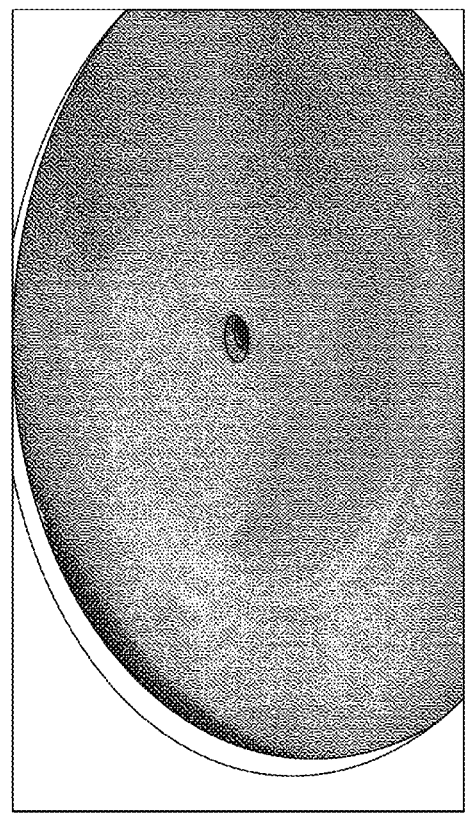
FIG. 44B
FIG. 44A
FIG. 44C

| Description | Solvent | % Change in mass due to swelling |
|---|---|---|
| Elasthane | $CH_2Cl_2$ | 150.6% |
| Elasthane | $CH_2=CHCOOH$ | 105.0% |
| Elasthane | $CH_3COOH$ | 86.6% |
| Elasthane | $CH_3COOCH_2CH_3$ | 41.3% |
| Elasthane | $O=C(CH_3)_2$ | 40.8% |
| Elasthane | $CH_3CH_2OH$ | 19.5% |
| Elasthane | $CH_3OH$ | 17.4% |
| Elasthane | $H_2O$ | 1.0% |
| Elasthane | $n\text{-}C_4H_9OH$ | < 1.0% |
|  |  |  |
| Elasthane + PAA | $H_2O$ | 130.0% |
| Elasthane + PAA | $CH_3OH$ | 69.7% |
| Elasthane + PAA | $CH_3COOH$ | 65.3% |
| Elasthane + PAA | $CH_3CH_2OH$ | 62.5% |
| Elasthane + PAA | $CH_2Cl_2$ | 60.4% |
| Elasthane + PAA | $OC(CH_3)_2$ | 49.0% |
| Elasthane + PAA | $CH_3COOCH_2CH_3$ | 20.2% |
| Elasthane + PAA | $n\text{-}C_4H_9OH$ | 3.4% |

| HYDROPHOBIC POLYMER | MODIFICATIONS TO HYDROPHOBIC POLYMER | MONOMER | CO-MONOMER | SOLVENT | CROSSLINKER | INITIATOR (CURING METHOD) |
|---|---|---|---|---|---|---|
| Polyether urethanes | | | | | | |
| Elasthane™ 55D | | 70% acrylic acid | | $H_2O$ | 0.1% MBAA | 0.1% HMPP (UV) |
| Elasthane™ 55D | | 70% acrylic acid | | $H_2O$ | 0.1% MBAA | 0.1% potassium persulfate (thermal) |
| Elasthane™ 55D | | 70% acrylic acid | | $H_2O$ | 0.1% MBAA | 0.1% AIBN (thermal) |
| Elasthane™ 55D | | 70% acrylic acid | | $H_2O$ | 0.01% MBAA | 0.1% HMPP (UV) |
| Elasthane™ 55D | | 70% acrylic acid | | $H_2O$ | none | 0.1% HMPP (UV) |
| Elasthane™ 55D | | 70% acrylic acid | | $H_2O$ | 0.1% TEGMDA | 0.1% HMPP (UV) |
| Elasthane™ 55D | | 100% acrylic acid | | none | 0.1% MBAA | 0.1% HMPP (UV) |
| Elasthane™ 55D | | 85% acrylic acid | | $H_2O$ | 0.1% MBAA | 0.1% HMPP (UV) |
| Elasthane™ 55D | | 60% acrylic acid | | $H_2O$ | 0.1% MBAA | 0.1% HMPP (UV) |
| Elasthane™ 55D | | 50% acrylic acid | | $H_2O$ | 0.1% MBAA | 0.1% HMPP (UV) |
| Elasthane™ 55D | | 40% acrylic acid | | $H_2O$ | 0.1% MBAA | 0.1% HMPP (UV) |
| Elasthane™ 55D | | 30% acrylic acid | | $H_2O$ | 0.1% MBAA | 0.1% HMPP (UV) |
| Elasthane™ 55D | | 15% acrylic acid | | $H_2O$ | 0.1% MBAA | 0.1% HMPP (UV) |
| Elasthane™ 55D | | 10% acrylic acid | | $H_2O$ | 0.1% MBAA | 0.1% HMPP (UV) |
| Elasthane™ 55D | | 70% acrylic acid | | acetic acid | 0.1% MBAA | 0.1% HMPP (UV) |
| Elasthane™ 55D | | 50% acrylic acid | | acetic acid | 0.1% MBAA | 0.1% HMPP (UV) |
| Elasthane™ 55D | | 30% acrylic acid | | acetic acid | 0.1% MBAA | 0.1% HMPP (UV) |
| Elasthane™ 55D | | 10% acrylic acid | | acetic acid | 0.1% MBAA | 0.1% HMPP (UV) |
| Elasthane™ 55D | | 35% acrylamido methyl propyl sulfonic acid | 35% acrylic acid | $H_2O$ | 0.1% MBAA | 0.1% HMPP (UV) |
| Elasthane™ 55D | | 35% vinyl sulfonic acid | 35% acrylic acid | $H_2O$ | 0.1% MBAA | 0.1% HMPP (UV) |
| Elasthane™ 55D | | 35% vinyl sulfonic acid | 35% acrylic acid | $H_2O$ | 0.1% MBAA | 0.1% ammonium persulfate (thermal) |
| Elasthane™ 55D | | 35% sulfopropyl methacrylate | 35% acrylic acid | $H_2O$ | 0.1% MBAA | 0.1% HMPP (UV) |
| Elasthane™ 55D | | 35% sulfopropyl methacrylate | | acetic acid | 0.1% MBAA | 0.1% HMPP (UV) |
| Elasthane™ 55D | | 35% acrylamido methyl propyl sulfonic acid | | acetic acid | 0.1% MBAA | 0.1% HMPP (UV) |
| Elasthane™ 55D | | 35% N-vinyl pyrrolidone | 35% acrylic acid | $H_2O$ | 0.1% MBAA | 0.1% HMPP (UV) |

FIG. 54 (CONT.)

| HYDROPHOBIC POLYMER | MODIFICATIONS TO HYDROPHOBIC POLYMER | MONOMER | CO-MONOMER | SOLVENT | CROSSLINKER | INITIATOR (CURING METHOD) |
|---|---|---|---|---|---|---|
| Polyether urethanes | | | | | | |
| Elasthane™ 55D | | 35% 2-hydroxyethyl acrylate | 35% acrylic acid | $H_2O$ | 0.1% MBAA | 0.1% HMPP (UV) |
| Elasthane™ 55D | | 10% acrylamide | 50% acrylic acid | $H_2O$ | 0.1% MBAA | 0.1% HMPP (UV) |
| Elasthane™ 55D | | 70% acrylic acid | 0.5% methacryloxy-Vitamin C | $H_2O$ | 0.1% MBAA | 0.1% HMPP (UV) |
| Elasthane™ 55D | 1% Vitamin E | 70% acrylic acid | | $H_2O$ | 0.1% MBAA | 0.1% HMPP (UV) |
| Elasthane™ 55D | 0.25% Vitamin E | 70% acrylic acid | | $H_2O$ | 0.1% MBAA | 0.1% HMPP (UV) |
| Elasthane™ 55D | 1% methacryloxy-Vitamin E end groups | 70% acrylic acid | | $H_2O$ | 0.1% MBAA | 0.1% HMPP (UV) |
| Elasthane™ 55D | crosslinked via 1% dihydroxybutene chain extender | 70% acrylic acid | | $H_2O$ | 0.1% MBAA | 0.1% HMPP (UV) |
| Elasthane™ 55D | crosslinked via 5% dihydroxybutene chain extender | 70% acrylic acid | | $H_2O$ | 0.1% MBAA | 0.1% HMPP (UV) |
| Elasthane™ 55D | crosslinked via 1% glycerol methacrylate chain extender | 70% acrylic acid | | $H_2O$ | 0.1% MBAA | 0.1% HMPP (UV) |
| Elasthane™ 55D | crosslinked via 5% glycerol methacrylate chain extender | 70% acrylic acid | | $H_2O$ | 0.1% MBAA | 0.1% HMPP (UV) |
| Elasthane™ 55D | crosslinked via dimethacrylate end groups | 70% acrylic acid | | $H_2O$ | 0.1% MBAA | 0.1% HMPP (UV) |
| Elasthane™ 55D | crosslinked via diacrylamide end groups | 70% acrylic acid | | $H_2O$ | 0.1% MBAA | 0.1% HMPP (UV) |
| Elasthane™ 55D | blend of thermoplastic and diacrylamide-crosslinked polymer | 70% acrylic acid | | $H_2O$ | 0.1% MBAA | 0.1% HMPP (UV) |
| Elasthane™ 55D | partially crosslinked via methacrylate end groups | 70% acrylic acid | | $H_2O$ | 0.1% MBAA | 0.1% HMPP (UV) |
| Elasthane™ 55D | partially crosslinked via acrylamide end groups | 70% acrylic acid | | $H_2O$ | 0.1% MBAA | 0.1% HMPP (UV) |

FIG. 54 (CONT.)

| HYDROPHOBIC POLYMER | MODIFICATIONS TO HYDROPHOBIC POLYMER | MONOMER | CO-MONOMER | SOLVENT | CROSSLINKER | INITIATOR (CURING METHOD) |
|---|---|---|---|---|---|---|
| Polyether urethanes | | | | | | |
| Elasthane™ 75D | | 70% acrylic acid | | $H_2O$ | 0.1% MBAA | 0.1% HMPP (UV) |
| Elasthane™ 80A | | 70% acrylic acid | | $H_2O$ | 0.1% MBAA | 0.1% HMPP (UV) |
| Elasthane™ 90A | | 70% acrylic acid | | $H_2O$ | 0.1% MBAA | 0.1% HMPP (UV) |
| Pellethane™ 55D | | 70% acrylic acid | | $H_2O$ | 0.1% MBAA | 0.1% HMPP (UV) |
| Pellethane™ 75D | | 70% acrylic acid | | $H_2O$ | 0.1% MBAA | 0.1% HMPP (UV) |
| | | | | | | |
| Polycarbonate urethanes | | | | | | |
| Bionate® 55D | | 70% acrylic acid | | $H_2O$ | 0.1% MBAA | 0.1% HMPP (UV) |
| Bionate® 55D | | 50% acrylic acid | | $H_2O$ | 0.1% MBAA | 0.1% HMPP (UV) |
| Bionate® 55D | crosslinked via dimethacrylate end groups | 70% acrylic acid | | $H_2O$ | 0.1% MBAA | 0.1% HMPP (UV) |
| Bionate® 55D | crosslinked via diacrylamide end groups | 70% acrylic acid | | $H_2O$ | 0.1% MBAA | 0.1% HMPP (UV) |
| Bionate® 55D | partially crosslinked via methacrylate end groups | 70% acrylic acid | | $H_2O$ | 0.1% MBAA | 0.1% HMPP (UV) |
| Bionate® 55D | partially crosslinked via acrylamide end groups | 70% acrylic acid | | $H_2O$ | 0.1% MBAA | 0.1% HMPP (UV) |
| Bionate® 90A | | 70% acrylic acid | | $H_2O$ | 0.1% MBAA | 0.1% HMPP (UV) |
| Bionate® 80A | | 70% acrylic acid | | $H_2O$ | 0.1% MBAA | 0.1% HMPP (UV) |
| Bionate® II 55D | | 70% acrylic acid | | $H_2O$ | 0.1% MBAA | 0.1% HMPP (UV) |
| Bionate® 75D | | 70% acrylic acid | | $H_2O$ | 0.1% MBAA | 0.1% HMPP (UV) |
| | | | | | | |
| Silicon-based polyurethanes | | | | | | |
| CarboSil® 55D | | 70% acrylic acid | | $H_2O$ | 0.1% MBAA | 0.1% HMPP (UV) |
| CarboSil® 80A | | 70% acrylic acid | | $H_2O$ | 0.1% MBAA | 0.1% HMPP (UV) |
| PurSil® 55D | | 70% acrylic acid | | $H_2O$ | 0.1% MBAA | 0.1% HMPP (UV) |
| PurSil® 80A | | 70% acrylic acid | | $H_2O$ | 0.1% MBAA | 0.1% HMPP (UV) |
| | | | | | | |
| Polyurethane urea | | | | | | |
| BioSpan® | | 70% acrylic acid | | $H_2O$ | 0.1% MBAA | 0.1% HMPP (UV) |

FIG. 54 (CONT.)

| HYDROPHOBIC POLYMER | MODIFICATIONS TO HYDROPHOBIC POLYMER | MONOMER | CO-MONOMER | SOLVENT | CROSSLINKER | INITIATOR (CURING METHOD) |
|---|---|---|---|---|---|---|
| Polyurethane urea | | | | | | |
| BioSpan® | | 20% acrylic acid | | $H_2O$ | 0.1% MBAA | 0.1% HMPP (UV) |
| BioSpan® | crosslinked via dimethacrylate end groups | 70% acrylic acid | | $H_2O$ | 0.1% MBAA | 0.1% HMPP (UV) |
| BioSpan® | crosslinked diacrylamide end groups | 70% acrylic acid | | $H_2O$ | 0.1% MBAA | 0.1% HMPP (UV) |
| BioSpan® | partially crosslinked via methacrylate end groups | 70% acrylic acid | | $H_2O$ | 0.1% MBAA | 0.1% HMPP (UV) |
| BioSpan® | partially crosslinked via acrylamide end groups | 70% acrylic acid | | $H_2O$ | 0.1% MBAA | 0.1% HMPP (UV) |
| | | | | | | |
| Other polymers | | | | | | |
| Acrylonitrile Butadiene Styrene | | 100% acrylic acid | | none | 0.1% MBAA | 0.1% HMPP (UV) |
| Acrylonitrile Butadiene Styrene | | 100% acrylic acid | | none | 0.1% MBAA | 0.1% HMPP (UV) |
| Acrylonitrile Butadiene Styrene | | 100% acrylic acid | | none | 0.1% MBAA | 0.1% HMPP (UV) |
| Poly(methyl methacrylate) | | 100% acrylic acid | | none | 0.1% MBAA | 0.1% HMPP (UV) |
| Polyaryletheretherketone (PEEK) | | 50% acrylic acid | | DMAC | 0.1% MBAA | 0.1% HMPP (UV) |
| Polydimethyl siloxane (PDMS) | | 50% acrylic acid | | THF | 0.1% MBAA | 0.1% HMPP (UV) |

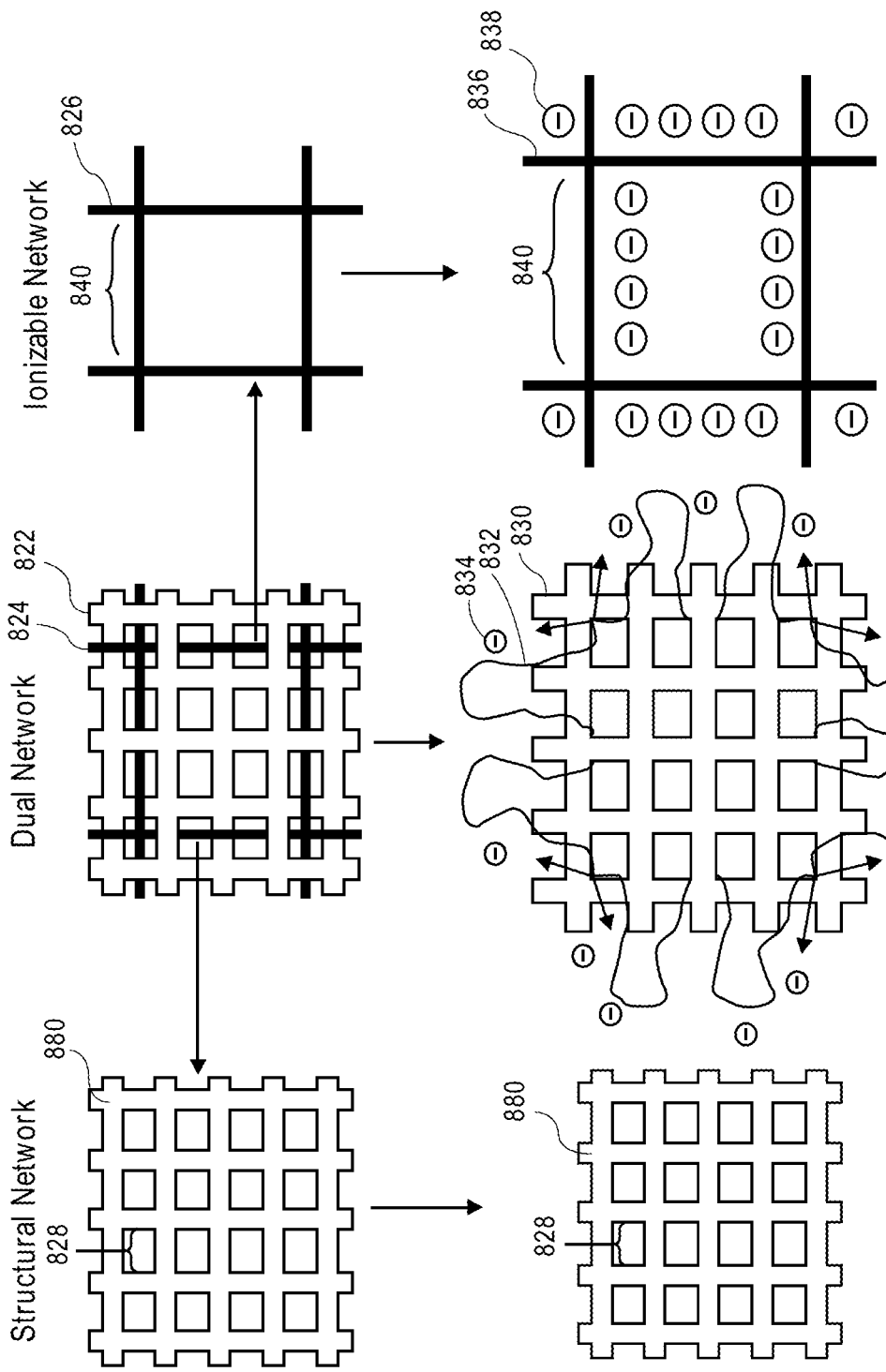

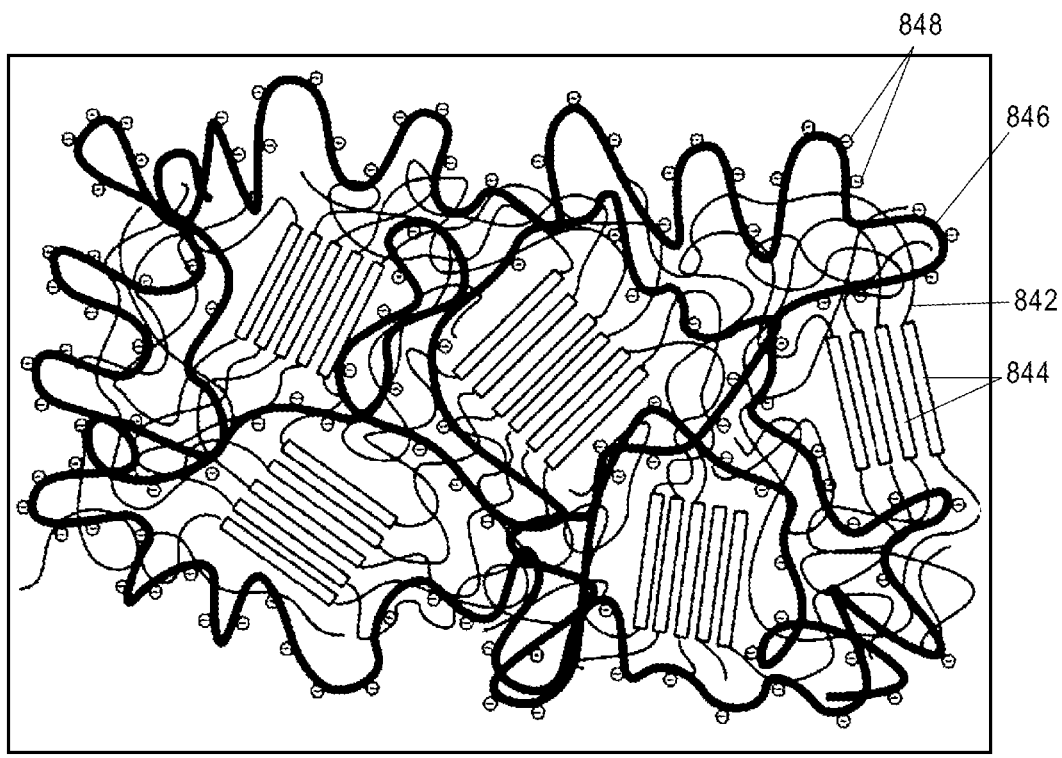
FIG. 73
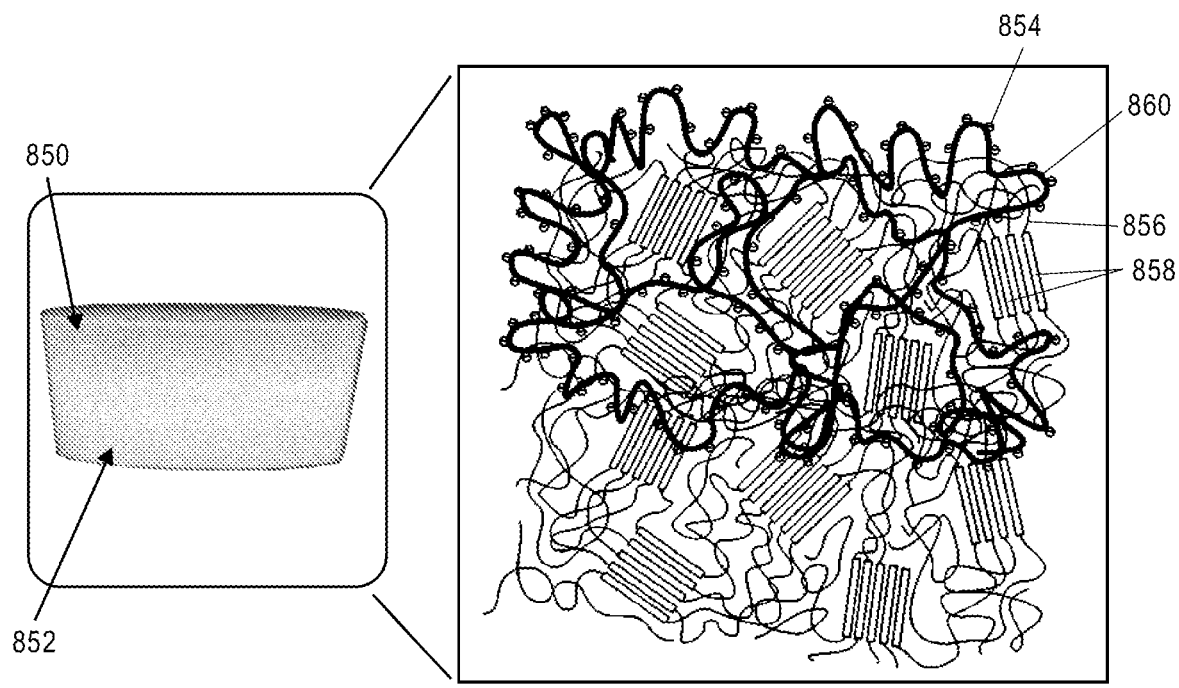
FIG. 74A  FIG. 74B

| Starting polyurethane | % Acrylic acid | % PU | % PAA | % PAA⁻ | % Na⁺ counterion of PAA | % H₂O | % Salts |
|---|---|---|---|---|---|---|---|
| E80A | 30% | 100.00% | 4.34% | 38.50% | 12.47% | 179.43% | 5.41% |
| E80A | 40% | 100.00% | 5.91% | 52.47% | 17.00% | 253.61% | 6.27% |
| E80A | 50% | 100.00% | 7.78% | 69.04% | 22.37% | 370.15% | 9.25% |
| E80A | 60% | 100.00% | 11.27% | 100.00% | 32.39% | 601.32% | 17.00% |
| E80A | 65% | 100.00% | 14.53% | 128.96% | 41.78% | 862.86% | 24.84% |
| E55D | 40% | 100.00% | 3.57% | 31.69% | 10.27% | 104.79% | 2.77% |
| E55D | 50% | 100.00% | 4.29% | 38.11% | 12.35% | 129.96% | 3.90% |
| E55D | 60% | 100.00% | 5.53% | 49.11% | 15.91% | 171.12% | 6.65% |
| E55D | 65% | 100.00% | 6.37% | 56.53% | 18.31% | 198.71% | 9.34% |
| E55D | 70% | 100.00% | 7.45% | 66.13% | 21.42% | 238.71% | 10.68% |
| E55D | 75% | 100.00% | 9.15% | 81.18% | 26.30% | 303.30% | 10.84% |
| E55D | 80% | 100.00% | 11.23% | 99.67% | 32.29% | 387.86% | 11.17% |
| E65D | 50% | 100.00% | 3.05% | 27.09% | 8.78% | 83.06% | 5.19% |
| E65D | 60% | 100.00% | 3.91% | 34.66% | 11.23% | 106.68% | 6.66% |
| E65D | 65% | 100.00% | 4.48% | 39.80% | 12.89% | 128.16% | 7.46% |
| E65D | 70% | 100.00% | 5.49% | 48.73% | 15.79% | 160.76% | 9.62% |
| E65D | 75% | 100.00% | 6.82% | 60.55% | 19.61% | 211.41% | 10.66% |
| E65D | 80% | 100.00% | 8.06% | 71.52% | 23.17% | 253.09% | 13.20% |
| E75D | 50% | 100.00% | 2.38% | 21.08% | 6.83% | 60.67% | 1.65% |
| E75D | 60% | 100.00% | 3.02% | 26.78% | 8.68% | 77.31% | 3.20% |
| E75D | 65% | 100.00% | 3.44% | 30.57% | 9.90% | 89.94% | 4.93% |
| E75D | 70% | 100.00% | 4.02% | 35.71% | 11.57% | 109.20% | 5.78% |
| E75D | 75% | 100.00% | 4.97% | 44.09% | 14.28% | 139.53% | 5.86% |
| E75D | 80% | 100.00% | 5.83% | 51.71% | 16.75% | 170.08% | 5.26% |

FIG. 75

| Starting polyurethane | % Acrylic acid | % PU | % PAA | % PAA⁻ | % Na⁺ counterion of PAA | % H$_2$O | % Salts |
|---|---|---|---|---|---|---|---|
| E75D | 50% | 51.92% | 1.23% | 10.94% | 3.55% | 31.50% | 0.86% |
| E75D | 60% | 45.66% | 1.38% | 12.23% | 3.96% | 35.30% | 1.46% |
| E65D | 50% | 44.02% | 1.34% | 11.93% | 3.86% | 36.56% | 2.28% |
| E75D | 65% | 41.88% | 1.44% | 12.80% | 4.15% | 37.67% | 2.06% |
| E65D | 60% | 38.00% | 1.48% | 13.17% | 4.27% | 40.54% | 2.53% |
| E75D | 70% | 37.55% | 1.51% | 13.41% | 4.34% | 41.01% | 2.17% |
| E55D | 40% | 39.51% | 1.41% | 12.52% | 4.06% | 41.40% | 1.09% |
| E65D | 65% | 34.15% | 1.53% | 13.59% | 4.40% | 43.77% | 2.55% |
| E55D | 50% | 34.65% | 1.49% | 13.21% | 4.28% | 45.03% | 1.35% |
| E75D | 75% | 32.39% | 1.61% | 14.28% | 4.63% | 45.19% | 1.90% |
| E65D | 70% | 29.38% | 1.61% | 14.32% | 4.64% | 47.23% | 2.83% |
| E75D | 80% | 28.60% | 1.67% | 14.79% | 4.79% | 48.64% | 1.51% |
| E55D | 60% | 28.71% | 1.59% | 14.10% | 4.57% | 49.13% | 1.91% |
| E55D | 65% | 25.69% | 1.64% | 14.52% | 4.70% | 51.05% | 2.40% |
| E65D | 75% | 24.45% | 1.67% | 14.80% | 4.79% | 51.68% | 2.61% |
| E80A | 30% | 29.40% | 1.28% | 11.32% | 3.67% | 52.75% | 1.59% |
| E55D | 70% | 22.50% | 1.68% | 14.88% | 4.82% | 53.72% | 2.40% |
| E65D | 80% | 21.32% | 1.72% | 15.25% | 4.94% | 53.96% | 2.81% |
| E55D | 75% | 18.84% | 1.72% | 15.29% | 4.95% | 57.14% | 2.04% |
| E80A | 40% | 22.97% | 1.36% | 12.06% | 3.91% | 58.27% | 1.44% |
| E55D | 80% | 15.57% | 1.75% | 15.52% | 5.03% | 60.39% | 1.74% |
| E80A | 50% | 17.28% | 1.34% | 11.93% | 3.87% | 63.97% | 1.60% |
| E80A | 60% | 11.60% | 1.31% | 11.60% | 3.76% | 69.76% | 1.97% |
| E80A | 65% | 8.53% | 1.24% | 10.99% | 3.56% | 73.56% | 2.12% |

FIG. 77

ORTHOPEDIC IMPLANTS HAVING GRADIENT POLYMER ALLOYS

CROSS REFERENCE TO RELATED APPLICATIONS

This application is a continuation of U.S. patent application Ser. No. 16/579,375 filed Sep. 23, 2019, which is a continuation of U.S. patent application Ser. No. 15/394,297 filed Dec. 29, 2016, now U.S. Pat. No. 10,457,803, which is a continuation of U.S. patent application Ser. No. 13/347,647 filed Jan. 10, 2012, now abandoned, which is a continuation-in-part of U.S. patent application Ser. No. 13/219,348 filed Aug. 26, 2011, now U.S. Pat. No. 8,883,915, which claims the benefit of U.S. Provisional Application No. 61/377,844, filed Aug. 27, 2010 and of U.S. Provisional Application No. 61/383,705, filed Sep. 16, 2010. U.S. patent application Ser. No. 13/219,348 is a continuation-in-part of U.S. patent application Ser. No. 12/499,041, filed Jul. 7, 2009, now abandoned, which claims the benefit U.S. Provisional Application No. 61/078,741, filed Jul. 7, 2008, U.S. Provisional Application No. 61/079,060, filed Jul. 8, 2008, U.S. Provisional Application No. 61/095,273, filed Sep. 8, 2008, and U.S. Provisional Application No. 61/166,194, filed Apr. 2, 2009. U.S. patent application Ser. No. 13/347,647 also claims the benefit under 35 U.S.C. 119 of U.S. Provisional Patent Application No. 61/431,327, filed Jan. 10, 2011, U.S. Provisional Patent Application No. 61/454,957, filed Mar. 21, 2011, and U.S. Provisional Patent Application No. 61/566,567, filed Dec. 2, 2011; the disclosures of each of these prior applications is incorporated herein by reference.

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

The present invention pertains to semi- and fully interpenetrating polymer networks, methods of making semi- and fully interpenetrating polymer networks, articles useful in orthopedics made from such semi- and fully interpenetrating polymer networks, and methods of using such articles.

BACKGROUND OF THE INVENTION

Fully interpenetrating polymer networks (IPN's) and semi-interpenetrating polymer networks ("semi-IPN's") have been created from a variety of starting materials and have been used for a variety of applications. IPN's and semi-IPNs can combine the beneficial properties of the polymers from which they are made and can avoid some of the undesirable properties of their component polymers.

Prior IPN's and semi-IPNs have been proposed for use in biomedical applications, such as a coating for an implant or as artificial cartilage. See, e.g., U.S. Patent Publ. No. 2005/0147685; U.S. Patent Publ. No. 2009/0035344; and U.S. Patent Publ. No. 2009/008846. The utility of prior IPNs and semi-IPNs for their proposed applications is limited by the properties of those compositions, however. In addition, the starting materials and processes of making such prior compositions limit not only the resulting properties of the IPN or semi-IPN but also the commercial viability of the manufacturing processes and the articles made in such processes. Also, the mechanical properties of prior IPNs and semi-IPNs are often limited by the mechanical properties of the component polymers used, which in the case of most intrinsically hydrophilic, water-swellable polymers, are usually quite low. For example, the prior art has not described making a water-swellable IPN or semi-IPN from commercially available hydrophobic thermoset or thermoplastic polymers, such as polyurethane or ABS.

Finally, the utility of prior IPN and semi-IPN compositions and the value of the articles formed from such compositions have been limited by the inability to create IPN's and semi-IPNs with desired characteristics, such as strength, lubricity and wear-resistance.

The prior art has also not provided joint implants that fully address the loss of motion and pain experienced by individuals suffering from arthritis or other joint damage. When less invasive methods fail, patients suffering from joint problems can undergo total joint arthroplasty (TJA) or joint resurfacing. The joint is opened, damaged or diseased bone is removed and an implant is laced in the joint. Implants made from metal, ceramic and/or ultra-high molecular weight polyethylene (UHMWPE) have been used in orthopedic joint arthroplasty or joint replacement for a number of years. Surgeons have experience replacing one or both sides of a joint. They can replace both sides with the same material; if the material is metal then a metal-on-metal articulation is created. They can replace each side of the joint with a different material to create a mixed articulation, such as metal-on-polyethylene.

Although a large number of patients undergo joint replacement surgery each year (an estimated 540,000 patients in the U.S. undergo knee arthroplasty annually), metal, ceramic, and UHMWPE implants in joints can cause adverse local and remote tissue responses. The responses may be due to inherent characteristics of the implant, changes in the implant material over time, or release of material from the implant. A prosthetic joint implant experiences significant friction, motion, pressure, and chemical changes over the course of many years. As time goes by, the implant may corrode or may release ions or debris, such as metal ions or wear particles. The ions or particles may remain in the joint area or may travel through the blood to other parts of the body. The implant or the debris or ions it releases may cause bone resorption (osteolysis), inflammation, metal toxicity, pseudo-tumors, pain, and other problems. In some cases, the implant may loosen and require replacement, using a procedure called revision surgery. In revision surgery, the old, unwanted implant is removed, additional damaged or diseased joint and/or bone material is removed to create a clean, strong surface for attaching the implant, and a new implant is placed. Revision surgeries are expensive, painful, sometimes result in dangerous and hard-to-treat infections, and require long recovery and rehabilitation time.

More recently, hydrogel polymers have been suggested for use in joint implants as alternatives to the metal, ceramic, and UHMWPE implants. U.S. 2004/0199250 by Fell describes a knee prosthesis with a hydrogel coating portion and a high modulus supporting portion for placement into a body joint without requiring bone resection. U.S. 2006/0224244 to Thomas et al. describes a hydrogel implant for replacing a portion of a skeletal joint. The implant has a hydrogel bearing surface with high water content and lower strength and rigidity mounted to a support substrate. U.S.

2008/0241214 to Myung et al. describes the attachment of a hydro gel polymer to a metal assembly. The surface of the metal assembly is modified using an inorganic material and the hydrogel polymer is attached using an intervening polymer network. The assembly may be used as an orthopedic implant. These hydrogel polymers, however, do not perfectly recreate the original anatomy, shape, or strength of the joint.

What are needed are materials and methods which overcome the above and other disadvantages of known joint replacement or joint resurfacing implants and procedures.

SUMMARY OF THE INVENTION

The mechanical properties desired for certain medical applications are often outside the range of possibility of many hydrophilic starting materials. Hence, one aspect of this invention takes advantage of the high mechanical strength of hydrophobic starting materials and combines those materials with certain ionic polymers as a useful way to achieve the goal of high mechanical strength in addition to other desirable properties. Thus, while the prior art took water-swellable polymers and tried to make them stronger, one aspect of this invention takes strong materials and makes them more water-swellable.

For purposes of this application, an "interpenetrating polymer network" or "IPN" is a material comprising two or more polymer networks which are at least partially interlaced on a molecular scale, but not covalently bonded to each other, and cannot be separated unless chemical bonds are broken. A "semi-interpenetrating polymer network" or "semi-IPN" is a material comprising one or more polymer networks and one or more linear or branched polymers characterized by the penetration on a molecular scale of at least one of the networks by at least some of the linear or branched macromolecules. As distinguished from an IPN, a semi-IPN is a polymer blend in which at least one of the component polymer networks is not chemically crosslinked by covalent bonds.

A "polymer" is a substance comprising macromolecules, including homopolymers (a polymer derived one species of monomer) and copolymers (a polymer derived from more than one species of monomer). A "hydrophobic polymer" is a pre-formed polymer network having at least one of the following two properties: (1) a surface water contact angle of at least 45° and (2) exhibits water absorption of 2.5% or less after 24 hours at room temperature according to ASTM test standard D570. A "hydrophilic polymer" is a polymer network having a surface water contact angle less than 45° and exhibits water absorption of more than 2.5% after 24 hours at room temperature according to ASTM test standard D570. An "ionic polymer" is defined as a polymer comprised of macromolecules containing at least 2% by weight ionic or ionizable monomers (or both), irrespective of their nature and location. An "ionizable monomer" is a small molecule that can be chemically bonded to other monomers to form a polymer and which also has the ability to become negatively charged due the presence of acid functional groups such carboxylic acid and/or sulfonic acid. A "thermoset polymer" is one that does not melt when heated, unlike a thermoplastic polymer. Thermoset polymers "set" into a given shape when first made and afterwards do not flow or melt, but rather decompose upon heating and are often highly crosslinked and/or covalently crosslinked. A "thermoplastic polymer" is one which melts or flows when heated, unlike thermoset polymers. Thermoplastic polymers are usually not covalently crosslinked. A "polymer alloy" is an IPN or semi-IPN. A "gradient polymer alloy" is a gradient IPN or semi-IPN (e.g. an IPN or semi-IPN having a compositional gradient). "Phase separation" is defined as the conversion of a single phase system into a multi-phase system; especially the separation of two immiscible blocks of a block copolymer into two phases, with the possibility of a small interphase in which a small degree of mixing occurs. The present invention includes a process for modifying common commercially available hydrophobic thermoset or thermoplastic polymers, such as polyurethane or ABS to provide new properties, such as strength, lubricity, electrical conductivity and wear-resistance. Other possible hydrophobic thermoset or thermoplastic polymers are described below. The invention also includes the IPN and semi-IPN compositions as well as articles made from such compositions and methods of using such articles. The IPN and semi-IPN compositions of this invention may attain one or more of the following characteristics: High tensile and compressive strength; low coefficient of friction; high water content and swellability; high permeability; biocompatibility; and biostability.

One aspect of the invention provides an orthopedic implant, e.g. adapted to fit an acromioclavicular joint, an ankle joint, a condyle, an elbow joint, a finger joint, a glenoid, a hip joint, an intervertebral disc, an intervertebral facet joint, a labrum, a meniscus, a metacarpal joint, a metatarsal joint, a patella, a tibial plateau, a toe joint, a temporomandibular joint, or a wrist joint, including a bone interface member having a bone contact surface and a water swellable IPN or semi-IPN member having a bearing surface and an attachment zone, the attachment zone being attached to the bone interface member, the water swellable IPN or semi-IPN member comprising a hydrophobic thermoset or thermoplastic polymer first network and an ionic polymer second network configured to exhibit a compositional gradient between the bearing surface and the attachment zone. In some embodiments, the implant the compositional gradient forms a stiffness gradient. In some embodiments, one of the networks forms a hydration gradient from a first portion of the implant to a second portion of the implant.

In some embodiments, the bone interface member includes metal (e.g. porous metal). In some embodiments, the bone interface member includes a ceramic or polymer. In some embodiments, at least a portion of the orthopedic joint is configured to change a shape or to transiently bend during implant placement in a joint.

In some embodiments, in which the first network includes a polyurethane, the implant includes a chemical linkage between the IPN or semi-IPN member and the bone interfacing member (e.g. a urethane linkage). In some embodiments, an attachment of the attachment zone to the bone interface member is created by an adhesive.

In some embodiments, the ionic polymer second network has a fixed charge, and may further include carboxylic acid and/or sulfonic acid groups.

In some embodiments a thickness of the IPN or semi-IPN is less than 5 mm in a thickest region.

In some embodiments, the implant may further include a synthetic joint capsule and may include fluid. In some embodiments, the implant may further include a labral component. In some embodiments, the implant may have a shape of a cap, a cup, a plug, a mushroom, a patch and/or a stem.

Yet another aspect of the invention provides an orthopedic implant system including a first medical implant including a water-swellable IPN or semi-IPN including a hydrophobic thermoset or thermoplastic polymer and an ionic polymer, the first medical implant have a bone contact surface configured to conform to a bone surface and a bearing surface adapted to mate with a bearing surface of another implant or a natural joint and a joint capsule configured to enclose the bearing surface. In some embodiments, the joint capsule includes a fluid.

In some embodiments, the system further includes a second medical implant including a water swellable IPN or semi-IPN including a hydrophobic thermoset or thermoplastic polymer and an ionic polymer, the second medical implant having a bone contact surface configured to conform to a bone surface and a bearing surface, and the first medical implant may be configured for placement in one side of a joint, the second medical implant is configured for placement on a second side of the joint and the bearing surfaces of the first and second medical implants are configured to mate, and the joint capsule may be configured to enclose the bearing surfaces of the first and the second medical implants.

In some embodiments, the orthopedic implant system further includes a bone interface member physically attached to the IPN or semi-IPN, and the bone interface member includes the bone contact surface and may be metal.

Yet another aspect of the invention provides a hip joint implant including a water-swellable IPN or semi-IPN including a hydrophobic thermoset or thermoplastic polymer and an ionic polymer, the implant having a bone contact surface configured to conform to a bone surface and a bearing surface, and a labral component configured to enclose the bearing surface.

In some embodiments, the hip joint implant further includes a joint capsule including fluid and configured to enclose the bearing surface.

Yet another aspect of the invention provides a composition of matter including a polyurethane-polyacrylic acid IPN or semi-IPN including about 4% to about 90% (w/w) polyurethane, about 1% to about 40% (w/w) electrolyte of polyacrylic acid, and about 3% to about 80% water when analyzed at pH 7.4, 37° C., in a 0.9% aqueous salt solution. In some embodiments, the concentration of polyurethane is from about 8% to about 55%, the composition of an electrolyte of polyacrylic acid is from about 9% to about 22%, and/or a concentration of water is from about 25% to about 80%.

Yet another aspect of the invention provides an orthopedic implant including a water swellable IPN or semi-IPN having a bearing surface and an attachment surface and including a hydrophobic thermoset or thermoplastic polymer first network and an ionic polymer second network, the bearing surface having a coefficient of friction between 0.001 and 0.1, an equilibrium compressive elastic modulus between 0.8 and 200 MPa, a water content between 25% and 80%, a hydraulic permeability greater than $10^{17}$ m$^4$/N sec, and a failure tensile strain greater than 10%. In some embodiments, the orthopedic implant has a failure tensile strain greater than 50%.

Yet another aspect of the invention provides an orthopedic implant including a polymer bearing member including a bearing surface and an attachment zone (e.g. a feature such as a cone, a depression, a groove, a peg, a pillar, a pin, and a pyramid), and a bone interface member attached to the attachment zone of the polymer bearing member and including metal and open spaces in the metal, the orthopedic implant being deformable from a first shape to a second shape to conform a bone interface member to a bone surface.

In some embodiments, the open spaces in the orthopedic implant includes pores or slots in the metal. In some embodiments, the orthopedic implant includes a plurality of metal members attached to the attachment surface and separated from each other.

In some embodiments, the bone interface member is physically attached to the' polymer bearing member, such as by a chemical linkage between the polymer bearing member and the bone interfacing member. In some embodiments, an attachment of the attachment zone to the bone interface member is created by an adhesive.

In some embodiments, the polymer bearing member includes a water swellable IPN or semi-IPN, and may include a hydrophobic thermoset or thermoplastic polymer first network and an ionic polymer second network.

Yet another aspect of the invention includes a method of inserting an orthopedic implant into a joint, the implant including a metal portion and a flexible polymer portion having an attachment zone and a bearing surface, the metal portion attached to the attachment zone, the method includes the steps of inserting the implant in a first shape into the joint and changing the implant from the first shape to a second shape to conform to a shape of at least a portion of a bone forming the joint. In some embodiments, the method further includes the step of changing the implant from the second shape back to the first shape after the first changing step. In other embodiments, the method includes the step of deforming the implant from an original shape to the first shape prior to the changing step. In some embodiments in which the joint is a hip joint and the implant is configured for placement on a femoral head of a hip joint, deforming includes expanding a portion of the implant to fit over the femoral head.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 4B illustrates variation of gradient properties within an IPN according to the invention.

FIG. 4C illustrates the variation of an ionic polymer across a gradient IPN.

FIGS. 6A and 6B illustrate shaping of a gradient IPN article.

FIGS. 7A-D illustrate shape heating of an IPN.

FIGS. 8A-D illustrate bonding of a gradient IPN article to a surface.

FIGS. 10A-B illustrate an osteochondral graft having an opening to accommodate a ligament.

FIGS. 11A-E show osteochondral grafts formed from an IPN or semi-IPN of this invention that may be used singly or in any combination needed to replace or augment cartilage within a knee joint.

FIGS. 12A-B show osteochondral grafts formed from the IPN's or semi-IPN's of this invention and shaped for use in a finger joint.

FIGS. 13A-B show a labrum prosthesis formed from an IPN or semi-IPN of this invention for use in replacing or resurfacing the labrum of the shoulder or hip.

FIG. 14 shows the use of an IPN or semi-IPN of this invention as a bursa osteochondral graft, labrum osteochondral graft, glenoid osteochondral graft and humeral head osteochondral graft.

FIG. 15 shows the use of an IPN or semi-IPN of this invention as prostheses for resurfacing intervertebral facets.

FIG. 16A shows a prosthetic cartilage plug formed from a gradient IPN composition of this invention.

FIGS. 16B-D show embodiments in which porous surfaces are formed on the cartilage plug.

FIG. 16D is a bottom elevational view of the embodiment of FIG. 16C.

FIG. 17 shows an embodiment of a prosthetic cartilage plug in which the stem is provided with helical ridges to form a screw for fixation of the plug to bone.

FIGS. 18A-B are side and bottom elevational views of an embodiment of a prosthetic cartilage plug having three stems for press fit insertion into holes in the bone for fixation.

FIG. 19 shows an embodiment of a prosthetic cartilage plug in which the exposed head portion is substantially the same diameter as the stem.

FIG. 20 shows an embodiment of a prosthetic cartilage plug in which the exposed head portion is narrower than the stem, and the stem widens toward the base.

FIG. 21 shows an embodiment of a prosthetic cartilage plug in which the stem has circumferential ridges to aid fixation.

FIG. 22 shows an embodiment similar to that of FIG. 19 that adds a rough porous surface to the stem.

FIG. 32 shows the use of a lubricious IPN or semi-IPN composition of this invention to resurface the hull of a marine vessel.

FIG. 33 shows the use of a lubricious thermoplastic or thermoset IPN to modify interfacing surfaces of machine parts that move with respect to each other.

FIG. 34 shows the use of a lubricious thermoplastic or thermoset IPN to reduce fluid drag on the inner surface of a pipe.

FIG. 38 shows the PEU/PAA semi-IPN material subject to Transmission Electron Microscopy analysis with a schematic diagram associated with Example 34.

FIG. 41 shows the results of thermal analysis of the PEU/PAA semi-IPN material analyzed by DSC associated with Example 36.

FIGS. 44A-C show the results of wear testing of the PEU/PAA semi-IPN material associated with Example 39 compared to UHMWPE sample from a metal-on-UHMWPE wear test.

FIG. 47 shows the swelling behavior of polyether urethane and PEU/PAA semi-IPN in various aqueous and organic solvents associated with Example 40.

FIG. 54 shows a partial list of materials that have been made in accordance with the present invention.

FIGS. 72A-F show a schematic diagram of an interpenetrating polymer network.

FIG. 73 shows a polyurethane-polyelectrolyte IPN.

FIG. 74A-B show a polyurethane-polyelectrolyte IPN with a stiffness gradient from one side to the other side according to one aspect of the invention.

FIG. 75 shows compositions of polyurethane-polyelectrolyte compositions.

FIG. 77 shows compositions of polyurethane-polyelectrolyte systems produced.

DETAILED DESCRIPTION OF THE INVENTION

Figure 1A:
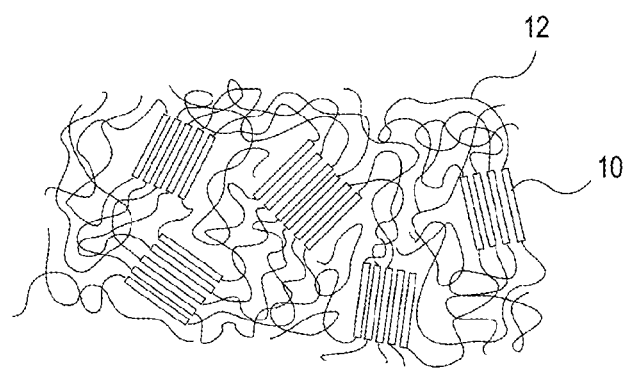
FIGS. 1A-D illustrate a method of forming an IPN or semi-IPN according to one aspect of this invention.

The present invention includes a process for modifying hydrophobic thermoset or thermoplastic polymers to confer upon them qualities such as lubricity, permeability, conductivity and wear-resistance. Such hydrophobic polymers ordinarily do not soak up water to any significant extent and are generally useful for their mechanical strength, impermeability and insulating ability. An exemplary list of common and commercially available hydrophobic polymers modifiable by the process of this invention includes the following: Acrylonitrile butadiene styrene (ABS), Polymethylmethacrylate (PMMA), Acrylic, Celluloid, Cellulose acetate, Ethylene-Vinyl Acetate (EVA), Ethylene vinyl alcohol (EVAL), Kydex, a trademarked acrylic/PVC alloy, Liquid Crystal Polymer (LCP), Polyacetal (POM or Acetal), Polyacrylates (Acrylic), Polyacrylonitrile (PAN or Acrylonitrile), Polyamide (PA or Nylon), Polyamideimide (PAI), Polyaryletherketone (PAEK or Ketone), Polyhydroxyalkanoates (PHAs), Polyketone (PK), Polyester, Polyetheretherketone (PEEK), Polyetherimide (PEI), Polyethersulfone (PES)-see Polysulfone, Polyethylenechlorinates (PEC), Polyimide (PI), Polymethylpentene (PMP), Polyphenylene oxide (PPO), Polyphenylene sulfide (PPS), Polyphthalamide (PPA), Polystyrene (PS), Polysulfone (PSU), Polyvinyl acetate (PVA), Polyvinyl chloride (PVC), Polyvinylidene chloride (PVDC), Spectralon, Styrene-acrylonitrile (SAN), Polydimethylsiloxane (PDMS), and Polyurethanes (PU). Other, less common and non-commercially available (i.e. custom) polymers may also be used. A wide variety of polyurethanes can be used with varying hard segment, soft segment, and chain extender compositions, as will be described herein.

One aspect of the invention takes advantage of a characteristic of some modifiable thermoset or thermoplastic hydrophobic polymers: the presence of ordered and disordered (amorphous) domains within the polymer. For example, some hydrophobic thermoset or thermoplastic polymers such as polyurethanes are phase-separated, containing first domains of hard segments and second domains of soft segments, with the two domains exhibiting different solubility properties with respect to interpenetration of monomers. In polyurethanes, the hard segments are disposed primarily within the ordered domains and the soft segments are disposed primarily within the disordered (amorphous) domains. (The starting polymer may contain more than two domains, of course, without departing from the scope of the invention.) This difference in properties between the two domains of the phase-separated polymer enables the process of this invention to impart new properties to the polymer that can extend throughout the bulk of the material or throughout only a portion of the material, e.g., in a particular region or in a gradient. For example, a non-lubricious polymer can be made lubricious; an otherwise non-conductive polymer can be made conductive; and an otherwise non-permeable polymer can be made permeable. Moreover, the process can be performed repeatedly to introduce more than one new property to the starting polymer.

In some embodiments, phase separation in the polymer allows for differential swelling of one or more separated phases within the polymer with, e.g., a solvent and/or monomer, which is then used to impart new properties. According to the invention, for example, lubriciousness can be introduced to an otherwise non-lubricious material by adding and polymerizing ionic monomers. In one embodiment, a polymer material with high mechanical strength and a lubricious surface can be made from an otherwise non-lubricious, hydrophobic polymer and a hydrophilic polymer derived from ionizable, vinyl monomers. By converting otherwise hydrophobic materials into biphasic materials with both solid and liquid (water) phases, the present invention addresses a need in the art for lubricious, high strength materials for use in medical, commercial, and industrial applications.

Figure 1B:
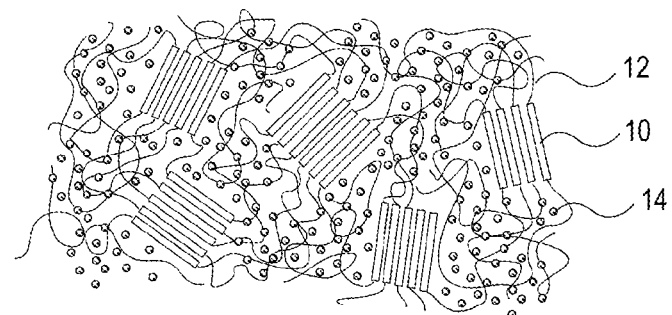
Figure 1C:
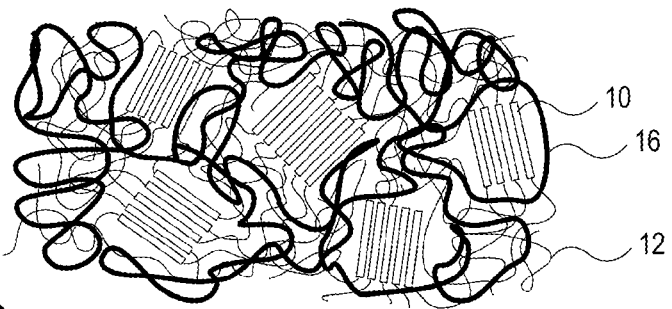

FIGS. 1A-D illustrate the process with respect to a thermoplastic polyurethane-based polymer containing a network of hard segments 10 (shown as open rectangles) and soft segments 12 (shown as lines). In FIG. 1B, the soft segments 12 are swollen with vinyl-based monomer 14 (shown as circles) and optional solvent, along with an initiator and cross-linker (not shown), while mostly not affecting the hard segment material. This swelling process is not dissolution of the polymer; the hard segments act as physical crosslinks to hold the material together as the soft segments are imbibed with the monomer(s) and optional solvent(s). After polymerization and cross-linking of the monomers, a second network 16 (shown as dark lines in FIGS. 1C and 1D) is formed in the presence of the first network to create an IPN in which the second polymer (i.e., the polymerized monomer) is primarily sequestered within the soft, amorphous domain of the first polymer. Despite some degree of molecular rearrangement and further phase separation, the hard segments largely remain ordered and crystalline, providing structure and strength to the material.

Figure 1D:
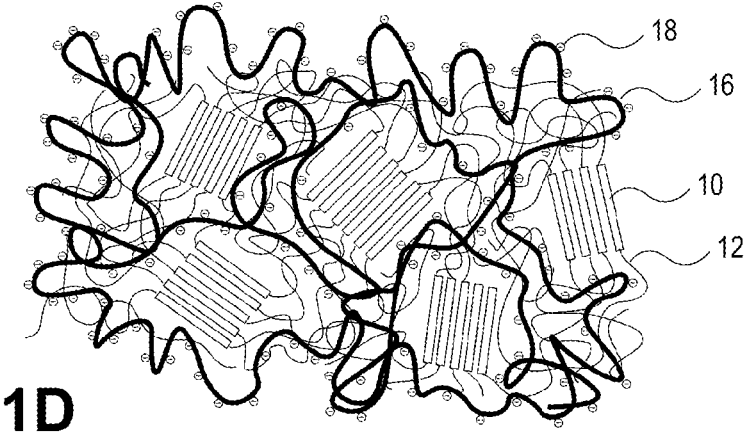

The new properties provided by this IPN depend on the properties of the polymerized monomers that were introduced and on any optional post-polymerization processing. Examples of such new properties include lubriciousness, conductivity, hardness, absorbency, permeability, photoreactivity and thermal reactivity. For example, as shown in FIG. 1D, after optional swelling in a buffered aqueous solution, the second network of the IPN of FIG. 1C becomes ionized 18, and the IPN is water-swollen and lubricious. Thus, hydrophilicity (i.e., water absorbency) can be introduced into an otherwise hydrophobic material. A hydrophobic polymer material such as polyurethane or ABS can be infiltrated with various ionic polymers such as polyacrylic acid and/or poly(sulfopropyl methacrylate) such that it absorbs water.

In addition to absorbency, various levels of permeability (water, ion, and/or solute transport) can be introduced into an otherwise non-permeable material. For example, a hydrophobic polymer material such as polyurethane or ABS can be infiltrated with an ionic polymer such as polyacrylic acid and/or poly(sulfopropyl methacrylate) so that it absorbs water, as described above. This hydration of the bulk of the material allows for the transport of solutes and ions. The transport of solutes and ions and permeability to water is made possible by phase continuity of the hydrated phase of the IPN. This is useful in various applications, including drug delivery, separation processes, proton exchange membranes, and catalytic processes. The permeability can also be utilized to capture, filter, or chelate solutes as a liquid flows over or through the material. Furthermore, because of this permeability, the materials of the present invention can be bestowed with increased resistance to creep and fatigue relative to their component hydrophobic polymers due to their ability to re-absorb fluid after sustained or repetitive loading.

Conductivity can be introduced into an otherwise non-conductive material. For example, an insulating polymer material such as polyurethane can be infiltrated with a conductive polymer (a polyelectrolyte) so that at least part of the hybrid material is conductive to electric current.

The invention also includes the alteration of chemical groups of the second polymer and the use of tethering points in the second polymer for another polymer, molecule or biomolecule. Also, any of the domains can be doped with any number of materials, such as antioxidants, ions, ionomers, contrast agents, particles, metals, pigments, dyes, biomolecules, polymers, proteins and/or therapeutic agents.

The first polymer can be additionally crosslinked or copolymerized with the second polymer if, for example, acryloxy, methacryloxy-, acrylamido-, allyl ether, or vinyl functional groups are incorporated into one end or both ends of the polyurethane prepolymer and then cured by UV or temperature in the presence of an initiator. For instance, a polyurethane dimethacrylate or polyurethane bisacrylamide can be used in the first network by curing in the presence of a solvent (such as dimethylacetamide) and then evaporating the solvent. The addition of chemical crosslinks (rather than just physical crosslinks) to the IPN adds a level of mechanical stability against creep or fatigue caused by continuous, dynamic loading.

In addition, a multi-arm (multifunctional) polyol or isocyanate can be used to create crosslinks in the polyurethane. In this case, a fully interpenetrating polymer network is created (rather than a semi-interpenetrating polymer network). The result is a composite material with the high strength and toughness of polyurethane and the lubricious surface and biphasic bulk behavior of the poly(acrylic acid). Alternatively, other crosslinking methods can be used, including but not limited to gamma or electron-beam irradiation. These features are especially important for bearing applications such as artificial joint surfaces, or as more biocompatible, thrombo-resistant, long-term implants in other areas of the body such as the vascular system or the skin. Being swollen with water also allows imbibement with solutes such as therapeutic agents or drugs for localized delivery to target areas of the body.

In another embodiment of the present invention, the first polymer can be linked to the second polymer. For example, polyurethane can be linked through a vinyl-end group. Depending on the reactivity ratio between the end group and the monomer being polymerized, different chain configurations can be yielded. For instance, if the reactivity of the monomer with itself is much greater than the end group with the monomer, then the second polymer will be almost completely formed before the addition of the first polymer to the chain. On the other hand, if the reactivity of the monomer and the end group are similar, then a random grafting-type copolymerization will occur. The monomers and end groups can be chosen based on their reactivity ratios by using a table of relative reactivity ratios published in, for example, The Polymer Handbook. The result of these will be a hybrid copolymer/interpenetrating polymer network.

Any number or combinations of ethylenically unsaturated monomers or macromonomers (i.e., with reactive double bonds/vinyl groups) can be used alone or in combination with various solvents and selectively introduced into one or more of the phases of the polymer as long as at least 2% of such monomers is ionizable, i.e., contains carboxylic acid and/or sulfonic acid functional groups. Other monomers include but are not limited to dimethylacrylamide, acrylamide, NIPAAm, methyl acrylate, methyl methacrylate, hydroxyethyl acrylate/methacrylate, and any vinyl-based monomer containing sulfonic acid groups (e.g. acrylamido methyl propane sulfonic acid, vinyl sulfonic acid, 3-sulfopropyl acrylate (or methacrylate), 2-methyl-2-propene-1-sulfonic acid sodium salt 98%, or any monomers in which sulfonic acid is conjugated (allyl ethers, acrylate/methacrylates, vinyl groups, or acrylamides). The monomer can also include any monomers containing carboxylic acid groups conjugated to allyl ethers, acrylate/methacrylates, vinyl groups, or acrylamides. In addition, the monomers can be used in combination, such as both carboxyl acid and sulfonic acid containing monomers, to create a carboxylate/sulfonate copolymer. The pendant functional groups on polymers resulting from these monomers and monomer combinations can be subject to subsequent chemical reactions to yield other functionalities to the final polymer.

In one embodiment, a preformed, thermoplastic polymer may be immersed in acrylic acid (or in a solution of acrylic acid (1%-100%) or other vinyl monomer solution) along with about 0.1% v/v crosslinker (e.g., triethylene glycol dimethacrylate or N,N methylene bisacrylamide) with respect to the monomer and about 0.1% v/v photoinitiator (e.g. 2-hydroxy-2-methyl propiophenone) with respect to the monomer. The acrylic acid solution can be based on water, salt buffer, or organic solvents such as dimethylacetamide, acetone, ethanol, methanol, isopropyl alcohol, toluene, dichloromethane, propanol, dimethylsulfoxide, dimethyl formamide, or tetrahydrofuran. The polymer may be swollen by the monomer due to salvation of the soft segments in the polymer. The monomer content in the swollen polymer can range from as little as about 1% to up to about 90%.

The monomer-swollen polymer may then be removed, placed in a mold made of glass, quartz, or a transparent polymer, then exposed to UV light (or elevated temperature) to initiate polymerization and crosslinking of the monomers. Alternatively, instead of using a mold, the monomer-swollen polymer can be polymerized while fully or partially exposed to air or an inert atmosphere (e.g., nitrogen or argon), or alternatively in the presence of another liquid such as an oil (e.g., paraffin, mineral, or silicone oil). For medical applications, it is possible that polymerization step can be performed in vivo without a mold.

Depending on the initiator used, exposure to UV light, IR, or visible light, a chemical, electrical charge, or elevated temperature leads to polymerization and crosslinking of the ionizable monomers within the hydrophobic polymer. As an example, acidic monomers (e.g. acrylic acid) are polymerized to form an ionic polymer within a preformed thermoplastic, hydrophobic matrix, forming an interpenetrating polymer network ("IPN"). Solvents can be extracted out by heat and convection or by solvent extraction. Solvent extraction involves the use of a different solvent (such as water) to extract the solvent from polymer, while heat or convection relies upon evaporation of the solvent. Depending on the pKa of the ionic polymer (e.g., pKa of PAA=4.7), an acidic pH would leave the ionic polymer more protonated while a more basic pH would leave it more ionized.

Swelling of the IPN in aqueous solution such as phosphate buffered saline (or other buffered salt solution) at neutral pH will lead to ionization of the poly(acrylic acid) and further swelling with water and salts. The resulting swollen IPN will have a lubricious surface conferred by the hydrophilic, charged poly(acrylic acid) and high toughness and mechanical strength conferred by the thermoplastic. In the case of a polyurethane-based IPN, the IPN will have a structure in which crystalline hard segments in the polyurethane act as physical crosslinks in the first network, while chemical crosslinks will be present in the second network.

The materials can also be crosslinked after synthesis using gamma radiation or electron beam radiation. In one example, polyurethane/polyacrylic acid can be synthesized and then crosslinked by gamma irradiation, for instance with doses of, for example, 5, 10, 15, 20, or 25 kGy. In this case, the polymerization of polyacrylic acid would be done in the absence of a crosslinker, and after formation of the polymer blend (physical IPN), the material would be exposed to gamma radiation. This would have the dual purpose of sterilizing and crosslinking the polyurethane. It is known in the art that crosslinking of poly(acrylic acid) hydrogels using gamma irradiation shows a dose-dependence to the crosslinking of the polymer. This process can also be applied to other combinations of first and second network polymers, e.g., polyurethane and polymethyl methacrylate, ABS and polyacrylic acid, etc.

In addition to the starting thermoset and thermoplastic hydrophobic polymers identified above, modifications to and derivatives of such polymers may be used, such as sulfonated polyurethanes. In the case of the polyurethanes, the polyurethane polymer can be a commercially available material, a modification of a commercially available material, or be a new material. Any number of chemistries and stoichiometries can be used to create the polyurethane polymer. For the hard segment, isocyanates used are 1,5 naphthalene diisocyanate (NDI), isophorone isocyanate (IPDI), 3,3-bitoluene diisocyanate (TODI), methylene bis (p-cyclohexyl isocyanate) ($H_{12}$MDI), cyclohexyl diisocyanate (CHDI), 2,6 toluene diisocyanate or 2,4 toluene diisocyanate (TDI), hexamethyl diisocyanate, or methylene bis (p-phenyl isocyanate). For the soft segment, chemicals used include, for example polyethylene oxide (PEO), polypropylene oxide (PPO), poly(tetramethylene oxide) (PTMO), hydroxy terminated butadiene, hydroxybutyl terminated polydimethylsiloxane (PDMS), polyethylene adipate, polycaprolactone, polytetramethylene adipate, hydroxyl terminate polyisobutylene, polyhexamethylene carbonate glycol, poly (1,6 hexyl 1,2-ethyl carbonate, and hydrogenated polybutadiene. Any number of telechelic polymers can be used in the soft segment, if end-groups that are reactive with isocyanates are used. For instance, hydroxyl- or amine-terminated poly(vinyl pyrrolidone), dimethylacrylamide, carboxylate or sulfonated polymers, telechelic hydrocarbon chains (with hydroxyl and/or amine end groups), dimethylolpropionic acid (DMPA), or these in combination with each other or with other soft segments mentioned above (e.g., PDMS) can be used. Ionic soft segments (or chain extenders) such as dihydroxyethyl propionic acid (DMPA) (or its derivatives) can be used to make a water-dispersible polyurethane, so long as the ionic chain extender does not comprise more than 2% of the material.

Chain extenders include, for example, 1,4 butanediol, ethylene diamine, 4,4'methylene bis (2-chloroaniline) (MOCA), ethylene glycol, and hexane diol. Any other compatible chain extenders can be used alone or in combination. Crosslinking chain extenders can be used containing isocyanate-reactive endgroups (e.g. hydroxyl or amine) and a vinyl-based functional group (e.g. vinyl, methacrylate, acrylate, allyl ether, or acrylamide) may be used in place of some or all of the chain extender. Examples include 1,4 dihydroxybutene and glycerol methacrylate. Alternatively, crosslinking can be achieved through the use of a polyol such as glycerol which contains greater than two hydroxyl groups for reaction with isocyanates.

In some embodiments, at least 2% of the hydrophilic monomers in the second network is ionizable and anionic (capable of being negatively charged). In one such embodiment, poly(acrylic acid) (PAA) hydrogel is used as the second polymer network, formed from an aqueous solution of acrylic acid monomers. Other ionizable monomers include ones that contain negatively charged carboxylic acid or sulfonic acid groups, such as methacrylic acid, 2-acrylamido-2-methylpropanesulfonic acid, sulfopropyl methacrylate (or acrylate), vinyl sulfonic acid, or vinyl-conjugated versions of hyaluronic acid, heparin sulfate, and chondroitin sulfate, as well as derivatives, or combinations thereof. The second network monomer may also be positively charged or cationic. These other monomers can also be in a range of 1%-99% in either water or organic solvent, or be pure (100%). One embodiment of the monomer used to form the second network can be described by the following characteristics: (1) it is capable of swelling the polyurethane, (2) capable of polymerizing, and (3) is ionizable.

Other embodiments use a co-monomer in addition to the ionic polymer that may be non-ionic, such as acrylamide, methacrylamide, N-hydroxyethyl acrylamide, N-isopropylacrylamide, methylmethacrylate, N-vinyl pyrrolidone, 2-hydroxyethyl methacrylate, 2-hydroxyethyl acrylate or derivatives thereof. These can be copolymerized with less hydrophilic species such as methylmethacrylate or other more hydrophobic monomers or macromonomers. These can also be polymerized alone or copolymerized with the aforementioned hydrophilic and/or ionizable monomers.

Crosslinked linear polymer chains (i.e., macromolecules) based on these monomers may also be used in the second network, as well as biomacromolecules (linear or crosslinked) such as proteins and polypeptides (e.g., collagen, hyaluronic acid, or chitosan). The choice of the second material will depend on the target application, for instance in orthopaedic applications, hyaluronic acid may be useful because it is a major component of joint cartilage. In addition, biological molecules may carry certain benefits such as intrinsic biocompatibility or therapeutic (e.g., wound healing and/or antimicrobial) properties that make them useful as material components.

Any type of compatible cross-linkers may be used to crosslink the second network in the presence of any of the aforementioned first networks such as, for example, ethylene glycol dimethacrylate, ethylene glycol diacrylate, diethylene glycol dimethacrylate (or diacrylate), triethylene glycol dimethacrylate or diacrylate), tetraethylene glycol dimethacrylate (or diacrylate), polyethylene glycol dimethacrylate, or polyethylene glycol diacrylate, methylene bisacrylamide, N,N'-(1,2-dihydroxyethylene) bisacrylamide, derivatives, or combinations thereof. Any number of photoinitiators can also be used depending on their solubility with the precursor solutions/materials. These include, but are not limited to, 2-hydroxy-2-methyl-propiophenone and 2-hydroxy-1-[4-(2-hydroxyethoxy) phenyl]-2-methyl-1-propanone. In addition, other initiators such as benzoyl peroxide, 2-oxoglutaric acid, azobisisobutyronitrile, or potassium persulfate (or sodium persulfate) can be used. For instance, benzoyl peroxide is useful for temperature-initiated polymerizations, while azobisisobutyronitrile and sodium persulfate are useful as radical initiators.

In another embodiment, a solvent can be used as a "trojan horse" to deliver monomers that otherwise would not mix (or solubilize with) the polymer to one (or more) phases of the polymer. The solvent must be carefully chosen based on the specific qualities and phases of the polymer and monomers. For instance, acetic acid is capable of swelling but does not dissolve many polyurethanes. Therefore, acetic acid can be used to carry other monomers such an acrylamide solution, that otherwise would not enter polyurethane, into the bulk of the polyurethane. This allows the acrylamide to be selectively polymerized inside one phase of the polyurethane. The acetic acid can then be washed out leaving behind a polyurethane with one or more new properties. Other solvents that can be used include, but are not limited to, dichloromethane, methanol, propanol, butanol, (or any alkyl alcohol), acetone, dimethylacetamide, dimethylformamide, dimethylsulfoxide, tetrahydrofuran, diethylether, or combinations of these. Taking into account the solubilities in the phases of the polymer, solvents with varying degrees of swelling of one can be chosen. Solubilities of the solvents and components of the material to be swollen can be obtained from polymer textbooks such as The Polymer Handbook or can be measured experimentally.

The present invention can be used to form a bulk-interpenetrated coating on a polymeric material. This coating is inextricably entangled with the underlying polymer matrix, and is in contrast to conventional surface coatings in which a material is grafted or tethered to a surface. In one example of a bulk-interpenetrated coating, a thermoplastic polymer is coated on one or more sides or is immersed in an ionizable monomer such as acrylic acid in the presence of a photoinitiator and a crosslinking agent. The thermoplastic is then placed in a mold and then exposed to an initiator (e.g., UV light or heat) for a predetermined period of time. The mold can be fully or partially transparent and/or masked to facilitate regionally specific curing of the monomer. The modified material is then immersed in buffered saline solution to neutralize the ionic polymer and render the surface lubricious and hydrophilic. The modified plastic can then be further remolded by application of heat, solvent, and/or pressure and then shaped to the desired dimensions. The modified plastic can then be bonded to various surfaces such as metal, glass, plastic, or other materials by applying heat or solvent (such as acetone) to the unmodified plastic surface and bringing the surface in contact with the surface of interest.

Among the applications of the invention are the creation of hydrophilic, lubricious sidings or coatings to reduce drag and/or biofilm formation and/or barnacle formation in marine vessels, diving or swimming suits, other water crafts or water-borne objects, or pipes. In addition, the invention can be used as a method for making bearings and moving parts for applications such as engines, pistons, or other machines or machine parts. The invention can also be used in artificial joints systems or long-term implants in other areas of the body, such stents and catheters for the vascular or urinary system or implants, patches, or dressings for the skin.

Figure 2:
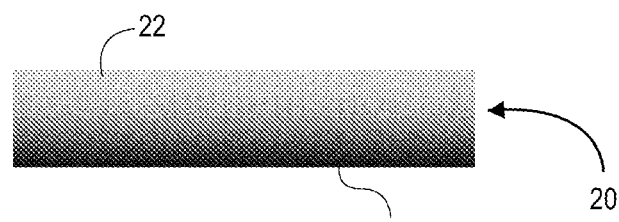
FIG. 2 illustrates a composition gradient formed in an article along a thickness direction
Figure 3:
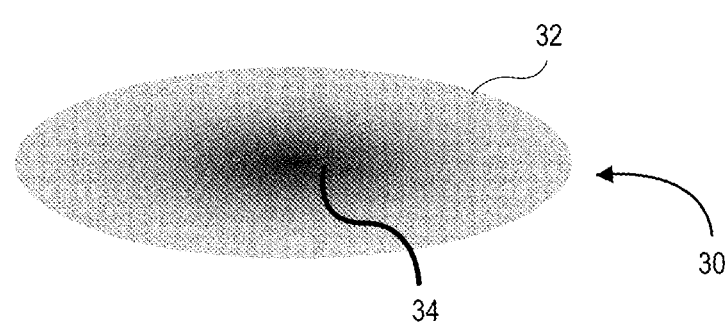
FIG. 3 illustrates a composition gradient formed in an article along a radial direction.

FIGS. 2 and 3 illustrate how the invention can be used to create a composition gradient within a starting homopolymer. In FIG. 2, a gradient is formed in material 20 along a thickness direction, with the IPN formed on one side 22 and extending in a diminishing concentration to another side 24, e.g., substantially only homopolymer. In FIG. 3, the IPN concentration gradient is radial within material 30, with the outer surface 32 being the highest concentration of IPN and the center or core 34 having the lowest concentration of IPN. A reverse gradient can also be made in the case of a cylinder or a sphere, with the IPN disposed in the core of the shape and the hydrophobic polymer being disposed in the outer aspect of the shape. This is useful in creating a conductive semi-IPN wire that is encapsulated within an insulating hydrophobic material via a gradient composition.

Figure 4A:
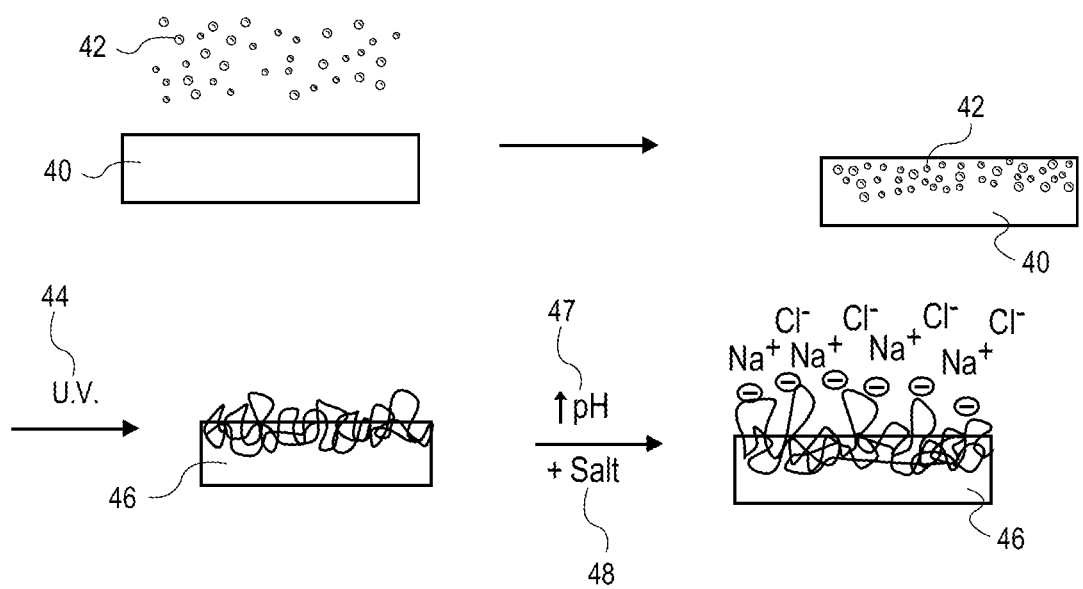
FIG. 4A illustrates a method of fabricating a thermoplastic gradient IPN according to the present invention.

FIG. 4A illustrates a method of fabricating a thermoplastic gradient IPN according to the present invention. One side of the thermoplastic material 40 is imbibed with a monomer solution 42 along with a photoinitiator (not shown) and a crosslinker (not shown), and then the monomer is polymerized and crosslinked (e.g., with UV light 44) within the thermoplastic to form a gradient IPN 46. Increasing the pH to neutral 47 and introducing salt 48 into the surrounding fluid leads to ionization of the 2nd polymer network. Alternatively, non-ionic monomers can be used as the basis in a part (to form a copolymer). The non-ionic polymer would not be ionized by the buffer solution, but would still create a hydrophilic surface. Either type of monomer system can be used in conjunction with either water or an organic solvent.

In one embodiment, a TP/PAA IPN can be created in a gradient if polyurethane ("PU") is swollen in AA on one side only or if the swelling time is limited such that diffusion of the monomers through the bulk of the TP is not complete. This is especially useful in the creation of osteochondral grafts for orthopaedic joint replacement materials. For instance, in the case of a cartilage replacement material, one side of the material is made lubricious and water swollen, while the other remains a solid (pure thermoplastic). In between is a transition between a TP/PAA IPN and TP, with decreasing PAA content from one surface to the other. Alternatively, bulk materials with a TP/PAA IPN outer aspect and PU-only "core" can be made if the diffusion of AA into the TP is precisely controlled by timing the infiltration of the monomers into the bulk. The differential swelling that results from this configuration can lead to remaining stresses (compressive on the swollen side, tensile on the non-swollen side) that can help enhance the mechanical and fatigue behavior of the material. In the case of a material with a thickness gradient, the base of thermoplastic-only material can be used for anchoring, adhering, or suturing the device to the anatomical region or interest. This base can be confined to a small area or be large (e.g., a skirt) and can extend outward as a single component or multiple components (e.g., straps). The internal stresses built up within the thermoplastic during processing or after swelling can be reduced by temperature-induced annealing. For instance, temperatures of 60-120 degrees Celsius can be used for various times (30 minutes to many hours) to anneal the polymer, and the heat can be applied in an oven, by a hot surface, by radiation, or by a heat gun. The thermoplastic can later be crosslinked using, for example, gamma or electron beam radiation.

FIG. 4B illustrates how the properties of gradient IPN's can vary to produce the desired composition. FIG. 4C illustrates how the concentration gradient of the hydrophobic polymer and the ionic polymer can vary across the thickness (between the two surfaces) of a gradient IPN. The composition gradient yields a property gradient in which the IPN is hydrated and more compliant on one side, and less hydrated (or not hydrated) and stiff on the other.

Figure 5:
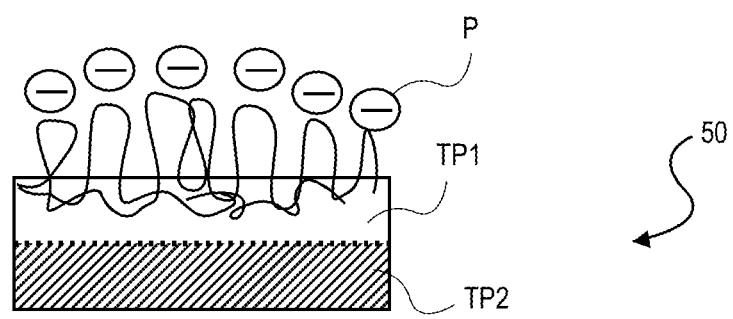
FIG. 5 illustrates a laminate structure or an IPN or semi-IPN.

Articles made from the IPN's and semi-IPN's of this invention may also be formed in a laminate structure, as illustrated in FIG. 5. In one example, the IPN structure 50 is comprised of a hydrophilic polymer (P) such as poly(acrylic acid) that is interpenetrating a first thermoplastic (TP1) such as polyether urethane, which is formed on top of a second thermoplastic (TP2) such as polycarbonate urethane. Both TP1 and TP2 can be themselves comprised of multiple layers of various hardnesses and properties. In addition, many more than two thermoplastic layers can be used, and one or more of the thermoplastics can be crosslinked. Finally, non-thermoplastic elements can be incorporated into this construct.

Articles formed from the gradient or homogeneous IPN's and semi-IPN's of this invention may be shaped as desired. FIG. 6 illustrates shaping of a gradient IPN article. This process may also be used to shape a homogeneous IPN or semi-IPN.

As shown in FIG. 6, heat 61 can be used to re-anneal the physical crosslinks in the polymer (e.g., the hard segments in the polyurethane) in the thermoplastic side 50 of the gradient IPN to lead to different desired curvatures after bending (e.g., over a mold or template) and cooling. FIG. 6 illustrates both convex 62 and concave 64 curvatures on the thermoplastic side of the gradient IPN. Other shapes may be formed, of course, as desired. The use of thermoplastic facilitates molding of a device to a desired shape by, for example, injection molding, reactive injection molding, compression molding, or alternatively, dip-casting. The molded device can then be subjected to subsequent network infiltration and polymerization steps to yield the new IPN material.

Shaping of IPN and semi-IPN articles according to this invention may be formed in situ, such as within a human body. For example, FIGS. 7A-B illustrate heating 71 of a thermoplastic gradient IPN 70 to enable it to wrap around the curvature of a femoral head 72. FIGS. 7C-D illustrate the application of heat 74 to a thermoplastic gradient IPN 73 to enable it to adapt to the curvature of a hip socket 75.

Shaped or unshaped IPN and semi-IPN articles made according to this invention may be attached to other surfaces. FIG. 8A-D shows how a bonding agent 81 such as a solvent, cement, or glue can be used to attach the thermoplastic gradient IPN article 80 to a surface 82 at a bonded interface 83. Addition of the solvent, for example, causes the material to dissolve locally, and after contact with a surface and drying of the solvent, the thermoplastic adheres to the surface. This method can be used to create "paneling" of the present invention of various objects, including but not limited to marine vessel hull surfaces. A "coating" can be applied by vacuum forming the material over the contours of the vessel or a part of the vessel. A similar approach can be used to attach a gradient IPN to bone surfaces in joints.

The composition of this invention, formed, e.g., by the method of this invention, may be used in a variety of settings. One particular use is as artificial cartilage in an osteochondral graft. The present invention provides a bone-sparing arthroplasty device based on an interpenetrating polymer network that mimics the molecular structure, and in turn, the elastic modulus, fracture strength, and lubricious surface of natural cartilage. Emulating at least some of these structural and functional aspects of natural cartilage, the semi-IPNs and IPNs of the present invention form the basis of a novel, bone-sparing, "biomimetic resurfacing" arthroplasty procedure. Designed to replace only cartilage, such a device is fabricated as a set of flexible, implantable devices featuring lubricious articular surfaces and osteointegrable bone-interfaces.

In principle, the device can be made for any joint surface in the body. For example, a device to cover the tibial plateau will require an analogous bone-preparation and polymer-sizing process. For a device to cover the femoral head in the hip joint, a cap shaped device fits snugly over the contours of the femoral head. For a device to line the acetabulum, a hemispherical cup-shaped device stretches over the lip and can be snapped into place in the socket to provide a mating surface with the femoral head. In this way, both sides of a patient's hip joint can be repaired, creating a cap-on-cap articulation. However, if only one of the surfaces is damaged, then only one side may be capped, creating a cap-on-cartilage articulation. In addition, the materials of the present invention can be used to cap or line the articulating surfaces of another joint replacement or resurfacing device (typically comprised of metal) to serve as an alternative bearing surface.

To create a cap-shaped device using the present invention for the shoulder joint (also a ball-and-socket joint), a process similar to that of the hip joint is used. For instance, a shallow cup can be created to line the inner aspect of the glenoid. Furthermore, devices for other joints in the hand, fingers, elbow, ankles, feet, and intervertebral facets can also be created using this "capping" concept. In one embodiment in the distal femur, the distal femur device volume follows the contours of the bone while sparing the anterior and posterior cruciate ligaments.

In one embodiment of prosthetic cartilage formed according to this invention, a polyether urethane device pre-formed with shore hardness of 75 D is injection molded. This device is then solution casted in a Vitamin E-containing solution containing polyether urethane formulated to a dry shore hardness of 55 D (e.g., 25% Elasthane™ 55 D in dimethylacetamide). The casted layer may then be dried in a convection oven to remove the solvent. The device may then be immersed in a solution of acrylic acid, photoinitiator, and crosslinker for 24 hours, and then placed over a glass mold and exposed to UV light. The resulting device may then be soaked and washed in phosphate buffered saline. This process is used to create either convex or concave devices for arthroplasty applications. The injection-molded preform has on one of its sides a plurality of spaces (pores or features) that make capable of being anchored to bone with traditional orthopaedic bone cement.

In another embodiment of the device, a polycarbonate urethane pre-formed with surface features on one side is fabricated, followed by dip-casting of one of its sides in a solution of polyether urethane and then subjected to a process similar to the one above. In still another embodiment, a polyether urethane pre-form of shore hardness 55 D (e.g., Elasthane™ 55 D) is injection molded, followed by immersion in a monomer solution as above. After curing of the second polymer network, the device is dip-casted on one side with polycarbonate urethane of shore hardness 75 D. In any of these embodiments, additional surface features can be added to the bone interface side of the device through a number of means, including but not limited to machining (lathe and end-mill), solution casting, solvent-welding, ultrasonic welding, or heat-welding.

Porous polycarbonate urethane IPN and semi-IPN structures may be made according to this invention. Particles (size range: 250-1500 μm) of polycarbonate urethane, including but not limited to Bionate® 55 D, Bionate® 65 D, and Bionate® 75 D, may be sintered in a mold using heat (220-250° C.), pressure (0.001-100 MPa), and/or solvent for 10-30 min. The structures will have a final pore size of 50-2000 μm, porosity of 15-70%, and a compressive strength exceeding 10 MPa. The final structures will have porosity to promote tissue ingrowth/integration for medical and veterinary applications. This construct can be used alone or with an overlying bearing surface made from any of the lubricious polymers described in this invention. This material could be used as a cartilage replacement plug in joints of the body where cartilage has been damaged, as described below.

The composition of this invention, made, e.g., according to the method of this invention, may be used as a fully or partially synthetic osteochondral graft. The osteochondral graft consists of a lubricious, cartilage-like synthetic bearing layer that may be anchored to porous bone or a synthetic, porous bone-like structure. The bearing layer has two regions: a lubricious surface layer and a stiff, bone anchoring layer. In one embodiment, the top, lubricious region of the bearing layer consists of an interpenetrating polymer network that is composed of two polymers. The first polymer may be a hydrophobic thermoplastic with high mechanical strength, including but not limited to polyether urethane, polycarbonate urethane, silicone polyether urethane, and silicone polycarbonate urethanes, or these materials with incorporated urea linkages, or these materials with incorporated urea linkages (e.g. polyurethane urea). The second polymer may be a hydrophilic polymer derived from ionizable, vinyl monomers, including but not limited to acrylic acid and/or sulfopropyl methacrylate. The bottom region of the bearing layer (bone anchoring layer) may be a stiff, non-resorbable thermoplastic that can be caused to flow with ultrasonic welding vibration, ultrasonic energy, laser energy, heat, RF energy and electrical energy. The bone anchoring layer is used to anchor the bearing layer to bone or a bone-like porous structure. If porous bone is used, it can be cancellous bone from a human or animal. If a synthetic bone-like material is used, it can consist of porous calcium-phosphate (and/or other materials, including but not limited to porous carbonated apatite, beta-tricalcium phosphate, or hydroxyapatite), or a porous resorbable or non-resorbable thermoplastic as described above, including but not limited to polycarbonate urethane, polyether urethane, PLA, PLLA, PLAGA, and/or PEEK. The bearing layer is anchored to the porous bone or bone-like structure via application of pressure combined with energy that cause the bone anchoring material to melt and flow into the pores or spaces of the bone or bone-like structure, after which the energy source is removed and the material resolidifies. The energy source can include but is not limited to vibration, ultrasonic energy, laser energy, heat, RF energy, and electrical energy.

The following figures illustrate various embodiments of the present invention as a device to partially or completely resurface damaged joints in the body of mammals (animals or human). These devices can be fixated to bone through any number of means, such as a press-fit, screws (metal or plastic, either resorbable or nonresorbable), sutures (resorbable or nonresorbable), glue, adhesives, light-curable adhesives (e.g. polyurethane or resin-based), or cement (such as polymethylmethacrylate or calcium phosphate, or dental cements).

Figure 9A:
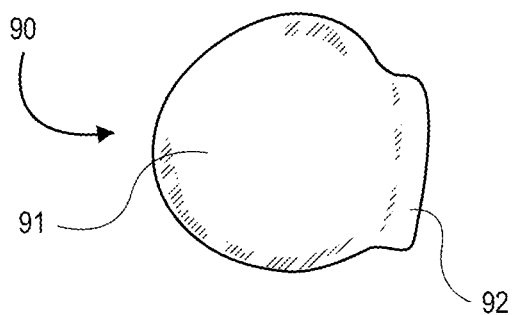
FIGS. 9A-D illustrate how an osteochondral graft implant formed from an IPN or semi-IPN of this invention can be used to replace or augment cartilage within a joint.
Figure 9B:
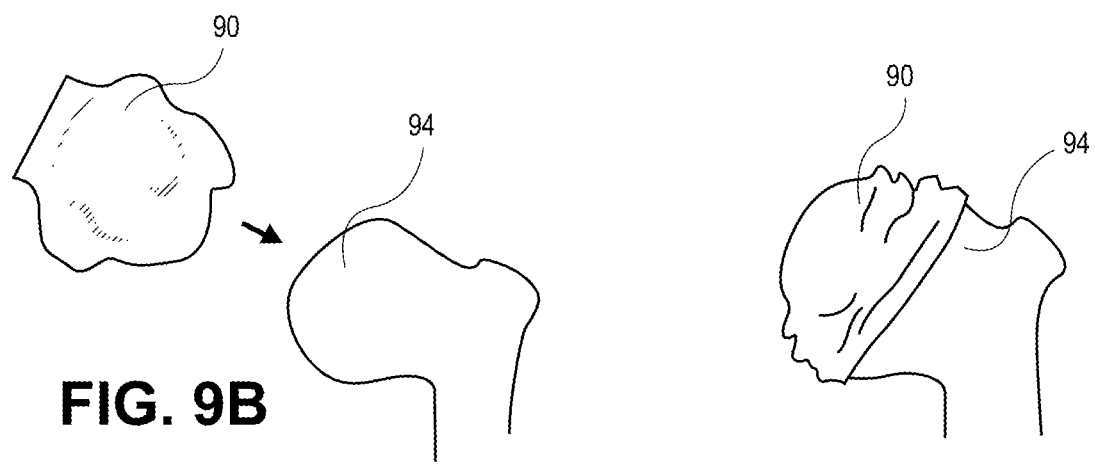
Figure 9C:
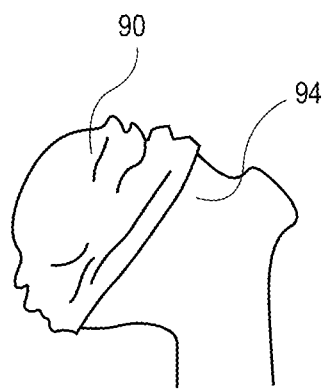
Figure 9D:
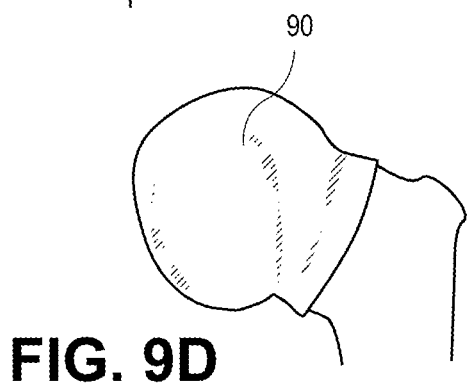

FIGS. 9A-D illustrate how an osteochondral graft implant formed from an IPN or semi-IPN of this invention can be used to replace or augment cartilage within a joint, such as a hip or shoulder joint. As shown in FIG. 9A, the prosthetic cartilage 90 is formed as a sock having a cap portion 91 and an optional collar 92. The prosthesis 90 may be inverted, as shown in FIG. 9B, and slipped over the head 94 of the humerus or femur. In an alternative embodiment shown in FIGS. 10A-B, the prosthesis 90 may include an opening 95 to accommodate a ligament 96 or other anatomical structure.

Implants and other articles may be made in a variety of complex shapes according to the invention. FIGS. 11A-E show osteochondral grafts formed from an IPN or semi-IPN of this invention that may be used singly or in any combination needed to replace or augment cartilage within a knee joint. FIG. 11A shows an osteochondral graft 110 adapted to engage the femoral condyles (or alternatively, just one condyle). FIG. 11B shows osteochondral grafts 111 and 112 adapted to engage one or both sides of the tibial plateau 113. FIG. 11C shows an osteochondral graft 118 adapted to engage the patella 114 and to articulate with an osteochondral graft 119 adapted to engage the patellofemoral groove 115. FIG. 11D show osteochondral grafts 116 and 117 adapted to engage the lateral and medial menisci. FIG. 11E shows how some of these prostheses may be assembled in place within the knee joint.

Osteochondral grafts may also be used in other joints, such as in the finger, hand, ankle, elbow, feet or vertebra. For example, FIGS. 12A-B show osteochondral grafts 121 and 122 formed from the IPN's or semi-IPN's of this invention and shaped for use in a finger joint. FIGS. 13A-B show a labrum prosthesis 131 formed from an IPN or semi-IPN of this invention for use in replacing or resurfacing the labrum of the shoulder or hip. FIG. 14 shows the use of an IPN or semi-IPN of this invention as a bursa osteochondral graft 141, labrum osteochondral graft 142, glenoid osteochondral graft 143 and humeral head osteochondral graft 144. FIG. 15 shows the use of an IPN or semi-IPN of this invention as prostheses 151 and 152 for resurfacing intervertebral facets.

The IPN's and semi-IPN's compositions of this invention may be formed as prosthetic cartilage plugs for partial resurfacing of joint surfaces. FIG. 16A shows a prosthetic cartilage plug 160 formed from a gradient IPN composition of this invention. Plug 160 has a stem portion 161 formed on a thermoplastic side of the article and adapted to be inserted into a hole or opening in a bone. The head 162 of the plug is formed to be a lubricious IPN or semi-IPN, as described above. FIG. 16B shows a variation in which porous surfaces are formed on the underside 163 of head 162 and on the base 164 of stem 161. In the embodiment of FIGS. 16C-D, the porous surface is formed only in the center portion 165 of base 164. In all embodiments, stem 161 may be press fit into a hole or opening in the bone, leaving the lubricious IPN surface to be exposed to act as prosthetic cartilage.

FIG. 17 shows an embodiment of a prosthetic cartilage plug 170 in which the stem 171 is provided with helical ridges 173 to form a screw for fixation of the plug to bone. The top surface of the head 172 is a lubricious IPN or semi-IPN, as above.

FIG. 18 shows an embodiment of a prosthetic cartilage plug 180 having three stems 181 for press fit insertion into holes in the bone for fixation. The top surface of plug head 182 is a lubricious IPN or semi-IPN, as above.

FIG. 19 shows an embodiment of a prosthetic cartilage plug 190 in which the exposed head portion 192 is substantially the same diameter as the stem 191. Stem 191 may be press fit into a hole in the bone for fixation. The top surface of plug head 192 is a lubricious IPN or semi-IPN, as above.

FIG. 20 shows an embodiment of a prosthetic cartilage plug 200 in which the exposed head portion 202 is narrower than stem 201, and stem 201 widens toward base 203. Stem 201 may be press fit into a hole in the bone for fixation. The top surface of plug head 202 is a lubricious IPN or semi-IPN, as above.

FIG. 21 shows an embodiment of a prosthetic cartilage plug 210 in which the stem 211 has circumferential ridges to aid fixation. Stem 211 may be press fit into a hole in the bone for fixation. The top surface of plug head 212 is a lubricious IPN or semi-IPN, as above.

FIG. 22 shows an embodiment similar to that of FIG. 19 that adds a rough porous surface to stem 221. The top surface of plug head 222 is a lubricious IPN or semi-IPN, as above.

Figure 23:
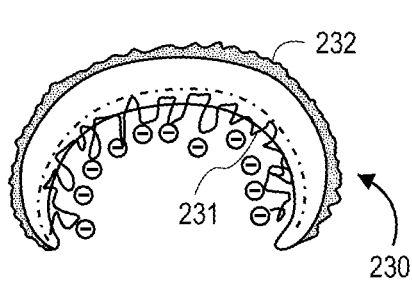
FIG. 23 shows an embodiment of an osteochondral graft formed to physically grip the bone without additional fixation, such as screws or stems.

FIG. 23 shows an embodiment of an osteochondral graft 230 formed to physically grip the bone without additional fixation, such as screws or stems. In this embodiment, the lubricious IPN or semi-IPN portion of the prosthesis is on a concave surface 231 of the device. The opposite convex surface 232 of the device is shaped to match the shape of the bone to which prosthesis 230 will be attached. Surface 232 is porous to facilitate bony ingrowth. The porous material in this case can be fabricated from a porogen method as described in the present invention, with the porogen being sodium chloride, tricalcium phosphate, hydroxyapatite, sugar, and derivatives or combinations thereof. Alternatively, the porosity can be derived from sintering polymer beads (e.g. polyether urethane or polycarbonate urethane) together using heat or solvent.

Figure 24:
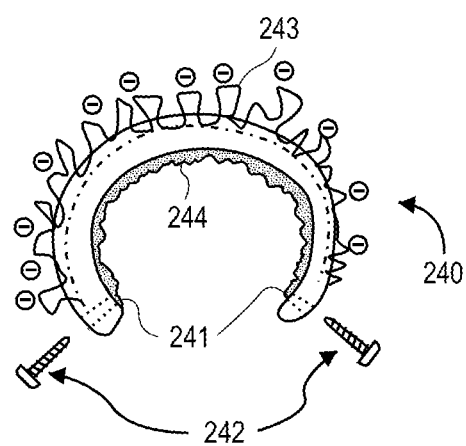
FIG. 24 shows an embodiment of an osteochondral graft having screw holes for screw fixation.

Screw holes may be provided to the osteochondral graft for fixation to the bone. In FIG. 24, prosthesis 240 is provided with two holes 241 for screws 242. The bone-contacting concave side 244 of prosthesis 240 is porous (as above) to promote bony ingrowth and has a shape adapted for physically gripping the bone. The outer convex surface 243 of the prosthesis is a lubricious IPN or semi-IPN, as above.

Figure 25:
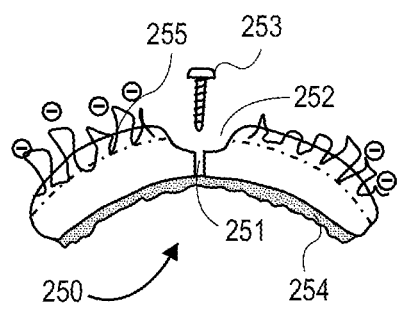
FIG. 25 shows an embodiment of an osteochondral graft having a screw hole and a screw head depression for screw fixation.

In FIG. 25, the osteochondral graft 250 is provided with a screw hole 251 as well as a depression 252 for accommodating the head of a screw 253. The bone-contacting concave side 254 of prosthesis 250 is porous (as above) to promote bony ingrowth and has a shape adapted for physically gripping the bone. The outer convex surface 255 of the prosthesis is a lubricious IPN or semi-IPN, as above.

Figure 26:
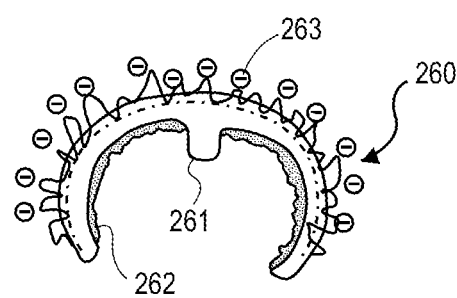
FIG. 26 shows an embodiment of an osteochondral graft having a stem for insertion into a hole in the bone.

FIG. 26 shows an embodiment of an osteochondral graft 260 having a stem 261 for insertion into a hole in the bone. The bone-contacting concave side 262 of prosthesis 260 is porous (as above) to promote bony ingrowth and has a shape adapted for physically gripping the bone. The outer convex surface 263 of the prosthesis is a lubricious IPN or semi-IPN, as above.

Figure 27A:
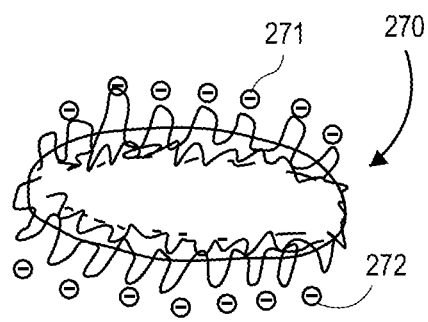
FIGS. 27A-B show embodiments of the composition of this invention used to make two-sided lubricious implants.
Figure 27B:
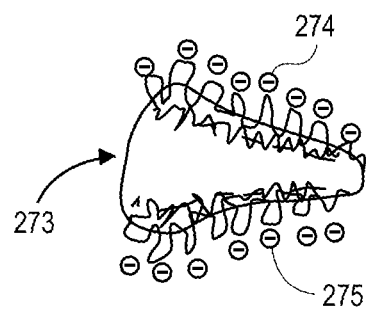

FIGS. 27A-B show embodiments of the composition of this invention used to make two-side lubricious implants. In FIG. 27A, implant 270 is sized and configured to replace an intervertebral disc. Implant 270 has lubricious IPN or semi-IPN surfaces 271 and 272 (formed, e.g., as described above) on its upper and lower sides. FIG. 27B shows a knee spacer 273 having a wedge-shaped cross-section. As with disc prosthesis 270, spacer 273 also has lubricious IPN or semi-IPN surfaces 274 and 275 on its upper and lower sides.

Figure 28:
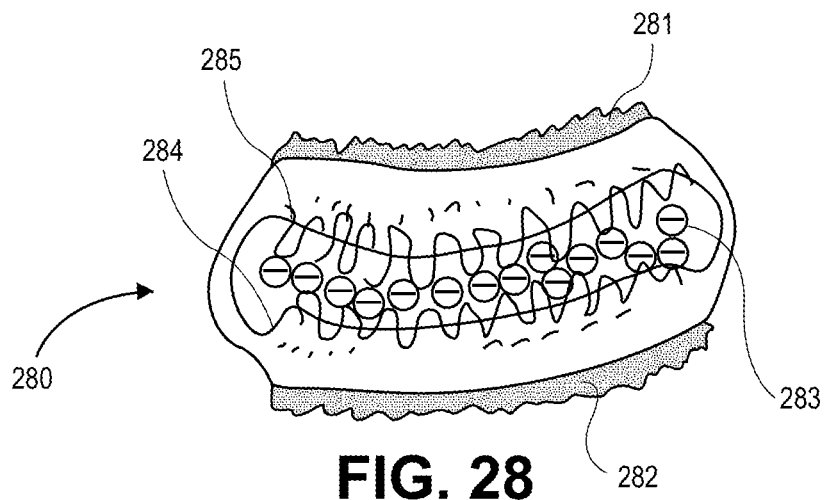
FIGS. 28 and 29 show orthopedic implants that are attached to surfaces of two bones or other anatomic elements that move with respect to each other, such as in a joint.
Figure 29:
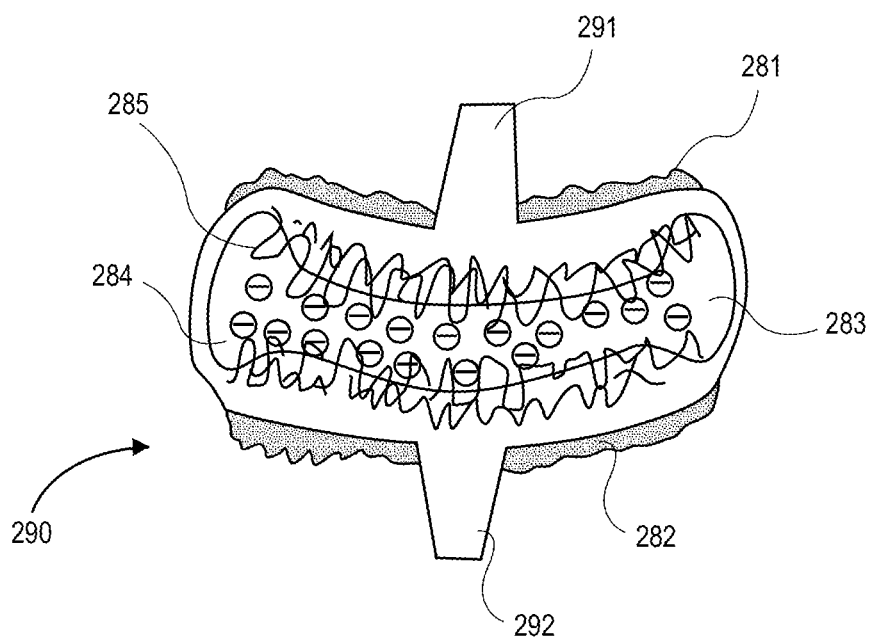

Many of the osteochondral grafts and other implants described above are affixed to a single bone surface. FIGS. 28 and 29 show orthopedic implants that are attached to surfaces of two bones or other anatomic elements that move with respect to each other, such as in a joint. In FIG. 28, implant 280 has upper and lower bone contacting regions 281 and 282 formed to be porous (as described above) to promote bony ingrowth. The interior of implant 280 is a fluid-filled capsule 283. Inwardly facing bearing surfaces 284 and 285 are lubricious IPN or semi-IPN surfaces (as above). Implant 280 can be used, e.g., as an interpositional spacer and as a replacement for the synovial capsule and cartilage of a joint. The implant 290 of FIG. 29 is similar to that of FIG. 28, but adds upper and lower stems 291 and 292 for insertion and fixation in corresponding holes in the bones defining the joint.

Figure 30A:
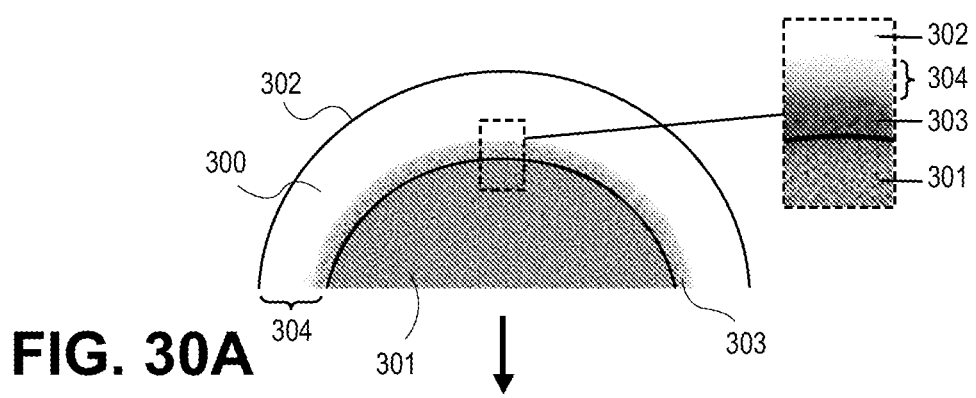
FIGS. 30A-B illustrate the integration of osteochondral grafts and other implants of this invention into bone over time.
Figure 30B:
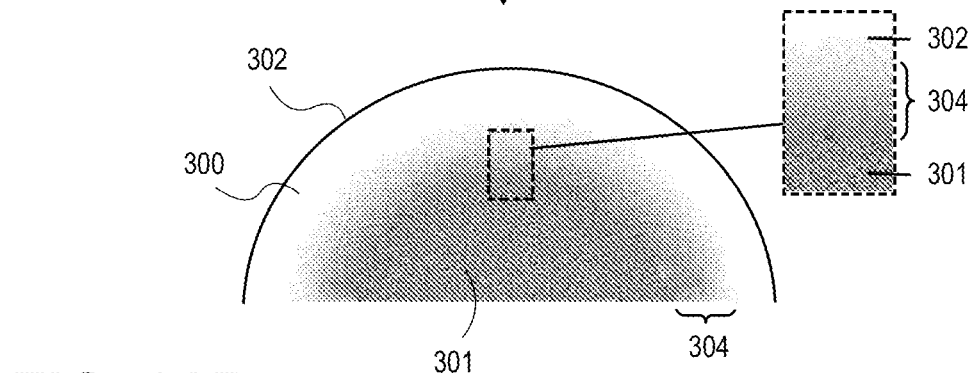

FIGS. 30A-B illustrate the integration of osteochondral grafts and other implants of this invention into bone over time. In FIG. 30A, an osteochondral graft implant 300 formed as described above is placed over bone 301. Implant 300 has a lubricious IPN or semi-IPN surface 302 and a bone interface surface 303 formed from a thermoset or thermoplastic hydrophobic polymer alone, which is optionally porous as described above. Between surface 302 and surface 303 is a gradient or transition zone 304 between the IPN or semi-IPN and the hydrophobic polymer. Over time, bone tissue will grow from bone 301 into and through the bone contacting surface 303, as illustrated in FIG. 30B.

Figure 31A:
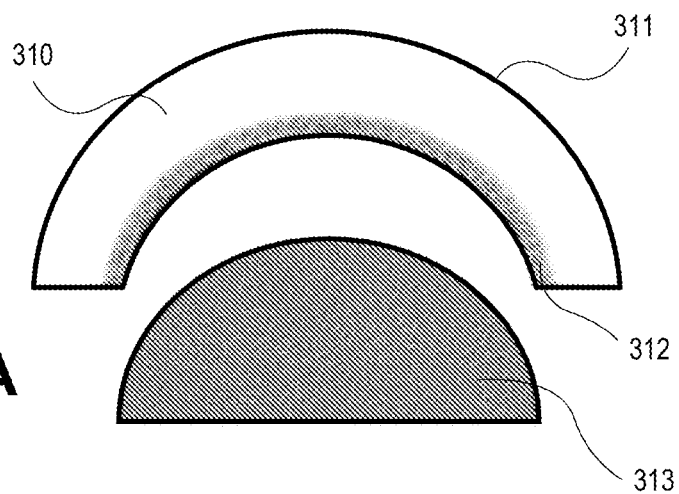
FIGS. 31A-C illustrate three possible configurations of osteochondral implants to repair cartilaginous joint surface according to this invention.
Figure 31B:
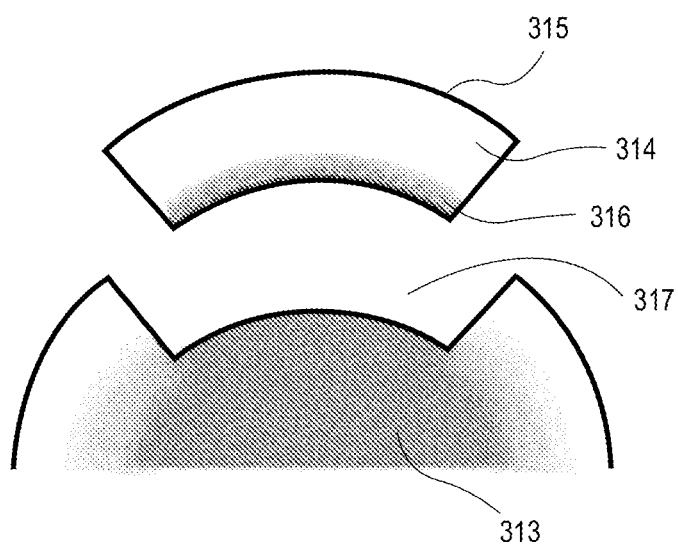
Figure 31C:
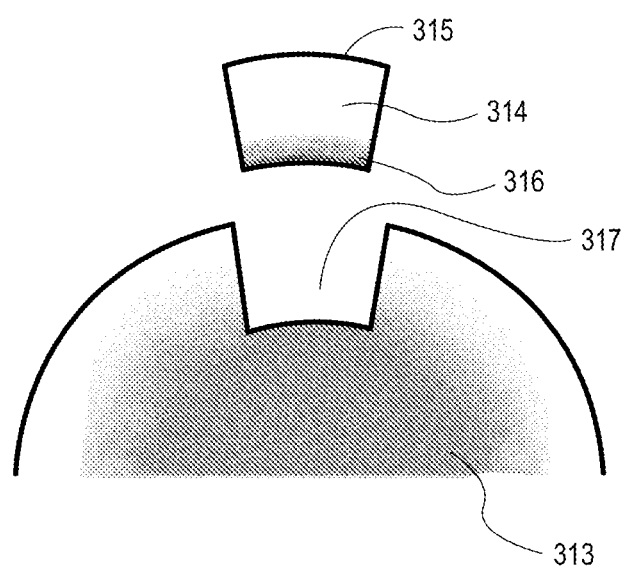

FIGS. 31A-C illustrate three possible configurations of osteochondral implants to repair cartilaginous joint surface according to this invention. In FIG. 31A, implant 310 is formed as a cap having a lubricious IPN or semi-IPN surface 311 transitioning to a bone-contacting surface 312 formed from a thermoset or thermoplastic hydrophobic polymer, as described above. When implanted, implant 310 covers the outer surface of bone 313.

FIGS. 31B and 31C show configurations in which implant 314 is formed as a patch or plug (respectively) having a lubricious IPN or semi-IPN surface 315 transitioning to a bone-contacting surface 316 formed from a thermoset or thermoplastic hydrophobic polymer, as described above. When implanted, implant 314 fits within a prepared opening 317 of bone 313.

The invention has non-medical applications. For example, FIG. 32 shows the use of a lubricious IPN or semi-IPN composition of this invention to resurface the hull of a marine vessel. Panels 320 of a thermoplastic gradient IPN (as described above) have been attached to the surface of hull 322 to reduce drag and biofilm formation. Alternatively, the IPN material can be in some embodiments painted on the hulls as a liquid and allowed to cure or harden. The gradient IPN can be negatively charged on its surface or uncharged and can be made from one or more types of monomer species. Various UV protection and anti-oxidizing agents or other additives can also be incorporated into these materials to improve their performance.

FIG. 33 shows the use of a lubricious thermoplastic or thermoset IPN (as described above) to modify interfacing surfaces of machine parts that move with respect to each other, such as surface 331 of rotating and translating part 330 and surface 333 of stationary part 332. FIG. 34 shows the use of a lubricious thermoplastic or thermoset IPN (as described above) to reduce fluid drag on the inner surface 340 of a pipe 342.

The materials of the present invention have utility in applications requiring electrochemical conductivity. The conductivity of the IPNs and semi-IPNs is based on the flow of ions through the hydrated matrix of the material. Thin films of polyetherurethane were swelled with four different compositions of an acrylic acid and water mixture (15, 30, 50, and 70% acrylic acid in water). Each swelled film was then cured in UV light to form the semi-IPN. The films were then neutralized in PBS. The electrical resistance of the materials was measured using an ohm meter. To measure resistance, the IPN film was lightly patted with a paper towel to remove excess PBS and the ohm meter probes were clipped to the film across a film width of 60-70 mm. The initial and steady-state resistance values were recorded. In addition, the resistances of an unmodified polyetherurethane film and liquid PBS were measured. The resistance of PBS was measured by placing the ohm meter probes directly into a PBS bath at an approximate distance of 60 mm between the probes. Resistance measurements are in the following Table.

TABLE 1

| Material | Lowest resistance reading (k$\Omega$) | Steady-state resistance reading (k$\Omega$) |
|---|---|---|
| PEU alone (0% AA) | out of range (dielectric) | out of range (dielectric) |
| PEU/PAA (15% AA) | 175 | 200 |
| PEU/PAA (30% AA) | 132 | 177 |
| PEU/PAA (50% AA) | 150 | 161 |
| PEU/PAA (70% AA) | 110 | 141 |
| PBS bath | 300 | 600 |

The results show that the resistances of the semi-IPNs are lower than (but within the same order of magnitude as) pure PBS fluid alone. The limit of the ohm meter was 40,000 ohms. Typical values for insulators (including polyurethanes) are $10^{14}$-$10^{16}$ ohms; therefore, the resistance values of the PEU alone were outside the range of the meter used. Permeability of the PEU/PAA semi-IPN was measured using a device similar to the one described by Maroudas et al. in Permeability of articular cartilage. Nature, 1968. 219(5160): p. 1260-1. The permeability was calculated according to Darcy's Law (Q=KA$\Delta$p/L), where Q is the flow rate [mm$^3$/sec], A the cross-sectional area of the plug [mm$^2$], $\Delta$p the pressure gradient applied [MPa] (pressurized fluid), L is the thickness of the hydrogel. The permeability of the PEU/PAA semi-IPN prepared from 70% acrylic acid was found to be K=1.45×$10^{-17}$ m$^4$/N*sec. For natural cartilage, literature values range from 1.5×$10^{-16}$ to 2×$10^{-15}$ m$^4$/N*sec. Therefore, the PEU/PAA is 10-100 times less permeable than cartilage, which may make it less prone to dehydration under prolonged compressive loads compared to natural cartilage. The permeability of the IPN can be tuned by varying the concentration of AA in the swelling solution; the higher the AA content, the higher the permeability. In contrast, the unmodified PEU material alone is effectively impermeable to solutes; although it retains some moisture (~1%), in practice it does not act as a solute-permeable matrix.

Other variations and modifications to the above compositions, articles and methods include:

The first polymer can be one that is available commercially or custom-made and made by a number of ways (e.g., extruded, injection molded, compression molded, reaction injection molded (RIM) or solution-casted.) The first polymer can be uncrosslinked or crosslinked by various means. Either polymer can be crosslinked by, e.g., gamma radiation or electron beam radiation.

Any number or combinations of ethylenically unsaturated monomers or macromonomers (e.g., containing reactive double bonds) can be used as the basis of the second or subsequent network so long as the total contains at least 2% by weight ionizable chemical groups. These include but are not limited those containing vinyl, acrylate, methacrylate, allyl ether, or acrylamide groups. And number of pendant functional groups can be conjugated to these ethylenically unsaturated groups including but not limited to carboxylic acid, sulfonic acid, acetates, alcohols, ethers, phenols, aromatic groups, or carbon chains.

The polyurethane-based polymer can be (but is not limited to) the following: polyether urethane, polycarbonate urethane, polyurethane urea, silicone polyether urethane, or silicone polycarbonate urethane. Other polyurethanes with other hard segments, soft segments, and chain extenders are possible.

Other polymers can be used in the first network, such as homopolymers or copolymers of silicone (polydimethylsiloxane) or polyethylene.

When a polyurethane-based polymer is used as the first polymer, the extent of physical and chemical crosslinking of the polyurethane-based polymer can be varied between physical crosslinking-only (thermoplastic) to extensive chemical crosslinking. In the case of chemical crosslinking, the crosslinkable polyurethane can be used alone or as a mixture with thermoplastic (uncrosslinked) polyurethane.

The conditions of polymerization (i.e., ambient oxygen, UV intensity, UV wavelength, exposure time, temperature) may be varied.

The orientation and steepness of the composition gradients can be varied by various means such as time and/or method of immersion in the monomer, and the application of external hydrostatic positive or negative pressure.

The thermoplastic can be made porous by various techniques such as foaming or salt-leaching. After swelling of the porous polymer (such as PU) with a monomer (such as AA) followed by polymerization or AA, a porous IPN is formed.

Additional layers of thermoplastics can be added to material on either the IPN side or the thermoplastic side-only by curing or drying the new thermoplastic to the surface. The layers can all be the same material or be different materials (e.g. ABS+polyurethane, polyether urethane+polycarbonate urethane, etc.

A number of different solvents can be used during the synthesis of the polyurethane, the second network, or both, including but not limited to dimethylacetamide, tetrahydrofuran, dimethylformamide, ethanol, methanol, acetone, water, dichloromethane, propanol, methanol, or combinations thereof.

Any number of initiators can be used such as photoinitiators (e.g., phenone-containing compounds and Irgacure® products), thermal initiators, or chemical initiators. Examples of thermal initiators include but are not limited to azo-compounds, peroxides (e.g., benzoyl peroxide), persulfates (e.g., potassium persulfate or ammonium persulfate), derivatives, or combinations thereof.

Variations of the crosslinking identity and density (e.g. 0.0001%-25% by mole crosslinking agent with respect to the monomer), initiator concentration (e.g. 0.0001%-10% by mole with respect to the monomer) molecular weight of precursor polymers, relative weight percent of polymers, light wavelength (UV to visible range), light intensity (0.01 $mW/cm^2$-1 $W/cm^2$), temperature, pH and ionic strength of swelling liquid, and the level of hydration.

The second network material can be synthesized in the absence of a crosslinking agent.

The water content of these materials can range between 2% to 99%.

Different components of the IPN can be incorporated in combination with ionizable monomers, such as poly(vinyl alcohol), poly(ethylene glycol)-acrylate, poly(2-hydroxyethylacrylate), poly(2-hydroxyethylmethacrylate), poly(methacrylic acid), poly(2-acrylamido-2-methyl propane sulfonic acid), other vinyl-group containing sulfonic acids, poly(acrylamide), poly(N-isopropylacrylamide) poly(dimethacrylamide), and combinations or derivatives thereof. For instance, a copolymer of acrylic acid and vinyl sulfonic acid or 2-acrylamido-2-methyl propane sulfonic acid can be created for the second network to form a polyurethane first network and a poly(acrylic acid-co-acrylamido-methyl-propane sulfonic acid) copolymeric second network. Any monomer or combination of monomers can be used in conjunction with a suitable solvent as long as they contain at least 2% by weight ionizable monomer and are able to enter (swell) the first polymer.

The IPN can have incorporated either chemically or physically within its bulk or its surface certain additives such as antioxidants (e.g., Vitamin C, Vitamin E, Irganox®, or santowhite powder) and/or anti-microbial agents (e.g., antibiotics). These can be chemically linked to the material by, for example, esterification of the anti-oxidant with any vinyl-group containing monomer such as methacrylate, acrylate, acrylamide, vinyl, or allyl ether.

More than two networks (e.g., three or more) can also be formed, each of which are either crosslinked or uncrosslinked.

The polyurethane itself can be modified in a number of ways, such as by sulfonation at the urethane group by reaction of 1,3 propane sulfone in the presence of sodium hydride, or the formation of allophanate linkages at the urethane group by reaction with excess isocyanate groups. For instance, excess isocyanatoethyl methacrylate can be reacted with polyurethane in toluene in the presence of dibutyltin dilaurate for 2.5 hours to yield a methacryloxy-conjugated polyurethane surface. The methacryloxy groups can then be used subsequently tether other methacryloxy (or other vinyl group)-containing monomers or macromonomers via free radical polymerization. Such modifications can be carried out before or after the formation of the second network of the IPN.

EXAMPLES

Example 1

In one example, a polycarbonate urethane (Bionate 55 D) was immersed in 70% acrylic acid in water containing 0.1% v/v 2-hydroxy-2-methyl propiophenone and 0.1% v/v triethylene glycol dimethacrylate with respect to the monomer overnight. The polycarbonate urethane was removed from the solution, placed between two glass slides, and exposed to UV light (2 $mW/cm^2$) for 15 minutes. The resulting semi-IPN was removed, and washed and swollen in phosphate buffered saline. The material swelled and became lubricious within hours. In other examples, segmented polyurethane urea, as well as silicone polyether urethane and silicone polycarbonate urethanes were placed in acrylic acid solutions and polymerized and washed in the same fashion to yield a lubricious IPN.

Example 2

In another example, a polyether urethane (Elasthane™ 55 D) was immersed in 70% acrylic acid in water containing 0.1% v/v 2-hydroxy-2-methyl propiophenone and 0.1% v/v triethylene glycol dimethacrylate with respect to the monomer overnight. The polyether urethane was removed from the solution, placed between two glass slides, and then exposed to UV light (2 $mW/cm^2$) for 15 minutes. The resulting semi-IPN was removed and then washed and swollen in phosphate buffered saline. The material swelled and became lubricious within hours. In other examples, polycarbonate urethane, segmented polyurethane urea, as well as silicone polyether urethane and silicone polycarbonate urethanes were placed in acrylic acid solutions and polymerized and washed in the same fashion to yield lubricious IPNs.

Example 3

In another example, silicone polyether urethane and silicone polycarbonate urethanes were separately placed overnight in 100% acrylic acid solutions, to which were added 0.1% v/v 2-hydroxy-2-methyl propiophenone and 0.1% v/v triethylene glycol dimethacrylate with respect to the monomer. After polymerization and crosslinking, the semi-IPNs swelled and became lubricious. The addition of silicone (polydimethylsiloxane) in the polyurethane adds an extra level of biostability to the material as well as potentially useful surface chemistry and properties.

Example 4

In another example, a methacryloxy-functionalized polycarbonate urethane was exposed to UV light to crosslink the polycarbonate urethane, and then swollen in 70% acrylic acid with 0.1% v/v 2-hydroxy-2-methyl propiophenone and 0.1% v/v triethylene glycol dimethacrylate with respect to the monomer overnight. The material was removed from the solution, placed between two glass slides, and then exposed to UV light (2 $mW/cm^2$) for 15 minutes to yield a fully interpenetrating polymer network of the polycarbonate urethane and poly(acrylic acid.) The IPN was then washed in an aqueous salt solution to neutralize the poly(acrylic acid), achieve equilibrium swelling, and remove any unreacted monomers.

Example 5

In another example, a methacryloxy-functionalized polyether urethane was exposed to UV light (in the presence of 0.1% 2-hydroxy-2-methyl propiophenone and 0.1% triethylene glycol dimethacrylate) to crosslink the polyetherurethane, and then was swollen in 70% acrylic acid with the aforementioned photoinitiator and crosslinker followed by UV-initiated crosslinking to yield a fully interpenetrating polymer network of the polyetherurethane and poly(acrylic acid.) The IPN was then washed in an aqueous salt solution to neutralize the poly(acrylic acid), achieve equilibrium swelling, and remove any unreacted monomers.

Example 6

In another example, a 25% solution of methacryloxy-functionalized polycarbonate urethane in DMAC along with 0.1% of the aforementioned photoinitiator was exposed to UV light to crosslink the polycarbonate urethane. After removing the solvent in a heated (60° C.) convection oven, an additional layer of polycarbonate urethane was then cast on one side of the crosslinked polycarbonate urethane to yield a laminate structure and then only the crosslinked side was swollen in 70% acrylic acid with the 0.1% 2-hydroxy-2-methyl propiophenone and 0.1% triethylene glycol dimethacrylate followed by UV-initiated crosslinking to yield a fully interpenetrating polymer network of the polycarbonate urethane and poly(acrylic acid.) The IPN was then washed in an aqueous salt solution to neutralize the poly(acrylic acid), achieve equilibrium swelling, and remove any unreacted monomers.

Example 7

In another example, a 25% solution of methacryloxy-functionalized polycarbonate urethane in DMAC along with 0.1% of the aforementioned photoinitiator was exposed to UV light to crosslink the polyether urethane. After removing the solvent in a heated (60° C.) convection oven, an additional layer of polyether urethane was then cast on one side of the crosslinked polycarbonate urethane to yield a laminate structure and then only the crosslinked side was swollen in 70% acrylic acid with 0.1% 2-hydroxy-2-methyl propiophenone and 0.1% triethylene glycol dimethacrylate followed by UV-initiated crosslinking to yield a fully interpenetrating polymer network of the polyether urethane and poly(acrylic acid.) The IPN was then washed in an aqueous salt solution to neutralize the poly(acrylic acid), achieve equilibrium swelling, and remove any unreacted monomers.

Example 8

In another set of examples, a layer of methacryloxy-functionalized polyether urethane was cast onto a layer of injection molded polyether urethane, and separately, another layer was cast onto a layer of injection molded polycarbonate urethane. Each was exposed to UV light, to yield laminate structures. Only the crosslinked sides were swollen in 70% acrylic acid with 0.1% 2-hydroxy-2-methyl propiophenone and 0.1% triethylene glycol dimethacrylate followed by UV-initiated crosslinking to yield a fully interpenetrating polymer networks. The IPNs were then washed in an aqueous salt solution to neutralize the poly(acrylic acid), achieve equilibrium swelling, and remove any unreacted monomers.

Example 9

In one example, acrylonitrile butadiene styrene (ABS) was exposed to 100% acrylic acid in water containing 0.1% v/v 2-hydroxy-2-methyl propiophenone and 0.1% v/v triethylene glycol dimethacrylate with respect to the monomer for 15 minutes. The surface-exposure was accomplished by drop-casting the monomer solution on the surface of the ABS for 30 minutes. The ABS was then placed between two glass slides, and then exposed to UV light (2 mW/cm2) for 15 minutes. The resulting ABS/PAA gradient IPN was removed and then washed and swollen in phosphate buffered saline. The IPN was washed in an aqueous salt solution to neutralize the poly(acrylic acid), achieve equilibrium swelling, and remove any unreacted monomers. The material swelled and became lubricious within hours.

Example 10

To reshape the thermoplastic gradient IPNs, heat was applied. An ABS/PAA gradient IPN was heated using a heat gun and then laid on a cylindrical polypropylene tube. After letting the material cool to room temperature, acetone was injected between the ABS/PAA and the thermoplastic gradient IPN wrapped around and bonded to a polypropylene tube. After applying manual pressure and allowing the sample to dry, the result was a thermoplastic gradient IPN wrapped around and bonded to a polypropylene tube.

Example 11

In another example, a thermoplastic gradient ABS/PAA IPN was attached to polycarbonate urethane by injecting acetone between the ABS and polycarbonateurethane and applying manual pressure to yield a thermoplastic gradient IPN bonded to a polycarbourethane.

Example 12

In another example, a curved polycarbonate urethane IPN was made straight again by applying heat on the polyurethane side using a heat gun, manually reversing the curvature of the material, and cooling the IPN in water.

Example 13

In another example, a polyether urethane solution (e.g. 20% in dimethylacetamide ("DMAC")) was cast on top of a polycarbonate urethane in a laminate structure, allowed to dry in a heated (60° C.) convection oven, and then only the polyether urethane surface was exposed to 70% acrylic acid in water containing 0.1% v/v 2-hydroxy-2-methyl propiophenone and 0.1% v/v triethylene glycol dimethacrylate with respect to the monomer for 15 minutes. The surface-exposure was accomplished by laying the laminate material polyether urethane-side down on a bed of fabric that was soaked in the aforementioned monomer solution. The material was removed from the fabric mat, placed between two glass slides, and then exposed to UV light (2 mW/cm$^2$) for 15 minutes. The resulting gradient semi-IPN was removed, washed and swollen in phosphate buffered saline. The material swelled and became lubricious within hours. In other examples, polyether urethane, segmented polyurethane urea, silicone polyether urethane, and silicone polycarbonate urethane were handled the same way to yield a lubricious semi-IPNs.

Example 14

In another example, a layer of polycarbonate urethane (20% in DMAC) containing 50% by weight sodium chloride was solution cast on a premade polyether urethane-polycarbonate urethane and dried at 80° C. under convection. The salt was washed away in water to yield a porous side on the laminated polyurethane. Other materials have been made with sodium chloride concentrations varying between 10% and 80%

Example 15

In another example, a layer of polycarbonate urethane (20% in DMAC) containing 20% tricalcium phosphate was solution cast on a premade polyether urethane-polycarbonate urethane and dried at 80° C. under convection. The tricalcium phosphate was left embedded within the polyurethane as an osteoconductive agent. Other materials have been made with tricalcium phosphate concentrations varying from 0.001%-20%

Example 16

In another example, a polyurethane urea (e.g. 20% in dimethylacetamide) was cast on top of a polycarbonate urethane in a laminate structure, and then only the polyurethane urea surface was exposed to 70% acrylic acid in water containing 0.1% v/v 2-hydroxy-2-methyl propiophenone and 0.1% v/v triethylene glycol dimethacrylate with respect to the monomer for 15 minutes. The surface-exposure was accomplished by laying the laminate material polyurethane urea-side down on a bed of fabric that was soaked in the aforementioned monomer solution. The polycarbonate urethane was removed from the fabric mat, placed between two glass slides, and then exposed to UV light (2 mW/cm$^2$) for 15 minutes. The resulting gradient semi-IPN was removed and then washed and swollen in phosphate buffered saline. The material swelled and became lubricious within hours. The material was washed in PBS to neutralize the poly(acrylic acid), achieve equilibrium swelling, and remove any unreacted monomers.

Example 17

In another example, a methacryloxy-functionalized polyether urethane mixed with a thermoplastic polyether urethane in solution (25% in dimethylacetamide) was exposed to UV light to crosslink the polycarbonate urethane. An additional layer of polyether urethane was then cast on one side of the crosslinked polyether urethane to yield a laminate structure and then only the crosslinked side was swollen in 70% acrylic acid with the aforementioned photoinitiator and crosslinker, followed by UV-initiated crosslinking to yield a fully interpenetrating polymer network of the polyether urethane and poly(acrylic acid.) The IPN was then washed in an aqueous salt solution to neutralize the poly(acrylic acid), achieve equilibrium swelling, and remove any unreacted monomers.

Example 18

In one example, flat sheets were created by solution casting of thermoplastic polyurethanes in (dimethylacetamide (DMAC). Polyurethane solutions of polyether urethane (Elasthane™), polycarbonate urethane (Bionate), polyether urethane urea (Biospan), silicone polycarbonate urethane (Carbosil), and silicone polyether urethane (Pursil) were synthesized in dimethylacetamide (DMAC) at solids concentrations of about 25% by the manufacturer.

Example 19

Spherical shapes were cast by dip-coating glass as well as silicone spheres in polyurethane solutions (in DMAC). Polycarbonate urethane (20% in DMAC) was dip coated onto a spherical glass mold (49.5 mm outer diameter), and separately, onto a silicone sphere. The solvent was removed by drying at 80° C. in a convection oven. This process was repeated two more times to create three total coatings. Then, the sphere was dip coated in polyether urethane (20% in DMAC) and then dried at 80° C. under convection. This process was also repeated two more times. The resulting capped-shaped, laminate polyurethane was removed from the mold, and its outer side immersed in a 70% acrylic acid solution in water, with 0.1% 2-hydroxy-2-methyl-propiophenone and 0.1% triethylene glycol dimethacrylate for 1.5 hours. The cap was inverted, placed back over a spherical glass mold, and exposed to UV light (2 mW/cm$^2$) for 15 minutes. Next the cap was removed from the mold and placed in phosphate buffered saline. The result was a spherical, gradient IPN with one lubricious surface and one pure thermoplastic surface. Other temperatures and other solvents can also be used to carry out this process, as well as other mold materials and polymer components.

Example 20

In another example, a polyether urethane was swollen in 70% acrylic acid with 0.1% 2-hydroxy-2-methyl propiophenone and 0.1% methylene bisacrylamide. One side of the material was dabbed dry, and then exposed to air and treated with UV light. The resulting gradient semi-IPN was then washed in an aqueous salt solution to neutralize the poly(acrylic acid), achieve equilibrium swelling, and remove any unreacted monomers. In other experiments, the material was exposed to nitrogen or argon during curing.

Example 21

In another example, a polyether urethane (Elasthane™ 55 D) was injection molded and then swollen in 70% acrylic acid with 0.1% v/v 2-hydroxy-2-methyl propiophenone and 0.1% w/w methylene bisacrylamide followed by UV-initiated crosslinking to yield a fully interpenetrating polymer network of the polyether urethane and poly(acrylic acid). The JPN was then washed in an aqueous salt solution to neutralize the poly(acrylic acid), achieve equilibrium swelling, and remove any unreacted monomers.

Example 22

In another example, a polyether urethane (Elasthane™ 75 D) was injection molded, dip-casted (solution casted) on one side in a polyether urethane solution (Elasthane™ 55 D in 25% DMAC) and dried in a convection oven to remove the DMAC solvent. The dried material was swollen in 70% acrylic acid with the 70% acrylic acid with 0.1% v/v 2-hydroxy-2-methyl propiophenone and 0.1% w/w methylene bisacrylamide followed by UV-initiated crosslinking to yield a fully interpenetrating polymer network of the polyether urethane and poly(acrylic acid). The IPN was then washed in an aqueous salt solution to neutralize the poly (acrylic acid), achieve equilibrium swelling, and remove any unreacted monomers.

Example 23

In another example, a polycarbonate urethane (Bionate 75 D) was injection molded, dip-casted (solution casted) on one side in a polyether urethane solution (Elasthane™ 55 D in 25% DMAC) and dried in a convection oven to remove the DMAC solvent. The dried material was swollen in 70% acrylic acid with 0.1% v/v 2-hydroxy-2-methyl propiophenone and 0.1% w/w methylene bisacrylamide followed by UV-initiated crosslinking to yield a fully interpenetrating polymer network of the polyether urethane and poly(acrylic acid). The IPN was then washed in an aqueous salt solution to neutralize the poly(acrylic acid), achieve equilibrium swelling, and remove any unreacted monomers.

Example 24

In another example, a polyether urethane (Elasthane™ 75 D) was injection molded and then dip-casted (solution casted) in a methacryloxy-functionalized polyether urethane solution (Elasthane™ 55 D in 25% DMAC) along with the aforementioned photoinitiator and then was exposed to UV light to crosslink the methacryloxy-functionalized polyether urethane. The material was then dried in a convection oven to remove the DMAC solvent. The dried material was then swollen in 70% acrylic acid with the 0.1% v/v 2-hydroxy-2-methyl propiophenone and 0.1% w/w methylene bisacrylamide followed by UV-initiated crosslinking to yield a fully interpenetrating polymer network of the polyether urethane and poly(acrylic acid). The IPN was then washed in an aqueous salt solution to neutralize the poly(acrylic acid), achieve equilibrium swelling, and remove any unreacted monomers.

Example 25

In another example, a polycarbonate urethane (Bionate 75 D) was injection molded and then dip-casted (solution casted) in a methacryloxy-functionalized polyether urethane solution (Elasthane™ 55 D in 25% DMAC) and then was exposed to UV light to crosslink the methacryloxy-functionalized polyether urethane. The material was then dried in a convection oven to remove the DMAC solvent. The dried material was then swollen in 70% acrylic acid with the 0.1% v/v 2-hydroxy-2-methyl propiophenone and 0.1% v/v triethylene glycol dimethacrylate followed by UV-initiated crosslinking to yield a fully interpenetrating polymer network of the polyether urethane and poly(acrylic acid). The IPN was then washed in an aqueous salt solution to neutralize the poly(acrylic acid), achieve equilibrium swelling, and remove any unreacted monomers.

Example 26

In another example, a polyether urethane (Elasthane™ 55 D) solution casted and then swollen in 35% sulfopropyl methacrylate in acetic acid with 0.1% v/v 2-hydroxy-2-methyl propiophenone and 0.1% w/w methylene bisacrylamide followed by UV-initiated crosslinking to yield a fully interpenetrating polymer network of the polyether urethane and poly(acrylic acid). The semi-IPN was then washed with water to remove the acetic acid, and then in an aqueous salt solution to neutralize the poly(acrylic acid), achieve equilibrium swelling, and remove any unreacted monomers.

Example 27

In another example, a polyether urethane (Elasthane™ 55 D) solution casted and then swollen in 35% sulfopropyl methacrylate and 35% acrylic acid in water with the 0.1% v/v 2-hydroxy-2-methyl propiophenone and 0.1% w/w methylene bisacrylamide followed by UV-initiated crosslinking to yield a fully interpenetrating polymer network of the polyether urethane and poly(acrylic acid). The semi-IPN was then washed in an aqueous salt solution to neutralize the poly(acrylic acid)/poly(sulfopropyl methacrylate) copolymer, achieve equilibrium swelling, and remove any unreacted monomers.

Example 28

In another example, a rectangular sample of PMMA (plexiglass) was swollen briefly in 100% acrylic acid in water with the 0.1% v/v 2-hydroxy-2-methyl propiophenone and 0.1% w/w methylene bisacrylamide followed by UV-initiated crosslinking to yield a fully interpenetrating polymer network of the PMMA and poly(acrylic acid). The IPN was then washed in an aqueous salt solution to neutralize the poly(acrylic acid), achieve equilibrium swelling, and remove any unreacted monomers.

Example 29

In another example, a rectangular specimen of polydimethyl sulfoxide (PDMS, Sylgard® 184) was prepared according to the manufacturer's specifications and then was swollen briefly in a 35% acrylic acid solution in tetrahydrofuran along with 0.1% v/v 2-hydroxy-2-methyl propiophenone and 0.1% v/v triethylene glycol dimethacrylate, followed by UV-initiated crosslinking to yield a fully interpenetrating polymer network of the PDMS and poly (acrylic acid). The IPN was washed in an aqueous salt solution to neutralize the poly(acrylic acid), achieve equilibrium swelling, and remove any unreacted monomers.

Example 30

Figure 35:
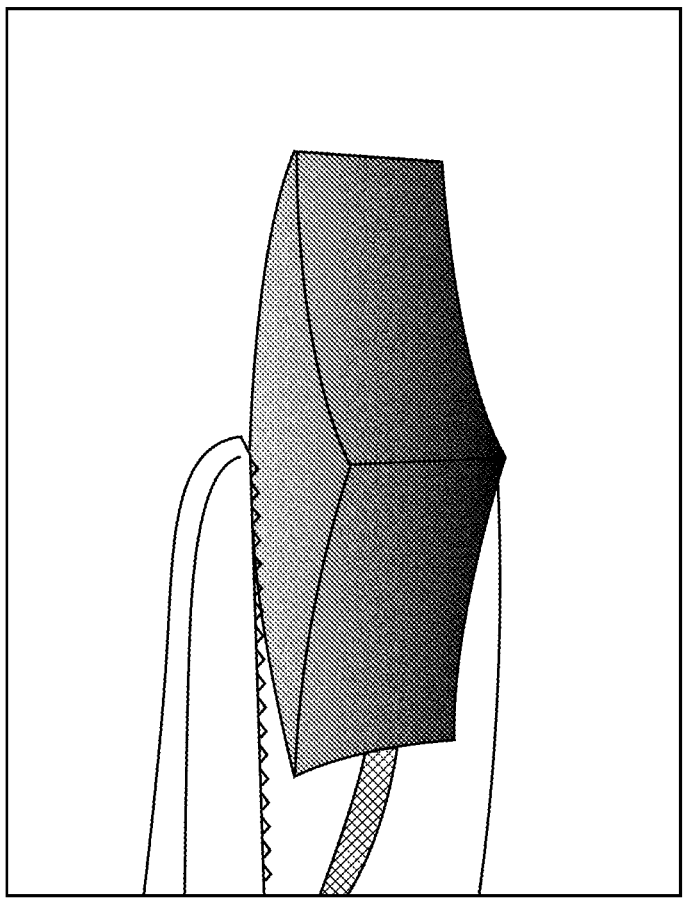
FIG. 35 is a photograph of a hydrated PEU/PAA semi-IPN gradient material being held by a forceps.

FIG. 35 is a cross-section of a hydrated arthroplasty device and shows that the arthroplasty device is, in effect, a synthetic version of an osteochondral graft that emulates the structure, elastic modulus, fracture strength, and lubricious surface of natural cartilage on one side and the stiffness, strength, and porosity of trabecular bone on the other side. The device is comprised of a composite gradient material featuring a lubricious, cartilage-like polymer that smoothly transitions into a stiff, porous, bone-like anchoring surface. The gradient was designed to mimic the compositional gradient inherent to natural joints, in which compliant, slippery cartilage becomes progressively more hard and bone-like from superficial to deep along the thickness direction. In practice, this "biomimetic" gradient should yield a physiologic stress distribution over the underlying bone while also minimizing micromotion at the bone interface by effectively matching the stiffnesses of the device and bone at their point of contact. Suitable materials are described, e.g., in the following, the disclosures of which are incorporated herein by reference: U.S. Patent Appl. Ser. 61/079,060 (filed Jul. 8, 2008); U.S. Patent Appl. Ser. 61/095,273 (filed Sep. 8, 2008); and U.S. patent application Ser. No. 12/148,534 (filed Apr. 17, 2008).

Example 31

Figure 36:
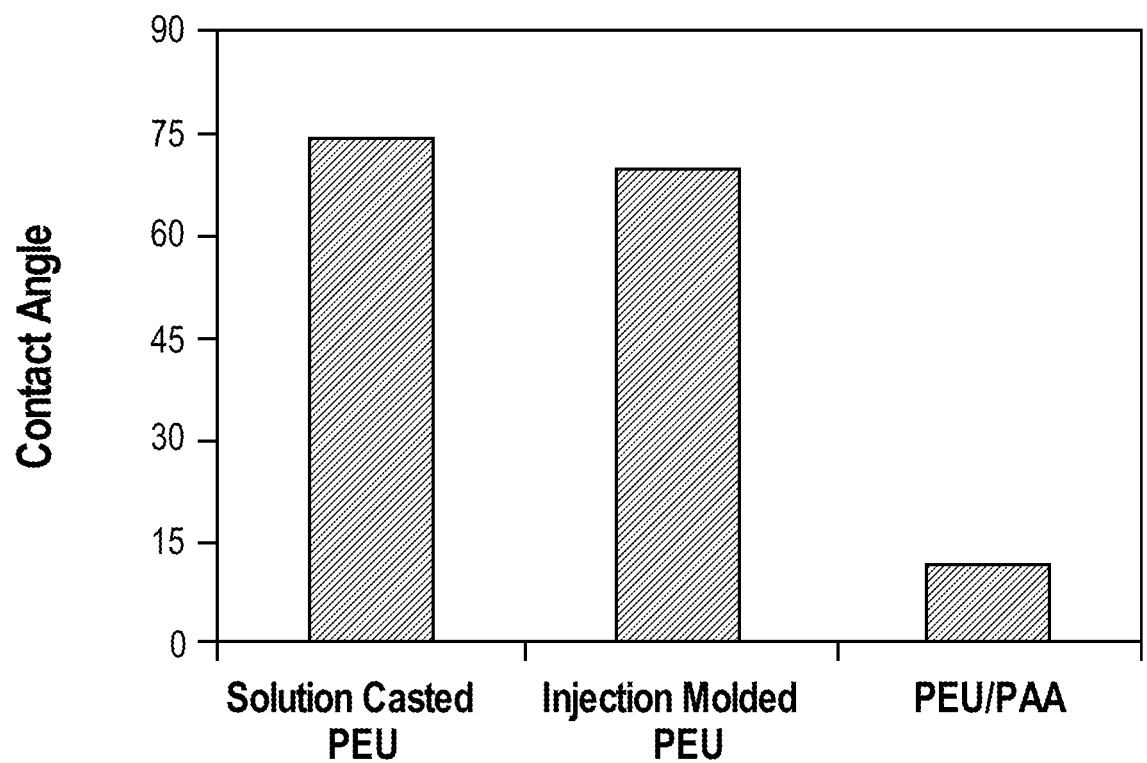
FIG. 36 shows contact angle analysis in association with Example 32.

FIG. 36 shows contact angle analysis indicating that the material of this invention is very hydrophilic. When a drop of water is placed on a surface, the shape the drop takes is dependent on the composition of the surface. A hydrophilic surface attracts the water and creates a flatter drop, while a hydrophobic surface repels the water and creates a rounder drop. The degree of hydrophilicity of the surface is inferred by measuring the angle created between the surface and the drop of water, referred to as the contact angle. Typically, a more hydrophilic surface will have a contact angle of about 0-45° with water, while a more hydrophobic surface will have a contact angle greater than 45° with water.

The contact angle between the charged hydrogel IPN made by this invention and water was determined. Briefly, a sheet of Elasthane™ 55 D (polyetherurethane) was soaked in acrylic acid with initiator and cross-linker, and cured to form a semi-IPN (PEU/PAA semi IPN). After curing, the charged PEU/PAA semi IPN was hydrated in phosphate buffered saline. The material was removed from the solution and its surface briefly dabbed to remove any residual liquid. A drop of water was placed on the surface of the material, and the contact angle read using a Goniometer. The results showed a contact angle of approximately 8°. For comparison, readings taken on starting materials of solution-casted polyurethanes and injection-molded polyurethane had contact angles of approximately 72° and 69°, respectively. This result demonstrates that the incorporation of a poly(acrylic acid) network into polyurethane according to the current invention dramatically increases surface hydrophilicity.

Example 32

Figure 37B:
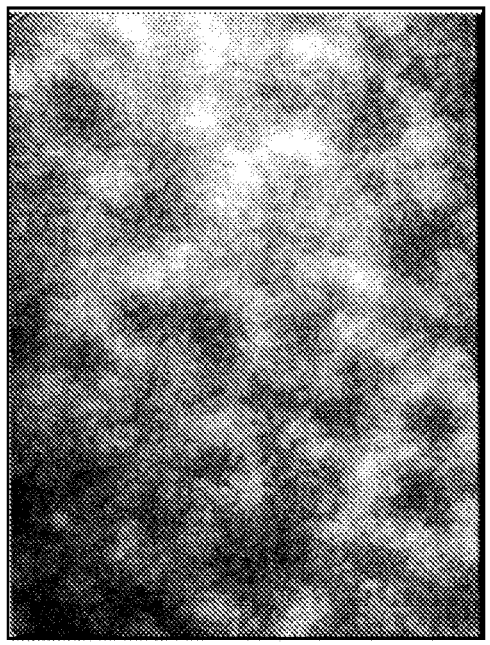
FIGS. 37A-B show the PEU/PAA semi-IPN material subject to Transmission Electron Microscopy analysis as associated with Example 33.
Figure 37A:
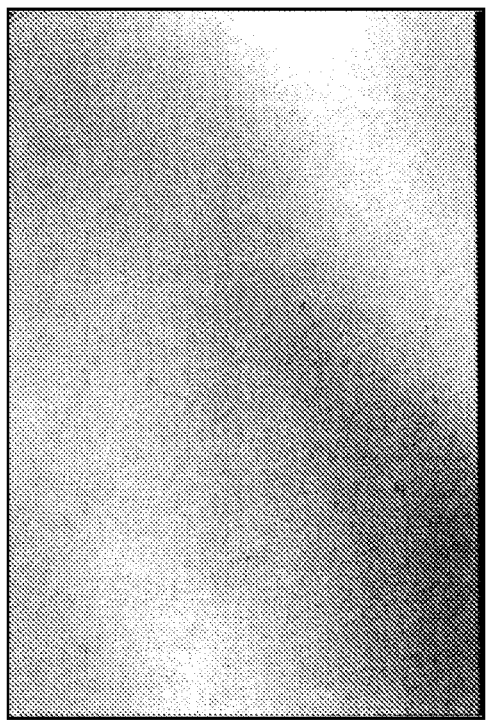

The differences in the structures of the charged hydrogel IPN and polyurethane are shown by Transmission Electron Microscopy (TEM). TEM creates a highly magnified image of a material. TEM was performed on samples of polyetherurethane/poly(acrylic) acid semi IPN (PEU/PAA semi IPN) of the current invention and of unmodified polyetherurethane. Briefly, a sheet of Elasthane™ 55 D (polyetherurethane) was soaked in acrylic acid with initiator and cross-linker, and cured. It was stained with osmium tetroxide per standard procedures to perform TEM analysis. FIG. 37A shows a 34 kX magnification image of PEU while FIG. 37B shows the PEU/PAA semi-IPN. The sizes of light and dark regions, corresponding to the amorphous (soft) and ordered (hard) domains, are increased in the TEM images of the PEU/PAA semi-IPN relative to the unmodified PEU. The PAA appears sequestered within the PEU soft segments. on the basis of the larger domain sizes in the PEU/PAA sample compared to the PEU sample, the degree of phase separation is greater in the PEU/PAA sample compared to the unmodified PEU.

Example 33

FIG. 38 shows a TEM of the same PEU/PAA semi-IPN material as FIG. 37 at 12.4 kX magnification. The schematic illustrates how the hard segments are phase separated from the soft segments of the interpenetrated polymer network.

Example 34

Figure 39:
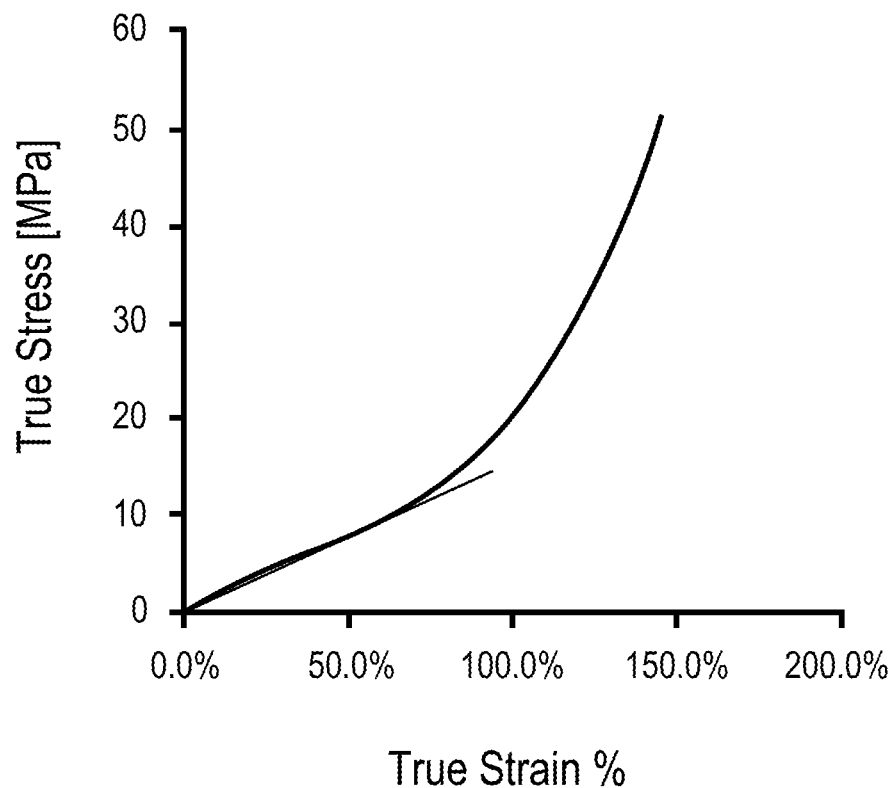
FIG. 39 shows the tensile stress-strain behavior of the PEU/PAA semi-IPN material associated with Example 35.

FIG. 39 shows the static mechanical properties of the PEU/PAA IPN which comprises an exemplary joint interface surface of an orthopaedic implant. Uniaxial tensile tests were conducted to determine the initial Young's modulus in tension, the strain-at-break, and stress-at-break of the materials. Dog bone specimens were tested according to ASTM D638, at a strain rate of 0.3%/sec. The average true stress-true strain curve for the material of the joint interface material is presented in FIG. 40. In the linear portion of the curve, the elastic modulus (as provided from the true stress, true strain curve) is E=15.3 MPa which is very close to the tensile properties reported for natural cartilage. The ultimate true stress was found to be at approximately $\sigma_{ult}$=52 MPa at $\varepsilon_{ult}$=143% true strain (of note, cartilage is found to fail at around 65% strain). Strain hardening under tension was observed for true strains of 80% and higher. The Poisson's ratio (equilibrium) was estimated by measuring the lateral contraction of the dog bone neck region and was found to be consistent along the strain range at v=0.32. The bulk modulus was therefore calculated from the equation K=E/3(1−2v) and was found to be 18.3 MPa. Unconfined compression plug tests according to ASTM D695 reveal that PEU/PAA semi-IPN has excellent compressive properties, with a compressive stiffness modulus of 15.6 MPa (same as the tensile modulus, based on true stress-strain) and a failure strength that is higher than 50 MPa.

Example 35

Figure 40:
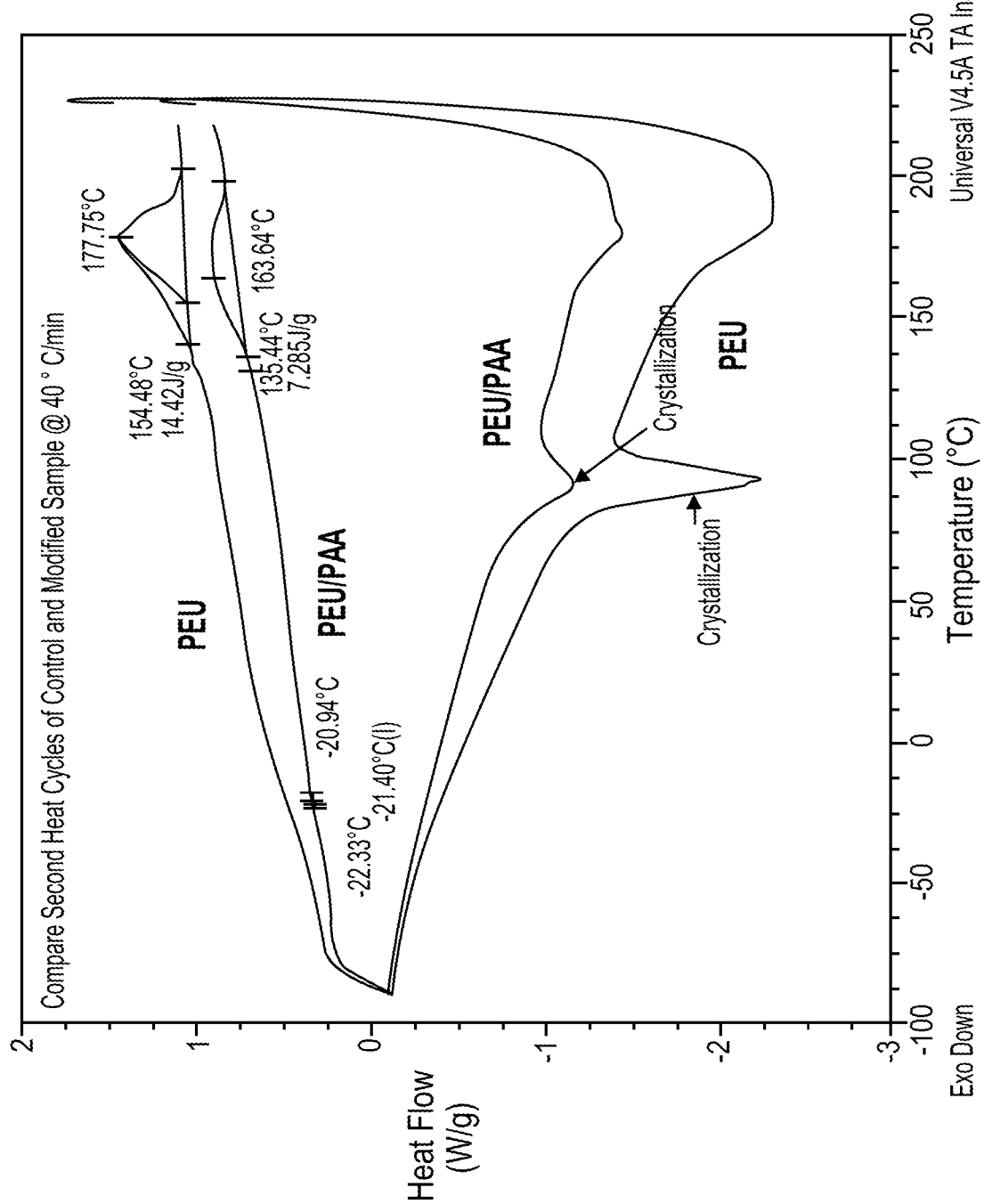
FIG. 40 shows the thermogram of the PEU/PAA semi-IPN material analyzed by DSC associated with Example 36.

FIG. 40 shows the thermal curves of PEU and PEU/PAA semi-IPN samples evaluated by Differential Scanning calorimetry (DSC) at a heating rate of 40° C. per minute. FIG. 41 compares the thermal transitions of PEU and PEU/PAA semi-IPN samples evaluated by DSC at two different heating rates. The thermal transition temperatures including the glass transition temperature $T_g$, the crystallization temperature, and the melting temperature $T_m$ were determined. Below its $T_g$, the heat capacity of the polymer is lower and the polymer is harder or glassier. Above the $T_g$, the heat capacity of the polymer increases and the polymer becomes more flexible. Above this temperature, for some polymers is the crystallization temperature and at least some of the domains of the molecule become more organized, and essentially crystalline. At a higher temperature is the melting temperature when the crystalline portions completely melt. The procedure was done following ASTM D3418-03 test method using a TA Instruments Q200 DSC system with a Modulated Differential Scanning calorimeter and Refrigerated Cooling System (RCS90). Briefly, a sheet of Elasthane™ 55 D (polyetherurethane) was soaked in acrylic acid with an initiator and cross-linker and then cured. A small amount (2-6 mg) of PEU/PAA semi-IPN sample was placed into a first aluminum pan. A cover was placed on the top of the pan and crimped with a Universal Crimping press to sandwich the sample between pan and cover. Heat was applied to the first pan and, separately, to a reference pan, and the current flow to each was changed to keep the temperatures of the two materials the same. The heat flow of the material being tested was graphed against the temperature and the slopes of the curves indicate the thermal transition temperatures (FIG. 40). Several tests were performed, using different rates of heating (10° C. and 40° C. per minute). By performing the tests at different rates of heating, different resolution is obtained for the thermal transitions, as seen in FIG. 41. Because the $T_g$ can depend on the previous thermal history of the material, the material is subjected to two heat cycles. The first heat cycle is used to standardize the conditions under which the polymer arrives at its test state, and the second test cycle is used to generate transition temperatures. The glass transition temperatures, $T_g$, for both the PEU/PAA semi IPN and the PEU were around 21° C. when the rate of heating was kept at 10° C. per minute. The crystallization and melting temperatures were lower in the PEU/PAA compared with the PEU. At a heating rate of 40° C. per minute, the crystallization temperatures were 90° C. for the PEU/PAA compared with 93° C. for the PEU. When the heating rate was slowed to 10° C. per minute, the crystallization temperatures observed were 79° C. for the PEU/PAA compared with 92° C. for the PEU. Finally, at a heating rate of 40° C. per minute, the Tm temperatures were 164° C. for the PEU/PAA compared with 178° C. for the PEU. When the heating rate was slowed to 10° C. per minute, the $T_m$ temperatures observed were 154° C. for the PEU/PAA with 176 and 186° C. for the PEU. In some analyses of the PEU, two $T_m$'s were observed (176° C. and 186° C.), which may be due to different segments in the polymer. The change of the $T_m$ is due at least in part to an increase in polymer volume caused by the addition of the PAA, leading to fewer hard segments per volume of polymer.

Example 36

Figure 42:
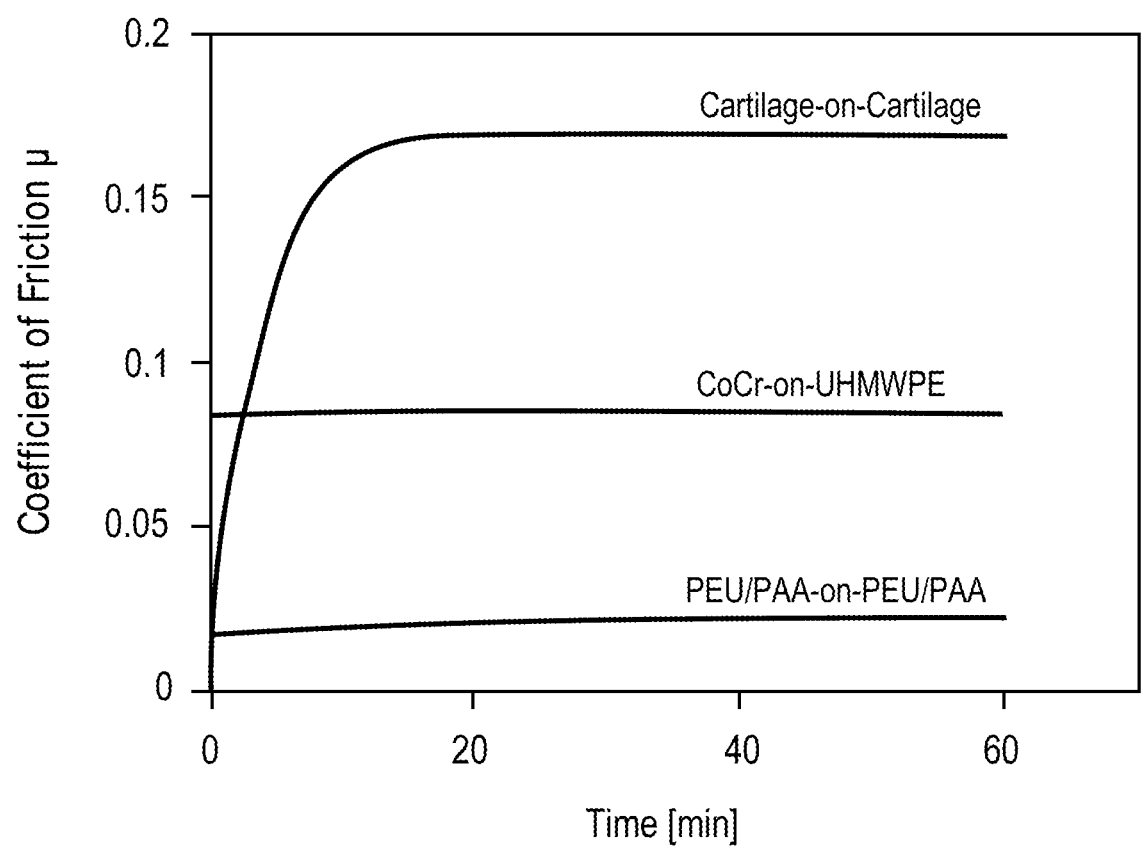
FIG. 42 shows the coefficient of friction of the PEU/PAA semi-IPN material on PEU/PAA under static load associated with Example 37.
Figure 43:
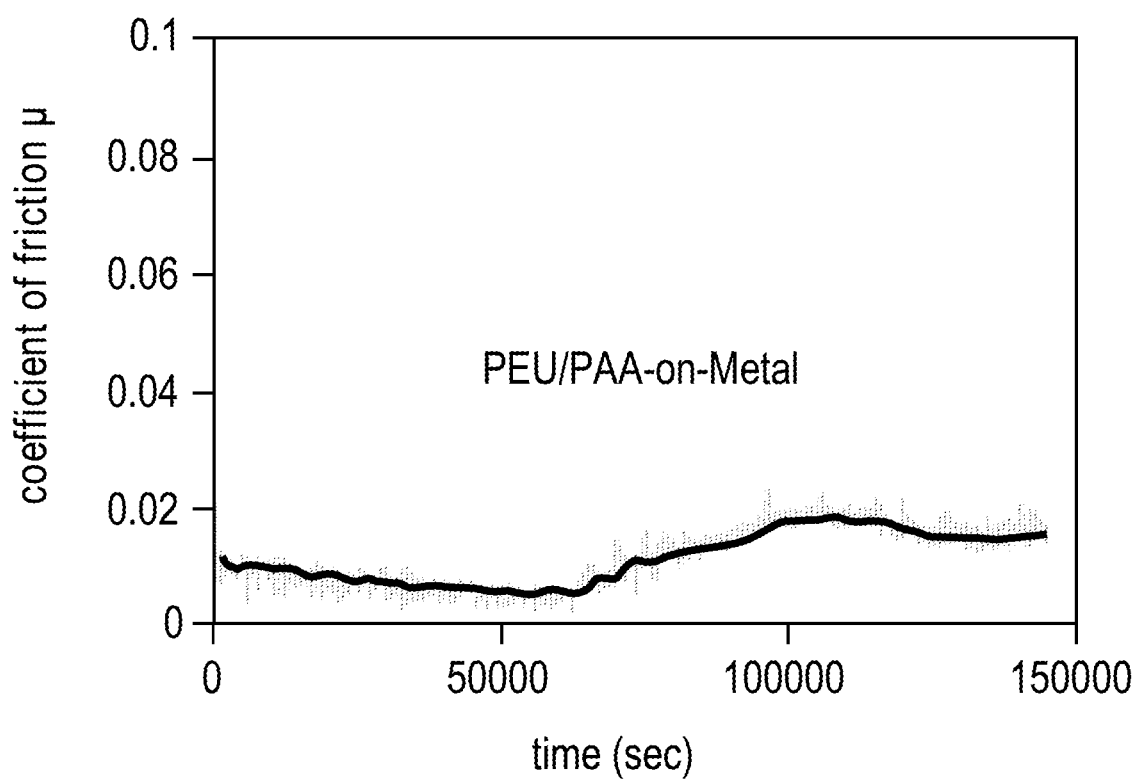
FIG. 43 shows the coefficient of friction of the PEU/PAA semi-IPN material on metal under static load associated with Example 38.

The coefficient of friction μ of a PEU/PAA semi-IPN of this invention against itself was measured real-time during a wear test using a built-in torque cell, and was found to range between 0.015 to 0.06, and as shown in FIG. 42, is similar to cartilage-on-cartilage μ values. Because of its lower (compared to cartilage) permeability, the PEU/PAA semi-IPN of this invention can preserve a lower coefficient of friction for longer and at higher contact pressures. FIG. 42 shows the effective coefficient of friction during a wear test of the joint interface material (labeled "PEU/PAA-on-PEU/PAA" in the graph) under 2.4 MPa of continuous (static) contact pressure. Literature reports on natural cartilage values and experimental data/literature reports on UHMWPE on CoCr are also presented in the plot (Mow, 2005; Wright 1982). As expected, the coefficient of friction was found to remain unchanged over the course of time when the load was applied in cycles of 1 Hz; similar results are reported for cartilage. The low coefficient of friction in the material can be explained in terms of (a) hydroplaning action, (b) load sharing between the solid and the fluid phases of the material, and (c) thin film lubrication as water persists on the surface of the material. The small increase of μ under static load can be explained by a small partial dehydration of the material under the pressure. In comparison, natural cartilage will lose most of its water under static load and therefore its coefficient of friction increases rapidly and to higher levels. Removal of the load and subsequent rehydration restores the initial coefficient of friction for natural cartilage.

Example 37

The coefficient of friction is a number that indicates the force resisting lateral motion of an object. It is expressed as a unitless ratio of the frictional force to the normal force. The dynamic coefficient of friction for the polyether urethane/polyacrylic acid (PEU/PAA) semi-IPN on was tested on metal, and the dynamic coefficient of friction is shown as a function of time. Briefly, a piece of Elasthane™ 55 D (polyetherurethane) was soaked in acrylic acid with an initiator and cross-linker, and cured to form a water swellable semi-IPN of the present invention. Plugs 8.8 mm in diameter and 1 mm thick were cut, swollen in PBS, and then rotated at a frequency of 1 Hz against a 3/16" stainless steel disc at a contact stress of 2.0 MPa while being submerged in PBS. Using a custom-made wear tester made according to ASTM F732 standards equipped with both a force load cell and a torque load cell, the dynamic coefficient of friction was measured real-time during the wear test experiment. The dynamic coefficient of friction of the material varied between 0.005 and 0.015 over a period of 36 hours.

Example 38

Figure 45A:
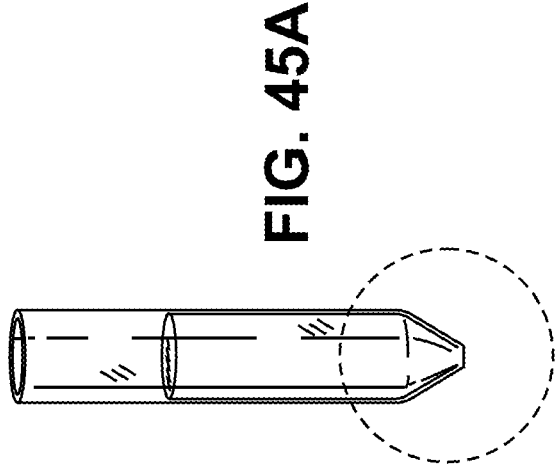
FIGS. 45A-C show the results of wear testing of the PEU/PAA semi-IPN material associated with Example 39.
Figure 45B:
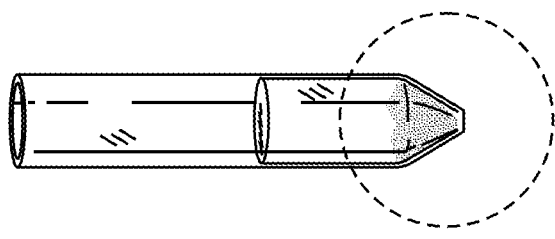
Figure 45C:
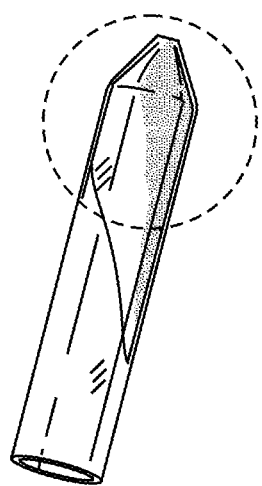
Figure 46:
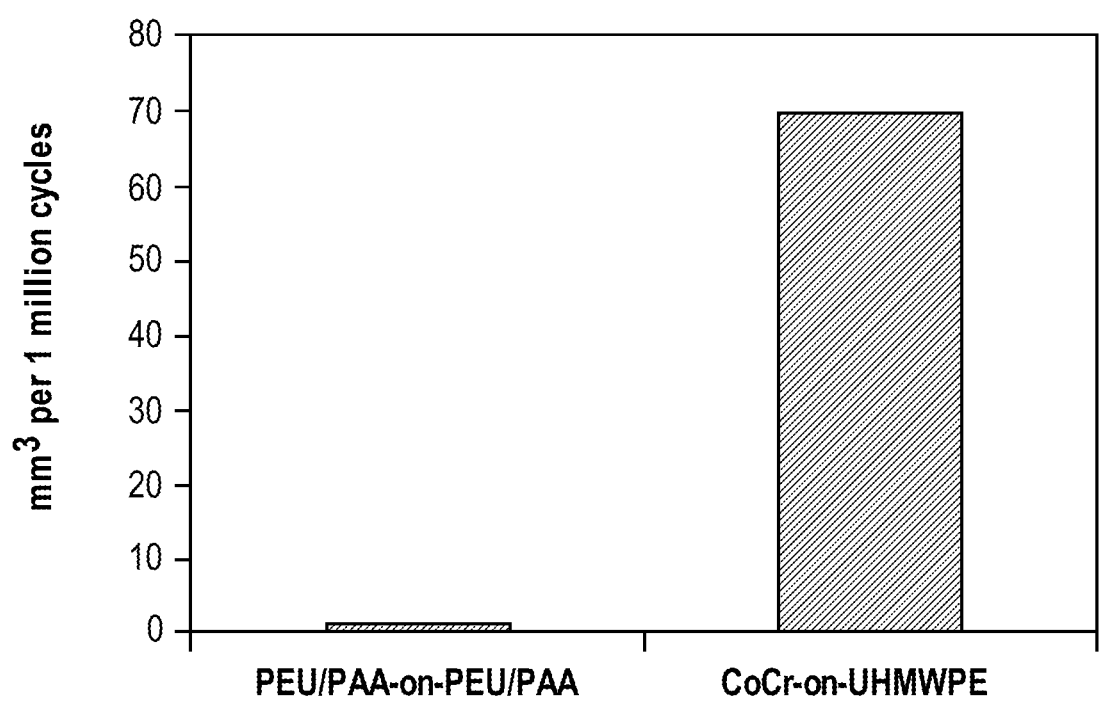
FIG. 46 shows quantification of the results of wear testing of the PEU/PAA semi-IPN material associated with Example 39.

Wear experiments of the PEU/PAA semi-IPN of this invention were conducted according to ASTM F732 using a pin-on-disc configuration. Results are shown in FIGS. 44, 45, and 46. Discs and pins formed from the joint interface material were tested to 2,500,000 cycles. As a basis for comparison to industry standard materials, a CoCr pin-on-UHMWPE (Cobalt chrome on ultra-high molecular weight polyethylene) disc configuration was also tested for 1,000,000 cycles.

In the test of the PEU/PAA semi IPN of this invention, the pins were 8.8 mm in diameter, 2.5 mm in thickness. The disc was 88 mm in diameter and 2.5 mm in thickness. The pins were rotated over the disc at a radius of 24 mm and at a rate of 1.33 Hz under a pneumatically applied cyclic load. A pressure regulator was used to adjust the air pressure so that the desired force was applied. The load was measured using a load cell (Sensotec Honeywell, CA) directly under the disc. The disc and the pins were mechanically isolated so that the torque caused by the friction generated between them can be measured by a torque cell (Transducer Techniques, CA) connected to a computer equipped with a data acquisition card (National Instruments, TX). The pin and discs were contained in a chamber filled with PBS. The temperature was controlled and kept constant at 37° C. using a thermocouple-resistor-fan system. Using the equation $\mu=T/r*F$, where T is the measured torque, r is the radius of rotation(=24 mm) and F being the total force applied on the pins, the coefficient of friction was constantly monitored. The coefficient of friction was found to be 0.016 and independent of the contact pressure (range tested 0.1-3.5 MPa) and slightly increased to 0.021 under heavy static contact load, but returned to the original value after fluid recovery. The wear was measured using the gravimetric method every million cycles: the disc and the pins were weighed separately after vacuum drying for 3 days. The wear test solution (PBS) was collected and visually examined; no signs of visible wear particles were noted at all steps of the tests. The wear test PBS solution was vacuum filtered using a 2.5 μm pore filter to capture any wear particles, flushed with deionized water to remove remaining PBS salts and then dried overnight under vacuum and desiccant. As a control, a similar test was performed using CoCr pins (Fort Wayne Metals, IN) on UHMWPE (Orthoplastics, UK). Three polished (Ra<1.6 μm) CoCr flat pins of OD=7 mm were tested in the same instrument against a polished UHMWPE disc of 2.5 mm thickness and OD=88 mm (rotation radius=24 mm), rotating at 1.2 Hz under 3.4 MPa static contact load and at 37° C. isolated environment.

Observation of the disc formed from the PEU/PAA semi-IPN of this invention after the test (FIG. 44A) revealed no macroscopically perceptible wear track along the pin-on-disc articulation surface. (FIG. 44B is a close-up view of the location of the wear track. Dashed lines have been added to indicate the path; the radial arrows start from the center of the disc.) In comparison, as shown in FIG. 44C, the UHM-WPE disc after 2.0 M cycles of wear against CoCr pins has a visible track 126 µm deep.

Weighing of the wear test solution filtrate using a scale with a 0.01 mg resolution (Mettler Toledo, Ohio) showed that the volumetric wear rate of the PEU/PAA semi-IPN was approximately 0.6 mg/$10^6$ cycles or 0.63 $mm^3$/$10^6$ cycles or 0.63 $mm^3$/150×$10^3$ m. This value, however is close to the resolution of the methods. A schematic of the wear test solution from the wear test of the inventive joint interface material comprised of PEU/PAA semi-IPN is shown in FIG. 45 A, demonstrating an absence of particles in the PBS solution. Compare FIG. 45 A to schematics of the wear test solution of the UHMWPE disc shown in FIGS. 45 B and 45 C, which show substantial wear debris particles generated during the CoCr-on-UHMWPE wear test.

Although attention was paid to eliminate external factors such as dust, moisture and static in order to increase the accuracy of the results, the wear values are well near the statistical and practical detection limits of the methods available. These results are consistent with the hypothesis that since the PEU/PAA semi IPN according to the present invention—like natural cartilage—is comprised of mostly water, and the surface is persistently lubricated with a film of water, there is little, if any, contact between solid matrices.

Wear particle measurements were also taken for the CoCr-on-UHMWPE experiments, which not only created a visible wear track (FIG. 44 B) on the UHMWPE disc, but generated substantial macroscopic wear debris (FIGS. 45 B and C). The UHMWPE disc was weighed and the difference in weight yielded an average wear rate of 64 mg/$10^6$ cycles or 69 $mm^3$/150×$10^3$ m (FIG. 46). This study points that the joint interface material of this invention (labeled "PEU/PAA-on-PEU/PAA") is at least more than 100 more resistant to wear than the traditional combination of CoCr-UHM-WPE, widely used in total joint replacements.

Example 39

FIG. 47 shows the swelling behavior of PEU/PAA and PEU in various aqueous and organic solvents. Briefly, a sheet of Elasthane™ 55 D (polyether urethane) was soaked in acrylic acid with initiator and cross-linker, and cured to form a semi IPN. A small piece of the IPN or Elasthane™ 55 D was obtained and weighed. The sample was soaked for 20 hours in a solution containing the solvent indicated in the Figure. (The samples were swollen, but did not dissolve). The sample was removed from the solvent, briefly dabbed dry, and then weighed again. The change in weight due to swelling is expressed as the % difference. While Elasthane™ 55 D on its own does not take up water, the IPN of the present invention readily swells with water to form a lubricious, hydrated IPN. In addition, other solvents can be used to swell the starting polymer to create the IPN of the current invention. In the case of polyurethanes, the ability of various solvents to swell the material depends on the properties of the solvent (such as its polarity, acidity, and molecular weight) as well as the relative solubility of the polymer components (e.g. hard and soft segments) in the solvent.

Example 40

Figures 48A, 48B:
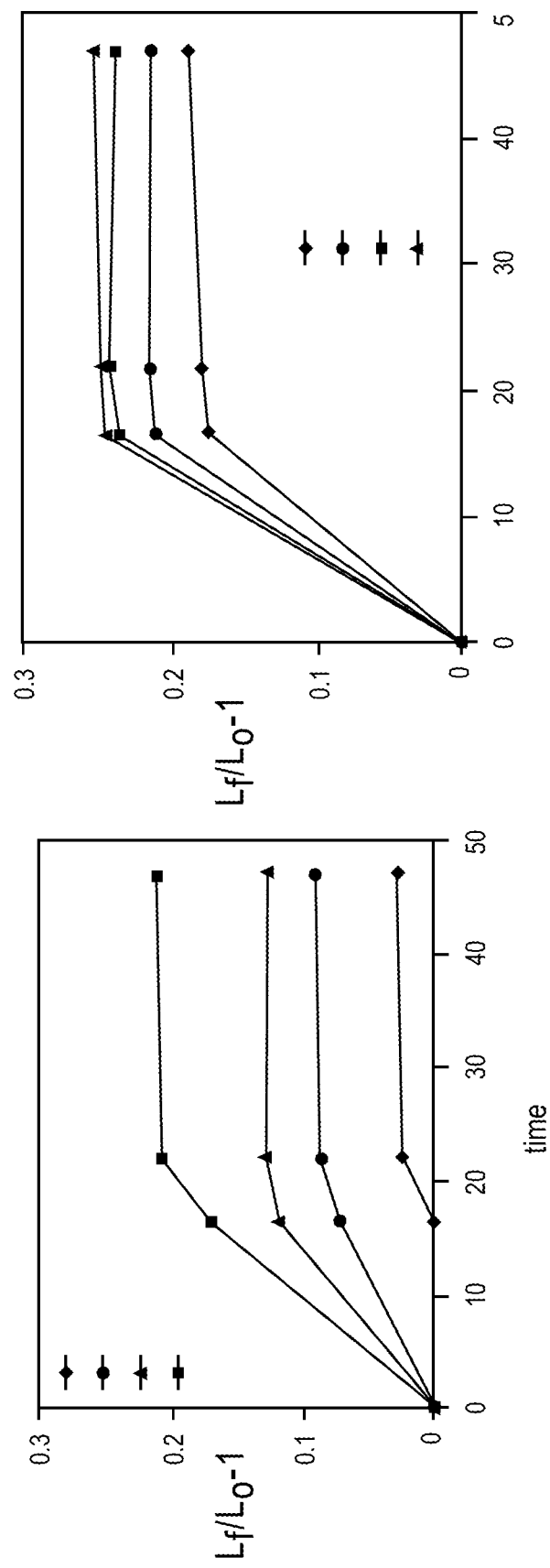
FIGS. 48A-B show the results of the swelling of polyether urethane and PEU/PAA semi-IPN in water and acetic acid associated with Example 41.

The swelling of polyetherurethane by acrylic acid in water and acetic acid was tested. Swelling solutions were prepared containing 10, 30, 50, and 70% acrylic acid monomer in deionized water (FIG. 48A) and in acetic acid (FIG. 48B) Small pieces of Elasthane™ ® 55 D (polyetherurethane) were obtained and measured. A sample of the Elasthane™ was placed in each solution. The samples were removed from the solvent, the surface briefly dabbed dry, and then measured again. The change due to swelling is expressed as the final length of the specimen after equilibrium swelling (Lr) divided by the original length ($L_o$) minus 1; in this way, the fractional increase in length relative to the initial state (y=0) is plotted versus time. Swelling of the Elasthane™ 55 D was observed using either water or acetic acid as a solvent. More swelling was observed when a higher amount of acrylic acid was used in the swelling solution. Of note, the concentration dependence of acrylic acid on the swelling of the Elasthane™ samples was different depending on whether water or acetic acid was used as the solvent.

Example 41

Figure 49:
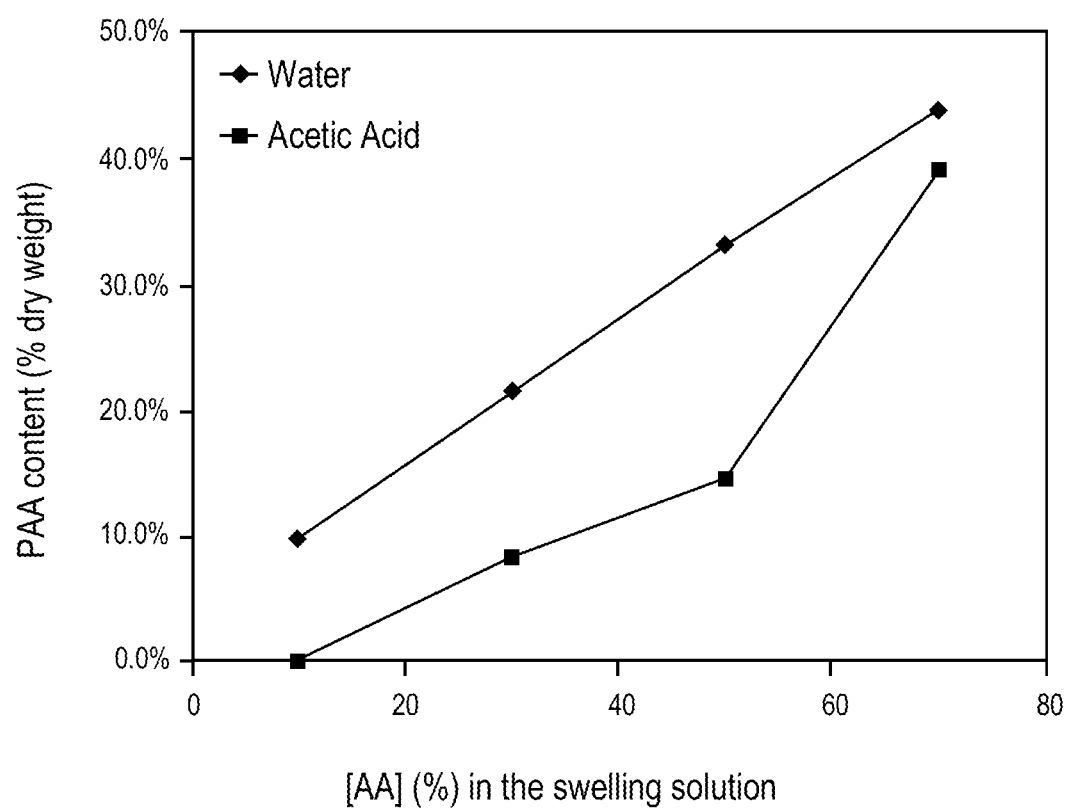
FIG. 49 shows polyacrylic acid content in the PEU/PAA semi-IPN as a function of the amount of acrylic acid in the swelling solution associated with Example 42.
Figure 50:
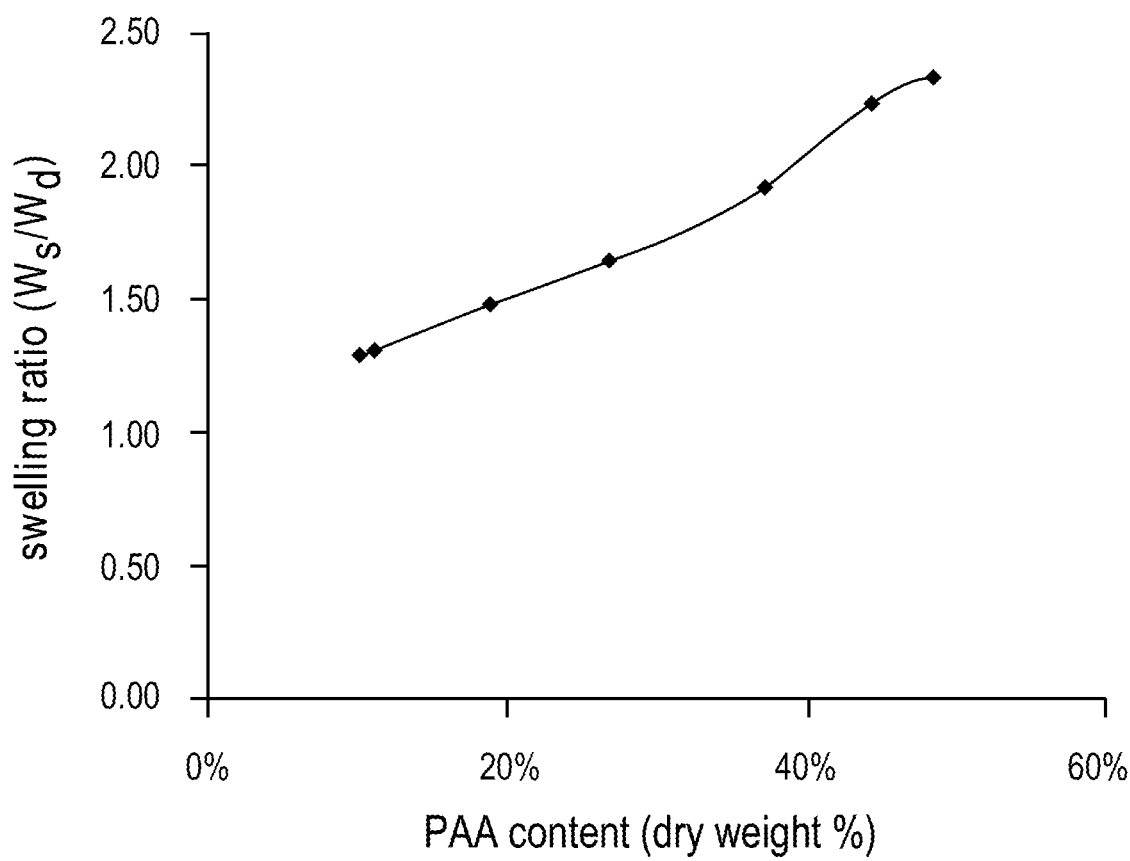
FIG. 50 shows the swelling of PEU/PAA semi-IPN as a function of the amount of polyacrylic acid in the semi-IPN associated with Example 43.

FIG. 49 shows the amount of poly(acrylic acid) present in the PEU/PAA semi-IPN after curing is plotted as a function of the starting concentration of acrylic acid monomer in different swelling solutions.

Swelling solutions were prepared containing 10, 30, 50, and 70% acrylic acid monomer in deionized water and in acetic acid. Small pieces of Elasthane™ 55 D (polyetherurethane) were obtained and weighed. Samples were placed in each of the water/acrylic acid or acetic acid/acrylic acid solutions along with cross-linker and initiator. The samples were cured, swollen in acrylic acid in either water or acetic acid, removed from the solution, dried, and then weighed again. Incorporation of acrylic acid into the Elasthane™ 55 D to form a semi-IPN was observed using either water or acetic acid as solvent. More incorporation of acrylic acid was observed when a higher concentration of acrylic acid was present in the swelling solution.

Example 42

Semi IPNs were prepared essentially as described in FIG. 49, and the polyacrylic acid content of the IPNs was determined. The dried materials were weighed, swollen in saline until equilibrium was reached, and weighed again. The change in weight of the semi IPN is expressed as a ratio of the weight of the swollen material/weight of the dry material (Ws/Wd) for each concentration of polyacrylic acid. An increased amount of polyacrylic acid in the polymer correlates with an increased uptake of saline into the water-swellable semi-IPN. Since the semi-IPNs in these experiments were neutralized to pH 7.4, in these experiments, the dry weight of the semi-IPN included the salts present in the saline swelling solution, since the monovalent cations (predominantly sodium, which has a MW of 23 g/mol) are counterions to the carboxylate groups in the material.

Example 43

FIGS. 51-54 show the results of creep and stress relaxation/compression testing. Tests were performed on PEU/PAA semi IPNs formed from Elasthane™ 55 D (polyetherurethane) soaked in acrylic acid with initiator and cross-linker, and cured.

Figure 51A:
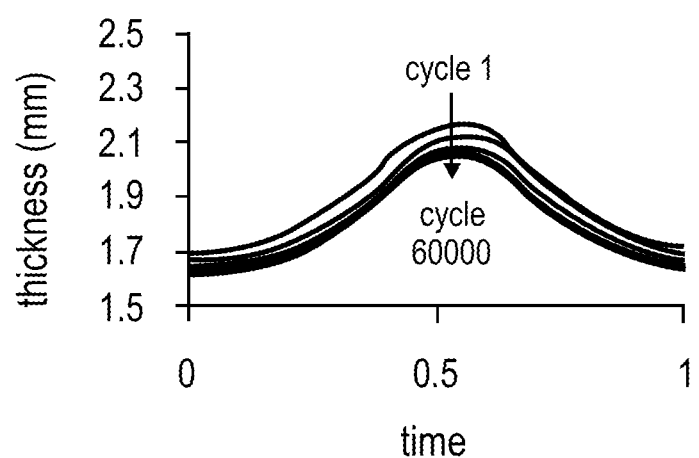
FIGS. 51A-B show the results of Dynamic Compression testing of the PEU/PAA semi-IPN material as associated with Example 44.
Figure 51B:
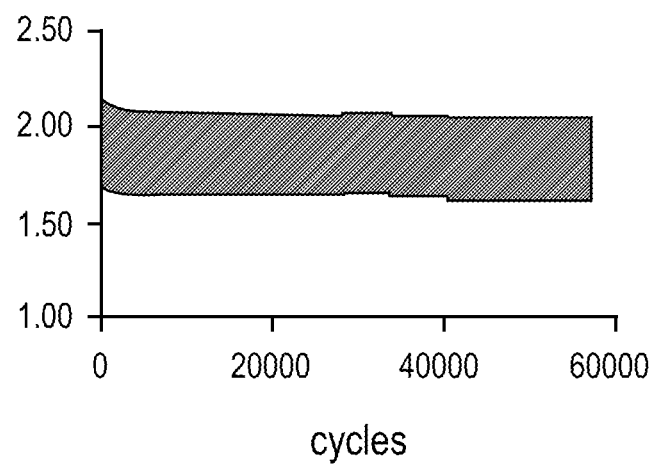

FIG. 51 shows the results of cyclic compression testing. The behavior of the PEU/PAA semi IPN was tested under dynamic compression conditions to determine permanent creep and creep recovery. Permanent creep is the time-dependent deformation of a material under a constant load.

Creep recovery measures the rate of decrease in the applied deformation after a load is removed. Experimental setup of the compression test followed the ASTM standard D695, Standard Test Method for Compressive Properties of Rigid Plastics, with the samples being subjected to a sinusoidal loading scheme designed to mimic the physiologic, cyclic compressive loads seen in a gait cycle.

A sample of the PEU/PAA semi IPN was removed and measured in the direction of its thickness, subject to cycles of compressive stress from 0-3 MPa at a frequency of 1 Hz for over 60,000 cycles, measured again in the direction of its thickness, re-equilibrated (relaxed) in PBS to allow for recovery from creep, and measured again in the direction of its thickness. FIG. 51 A shows the results of thickness measurements on representative samples subject to one-second long cycles of tests (at the 1st, 1000th, 10,000th, $20,000^{th}$ $40,000^{th}$ and $60,000^{th}$ cycles) superimposed in one figure. FIG. 51 B shows how the thickness of the material changes over all cycles of testing. The thickness of the material, as measured after load was removed during the cycle, dropped from an initial value of 2.160 mm at the first cycle to about 2.000 mm by the $60,000^{th}$ cycle. However, after re-equilibration (relaxation) in PBS and creep recovery at the last cycle, the material returned to a thickness of 2.135 mm, a total loss of thickness of only 1.1% due to permanent creep.

Figure 52:
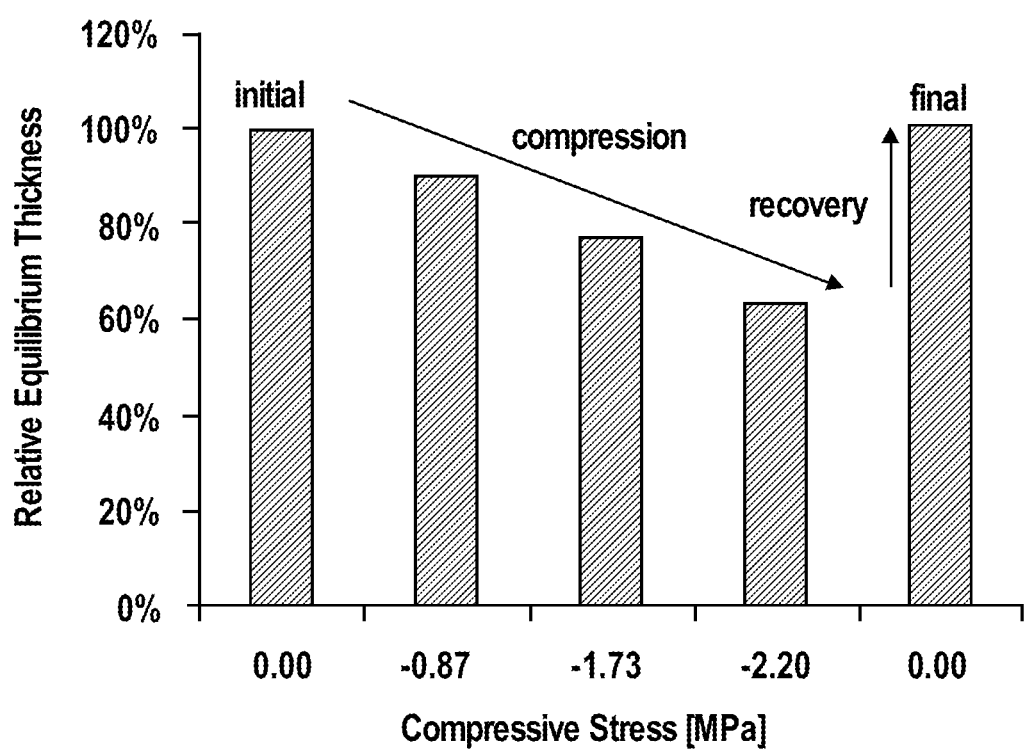
FIG. 52 shows the results of the application of a multistep stress relaxation compressive stress test to the PEU/PAA semi-IPN material followed by relaxation as associated with Example 44.

FIG. 52 presents the equilibrium compressive behavior of the PEU/PAA semi IPN as determined through a multiple-step stress relaxation test, in which a given displacement is applied and then the material is allowed to relax (equilibrate). Notably, under these test conditions, the material fully recovered to its equilibrium value after removal of the load, as shown by the last data point in the FIG. 52, indicating full creep recovery. The stress of 2.20 MPa (4th data point) is 15% higher than the maximum functional stress in a hip device (total load through the hip of 3 times body weight) that is predicted by finite element models.

A static creep test was also performed (data not shown). Creep is the time-dependent deformation of a material under a constant load. The behavior of the PEU/PAA semi IPN tested under static compression was tested following ASTM D2290-01 "Standard Test Methods for Tensile, Compressive, and Flexural Creep and Creep-Rupture of Plastics". A plug of the PEU/PAA semi IPN with an initial diameter of 9.525 mm and a thickness of 1.115 mm was put under an initial stress 4 MPa in a fluid PBS bath. After applying the stress for approximately 20,000 seconds (to a total strain of 14.29%), the load was released and the material allowed to relax (re-equilibrate) in PBS. The final thickness of the plug was 1.109 mm. The final unrecovered creep after more than 40,000 cycles was 2.7%.

Figure 53:
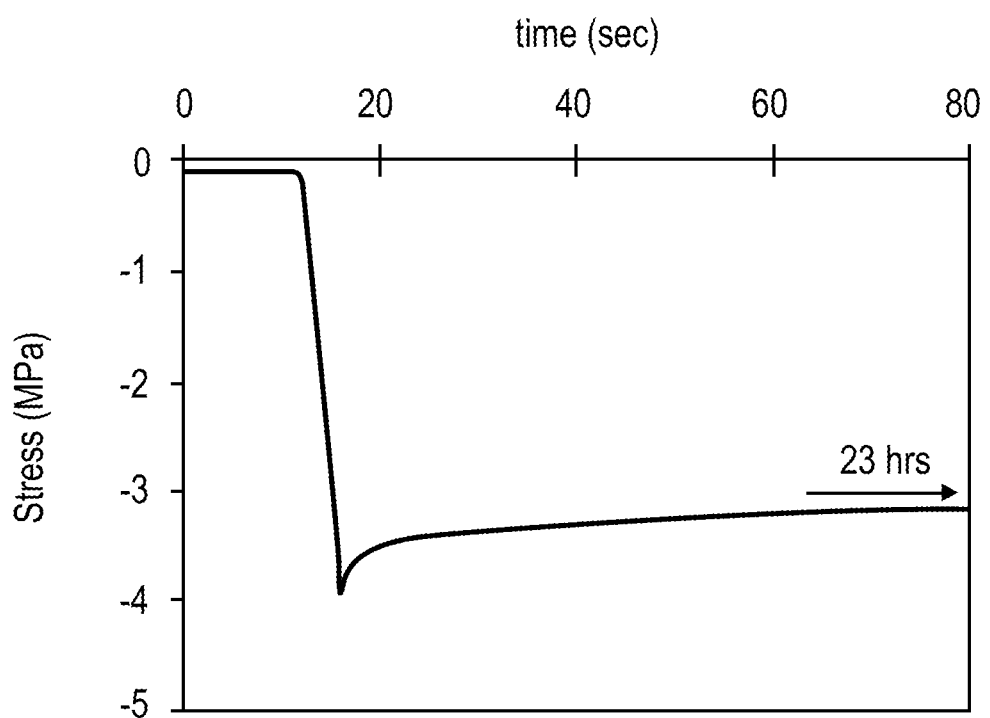
FIG. 53 shows the results of the application of compressive stress to the PEU/PAA semi-IPN material associated with Example 44.

FIG. 53 shows the results of a compression set test according to ASTM D395. In this test, a plug of PEU/PAA with an initial diameter of 9.525 mm and a thickness of 2.13 mm was subjected to a constant compressive strain of 15% for 23 hours at room temperature in a fluid bath filled with PBS. After allowing the material to relax and re-equilibrate in PBS, the final thickness of the plug was 2.08 mm. This yields a compression set value of 9.5%. As a basis of comparison, PEU (Elasthane™ 55 D) alone exhibits a compression set value of about 45% under the same conditions (22 hrs, room temperature). Therefore, the presence of the polyelectrolyte in the PEU/PAA semi-IPN provides a way for the PEU material to resist permanent creep through rehydration of the matrix with water due to the hydrophilicity and high swellability of the negatively charged polyelectrolyte.

Example 44

FIG. 54 shows a list of some of the materials made in accordance with the present invention. The first column shows the hydrophobic polymer used. If a modification was made to the hydrophobic polymer as indicated in the second column, the material for the modification was cast with the material, or, if the modification was crosslinking functionality, the modification was added and the material prepared and crosslinked and used thereafter with the crosslinks reacted. The monomer, comonomer (if any), crosslinker and initiator were added in the indicated solvent as indicated in the figure in order to swell the prepared hydrophobic polymer. Each hydrophobic polymer sample was allowed to swell for up to 2 days, removed from the solution, and cured using the indicated method following standard procedures. The material was washed and swollen in PBS. The abbreviations used are as follows: MBAA=methylene bisacrylamide, HMPP=2-hydroxy-2-methyl propiophenone, TEGDMA=triethylene glycol dimethacrylate, and $H_2O$=water.

Another aspect of the invention provides an orthopedic implant with a bone interfacing member that may be conducive to bone in-growth and a water swellable IPN or semi-IPN. The addition of a water-swellable IPN or semi-IPN to a bone interfacing member (e.g. a rigid or mostly rigid, ceramic, metal, or polymeric member placed in contact with the bone) may provide certain advantages, such as by taking advantage of current knowledge and surgical expertise related to accepted orthopedic implants while overcoming some of the disadvantages of such implants.

Another aspect of the invention provides a synthetic "joint capsule" that may surround or partially surround or connect with other components of the device. The joint capsule may function as a self-contained fluid reservoir for the implant. In particular, in a hip implant (e.g. a femoral or acetabular component), a synthetic "joint capsule" may surround the femoral, acetabular, and/or labral components and provide lubricant in-between the femoral and acetabular components.

Another aspect of the invention provides other components for providing support, lubrication, and/or spacing to a joint of a body. For example, the addition of a "labral" or ring-like component that contours the acetabular rim or the shoulder joint, or a meniscal component that contours an outer aspect of a tibial plateau could act as a buffer between acetabular/femoral components, humeral head/glenoid, or femoral/tibial components of an implant similar to way the natural labrum and meniscus function.

Figure 55A:
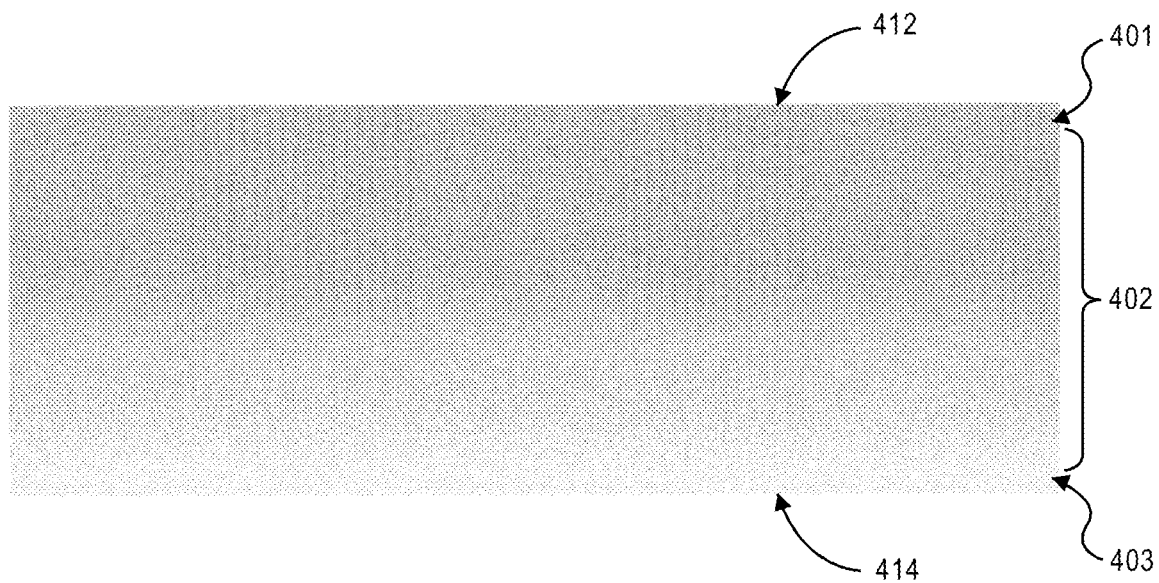
FIGS. 55A-B show a gradient polymer alloy (FIG. 55A) and a porous metal device (FIG. 55B) before being joined.
Figure 55B:
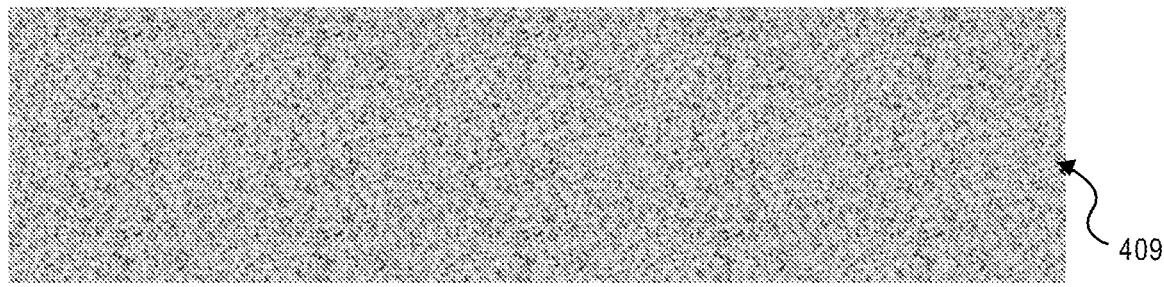
Figure 56:
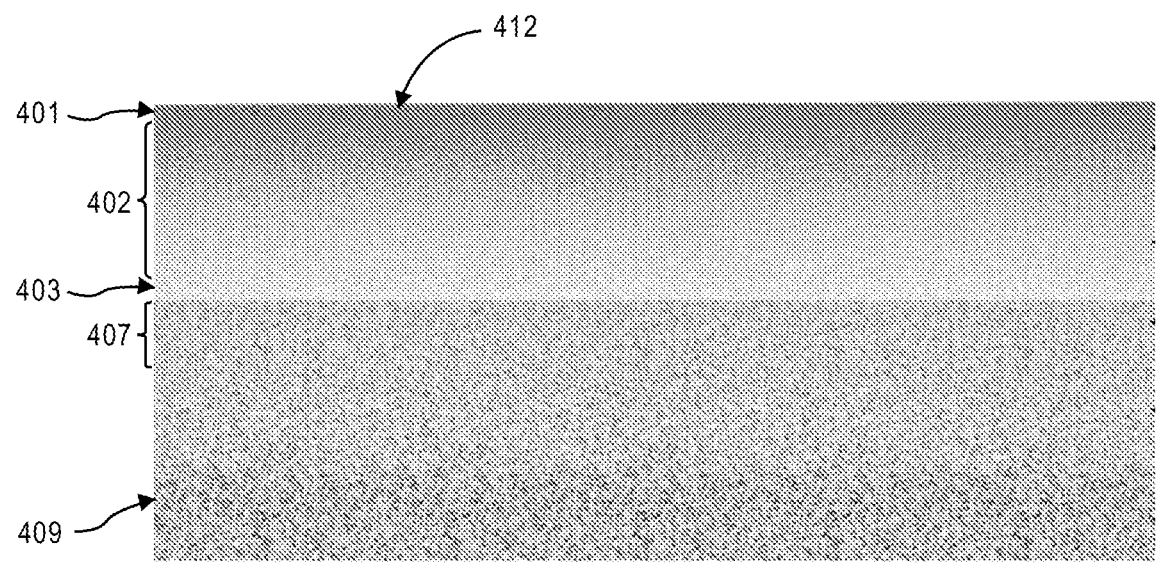
FIG. 56 shows a gradient polymer alloy device with gradient polymer and a porous metal device after joining according to one aspect of the invention.

One aspect of the invention is an orthopaedic implant comprising a hydration, stiffness, and/or compositional gradient polymer alloy (an IPN or semi-IPN) that is fused (e.g. along an attachment zone) to a bone interfacing member. FIGS. 55A-B and FIG. 56 show a gradient polymer alloy and a porous metal before (FIGS. 55A-B) and after (FIG. 56) they are joined. FIGS. 55A-B shows the gradient polymer and porous metal in an exploded view with three phases of gradient polymer alloy, including hydrated phase 401 (with a bearing surface 412), transitional phase 402, non-hydrated phase 403 (with attachment zone 414), and porous metal bone interfacing member 409. Any gradient polymer may be used, including any polymer described herein or in U.S. patent application Ser. No. 13/219,348 filed Aug. 26, 2011, now U.S. Pat. No. 8,883,915.

In one embodiment, a semi-IPN or IPN may include a compositional gradient polymer alloy (an IPN or semi-IPN) with a second gradient made of PMMA (polymethyl methacrylate). The PMMA may form a second gradient from a portion of a gradient IPN or semi-IPN to an attachment zone. In a particular example, the gradient polymer alloy may include polyurethane and poly(acrylic acid) and the second gradient may be PMMA. In this embodiment, methyl methacrylate (MMA) monomers may be diffused into a polyurethane side or zone of a gradient IPN or semi IPN comprising polyurethane and poly(acrylic acid), then polymerized to form an IPN or semi-IPN of PMMA and polyurethane within the attachment zone. This yields an attachment zone with affinity and adhesiveness for PMMA bone cement according to U.S. patent application Ser. No. 13/219,348 filed Aug. 26, 2011, now U.S. Pat. No. 8,883,915. This gradient IPN with a PMMA-containing attachment zone can therefore be adhered to a bone interface member comprising a metal, a polymer (such as PMMA bone cement), or ceramic.

FIG. 56 shows the gradient polymer metal alloy of FIG. 55 joined with a bone interface member (metal device including hydrated phase 401 (with a bearing surface 412), transitional phase 402, non-hydrated phase 403, interfacial zone 407 comprising non-hydrated polymer from the attachment zone 414 interdigitated with porous metal, and porous metal from bone interfacing member 409. The gradient polymer alloy is mechanically interdigitated with porous metal to create a strong, smooth interface region.

A bone interfacing member may be any material, but preferably is one useful in orthopaedics and biocompatible, such as a metal, ceramic, or polymer. A bone interfacing member may be any metal, such as aluminum, cobalt, molybdenum, nickel, stainless steel, titanium, or combinations or alloys thereof and/or any other metals used in biomedical implants. A bone interfacing member may be any polymer that is sufficiently strong and biocompatible, such as PEEK, polyurethane, or UHMWPE. For simplicity, a bone interfacing member will be referred to as a metal, but it should be understood any material that connects a polymer gradient alloy to a bone can be used. A metal may be substantially solid, porous, etched, coated, or otherwise treated to aid in attaching the metal to bone and/or attaching a gradient polymer alloy to the metal, or may have a combination of these characteristics or treatments. A porous metal includes but is not limited to porous "trabecular" metal, porous metal foam, sintered metal beads (e.g. that form a porous structure), plasma sprayed porous metal, and/or chemically etched porous metal. A portion of the metal may be solid, porous, rough, etched, coated with osteoconductive material (e.g. calcium phosphate or hydroxyapatite), or otherwise treated and another portion not solid, porous, etched, coated, or otherwise not treated. In one example, a metal is porous on the bone contacting surface. In another example, a metal is porous on a polymer alloy facing side. In another example, a metal is porous on both a bone contacting surface and a polymer alloy facing side. A hydration gradient polymer alloy may be a combination of a hydrophilic polymer and a hydrophobic polymer, such that one side of the alloy is hydrophilic and hydrated, and the other side non-hydrated and hydrophobic. The latter side may be mechanically interdigitated or chemically bound with a metal bone interfacing construct. If a porous metal is used, the porosity may be any that allows or aids in attaching to a gradient polymer alloy or in attaching to bone. The porosity of the metal may be similar to the porosity of cancellous bone.

The gradient polymer alloy can be attached, connected or bound to the metal in any way.

In one example, the gradient polymer alloy was placed in contact with a porous metal specimen that was heated past the melting point of the polymer backing material. The two materials were compressed together under a load of, for example, 1 metric ton, and then allowed to cool. The result was a gradient polymer alloy fused to a porous metal. Examples of porous metals used were aluminum and titanium.

Figure 57A:
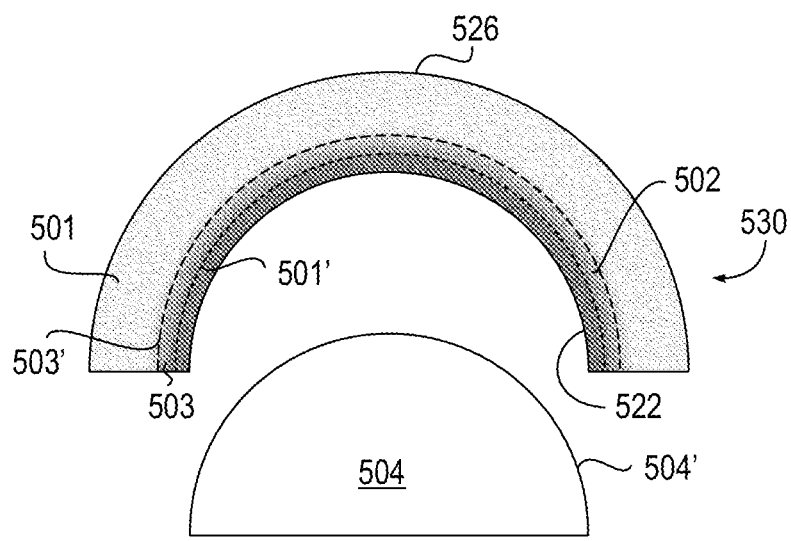
FIGS. 57A-57C and FIGS. 58A-58D show the steps of attaching a cap-shaped (FIGS. 57A-57C) and a cup-shaped (FIGS. 58A-58D) metal implant having a gradient polymer alloy bearing surface to a bone.
Figure 57B:
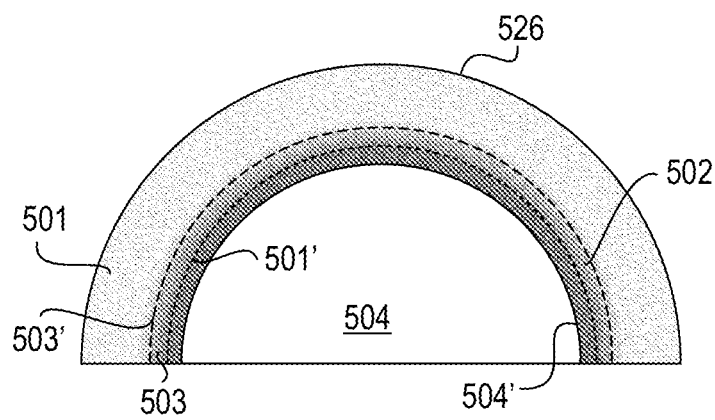
Figure 57C:
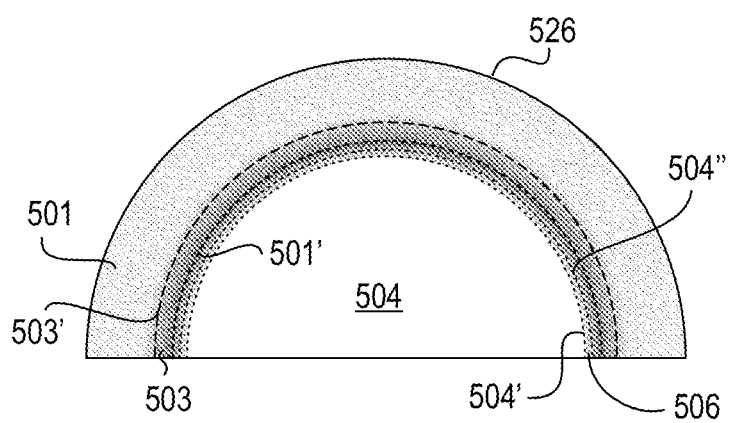
Figure 58A:
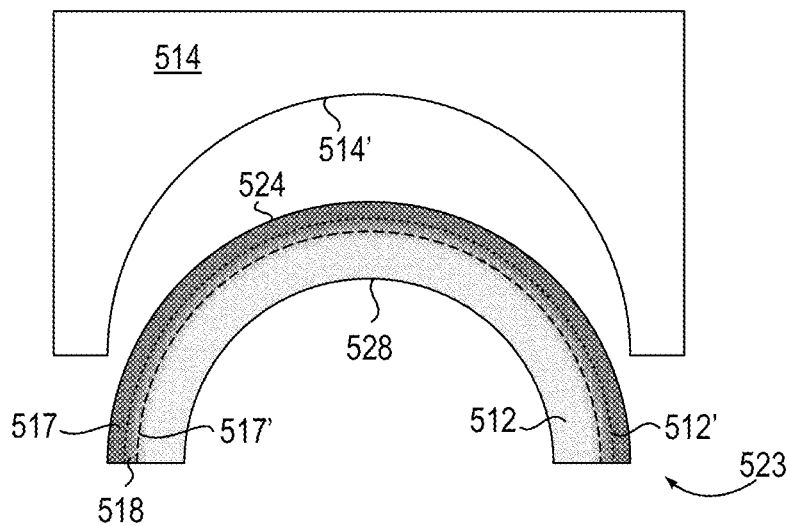
Figure 58B:
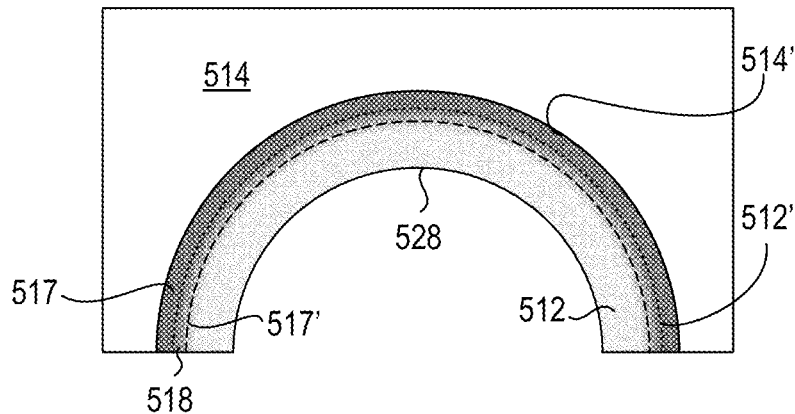
Figure 58C:
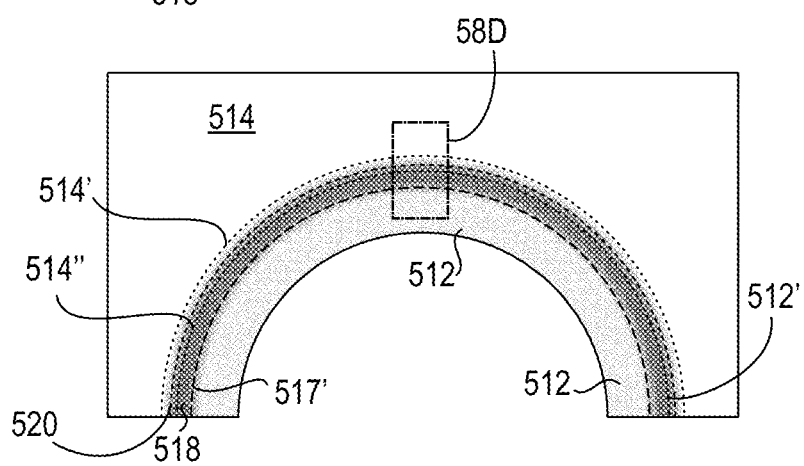
Figure 58D:
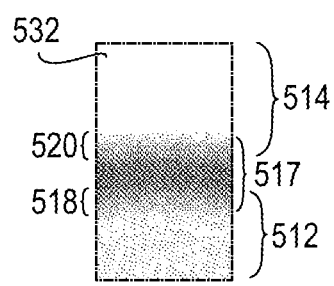

The use of porous metal or polymer in combination with a gradient polymer alloy allows for bone in-growth into the metal or polymeric bone-facing side of a device to create a strong but lubricious joint replacement having gradual transition from hydrated surface to strong bone. Polymer/metal and metal/bone regions of overlap are shown in FIGS. 57 and 58. FIG. 57 shows a porous metal or polymer countersurface (bone interface member), though the surface may also be non-porous. FIGS. 57 A-C and FIGS. 58A-D show orthopedic implants in the shape of a cap 530 (FIG. 57A) and a cup 523 (FIG. 58A) being attached to and in-grown with bone. The implants have hydrated polymer portions 501, 512 to provide bearing surfaces 526, 528 to interface with a joint surface. The hydrated polymer portion of the gradient polymer alloy and porous metal have been interdigitated 503 (518) in the region between 503' and 501' (512' and 517') to create a polymer/metal overlap region 502, 518. The implants also have porous metal portions 501, 517 with bone attachment zones 522 (524) to attach the interdigitated polymer metal implant 530, 523 to bone. When implant 530, 523 is placed next to bone 504, 514, the implant forms a new artificial joint surface on the bone. Post-operatively, bone grows into the porous metal side to create metal-bone integrated region 506, 520 between original bone surface interface 504' and new interface 504" (at the limit of the bone in-growth) that can strongly anchor the implant to a bone. The interdigitated metal-bone region distributes stresses better than does a sharp interface between the two materials, providing a strong anchor. An expanded view of the interfacial zone 508 is shown in FIG. 57D with bone 514 connected with metal implant 517 which is in aim connected with cartilage replacement polymer 512. FIG. 58D shows a closer view of the region shown in FIG. 58C overlap or interdigitation 520 between bone and metal, overlap or interdigitation 518 between polymer 512 metal 518, and transition from strong metal to lubricious surface 532. to create a strong, smooth joint replacement.

Figure 59A:
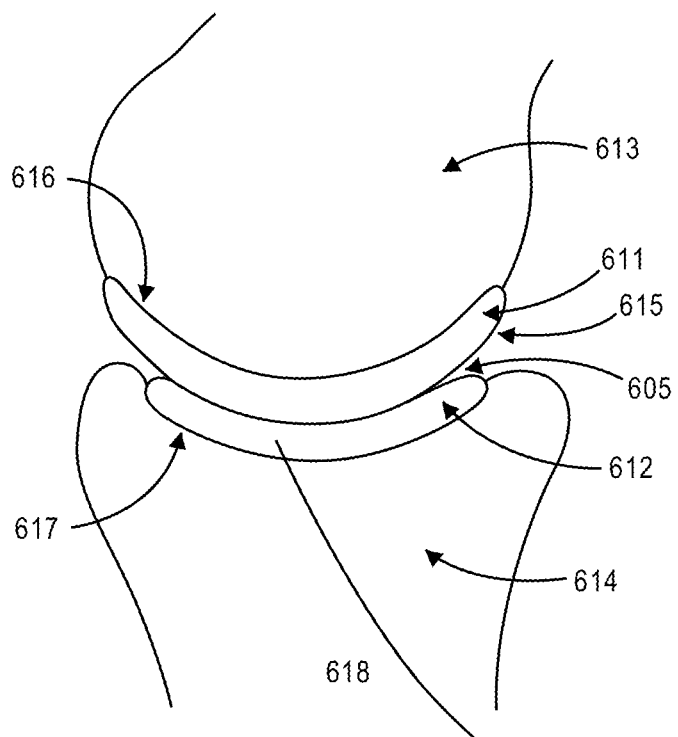
FIG. 59A shows both sides of a joint replaced with a metal implant having a gradient polymer alloy bearing surface.
Figure 59B:
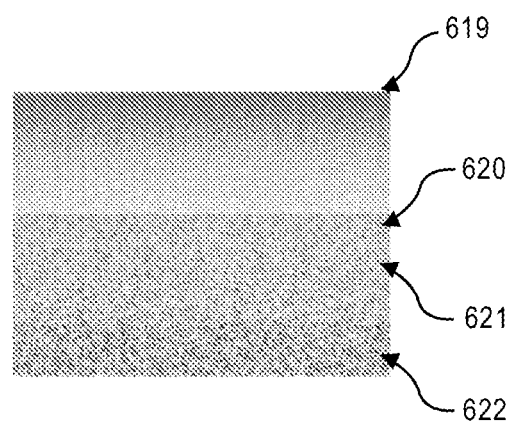
FIG. 59B shows a cross-section of the implant from FIG. 59A.

FIG. 59A shows two sides of a generic articular joint with both sides of the joint replaced with orthopedic implants according to the current disclosure. Concave bony prominence 614 has bone surface 617 accepting concave articular component 612. Convex bony prominence 613 has bone surface 616 accepting convex articular component 611. Concave articular component 612 mates with convex articular component 611 at articular interface 615. Cross section 618 of concave articular component 612 is shown in FIG. 59B immediately after being placed in the joint, i.e., before any bone ingrowth has occurred. Next to the bone is a layer of porous metal 622 serving as a bone interface member, then a polymer-metal interface region 621, non-hydrated side 620 of the polymer and, facing the articular surface, hydrated side 619 of the polymer.

In one example, a gradient polymer alloy can be physically snap-fitted into a metal mating component with a non-porous smooth contact surface and a counter-surface (bone contact surface) configured for attaching to bone that is porous, rough, and/or coated with osteoconductive material such as calcium phosphate or hydroxyapatite. In this case, a gradient polymer alloy component may be used similarly to the way that existing ultrahigh molecular weight polyethylene (UHMWPE) acetabular cups are fitted into metal backing components.

In another example, a gradient polymer alloy can be physically snap-fitted into a mating, polymeric component with a non-porous smooth contact surface (attachment surface) and a counter-surface (bone contact surface) meant for anchoring to bone. A counter-surface may be porous or non-porous. A counter surface may be coated with an osteoconductive material such as calcium phosphate or hydroxyapatite. Anchoring a gradient polymer alloy to bone can be achieved through any suitable means including one or more of: 1) bone ingrowth into a porous counter-surface (bone contacting surface), 2) briefly melting an entire surface or portions of a surface of a solid counter-surface and causing the material to flow into the bone pores, and solidifying the material to form a grout-like anchoring, 3) using or applying adhesive, cement (e.g. polymethylmethacrylate (PMMA)), epoxy, glue, or grout, to bind (e.g. chemically) or mechanically hold a counter-surface to bone.

In another example, a gradient polymer alloy may be chemically bonded to a metal portion or implant. Either (or both) sides of a metal maybe smooth, porous, or rough. Any number or type of chemical bonds may be made. In one embodiment a urethane linkage is formed between a polyurethane-based gradient polymer alloy and a tribochemically modified metal surface through reaction of terminal isocyanates in the polymer precursor and reactive —OH groups on the metal surface. A metal surface can be tribochemically modified with oxides, which can subsequently be further modified to hydroxyl groups, which can in turn be chemically reacted with free isocyanate groups to form an isocyanate chemical bond (see Myung et al., U.S. Patent Application Publication 2008/0241214). The gradient polymer alloy can also be joined to the bone interfacing member using or applying adhesive, cement (e.g. polymethylmethacrylate (PMMA)), epoxy, glue, or grout.

A gradient polymer bound to a metal surface may have any thickness. A gradient polymer may form a thin coating or layer over a metal surface. A coating or layer may be less than 30, less than 25, less than 20, less than 15, or less than 10 mm in a thickest region. In one particular example, a coating on a metal is less than 5 mm in a thickest region.

A gradient polymer alloy may be polyurethane based, and the polyurethane side of the alloy may be physically fused with a porous metal by melting a portion of the polyurethane and flowing it into pores of the metal, and then cooling the metal and polyurethane. Because a polyurethane side of a gradient polymer can be tough and hydrophobic, it is able to robustly anchor to the porous metal with an interface that is highly resistant to extreme and repetitive mechanical stresses.

An implant or device may be made after separate fabrication of a gradient material and a porous metal, and then the material and metal are fused. They may be fused by heating the metal, apposing the material and the metal, compressing the material and metal together, and then cooling the metal. In this way, the hydrophobic side of a gradient polymer is "melted" into the pores of a porous metal. Alternatively, a precursor of a gradient polymer can be injected molded directly onto a (pre-fabricated) porous metal, followed by post-processing of the polymer to yield a gradient polymer that is fused to the metal.

In another aspect of the disclosure, a synthetic joint capsule may be implanted. A synthetic joint capsule may surround one or both (or may be near, but not surround) implant components. A capsule component(s) may be closed or sealed to contain a fluid such that fluid cannot move in and out of a volume or space created, at least in part, by the capsule.

Figure 60:
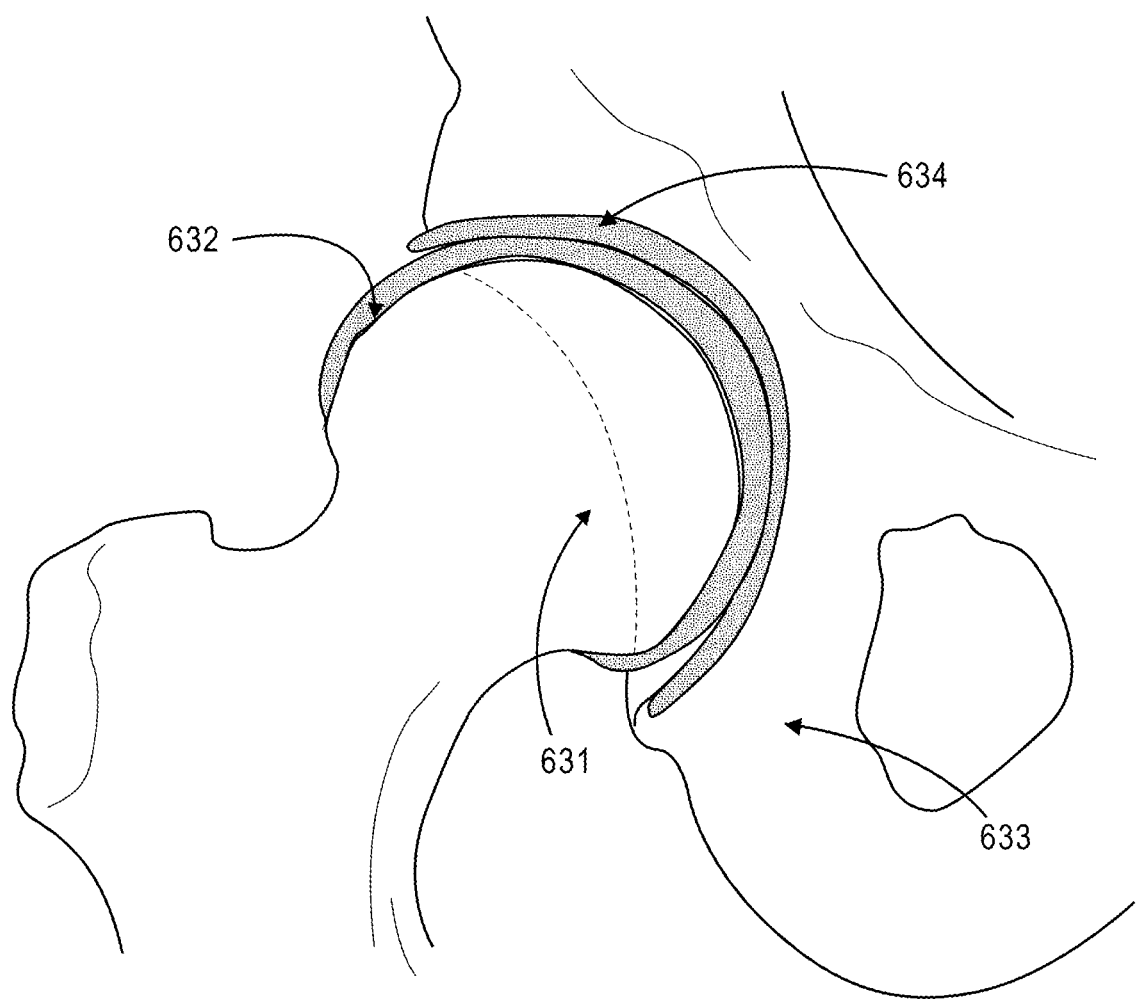
FIG. 60 shows a cap-on-cup total cartilage replacement in a hip joint.
Figure 61:
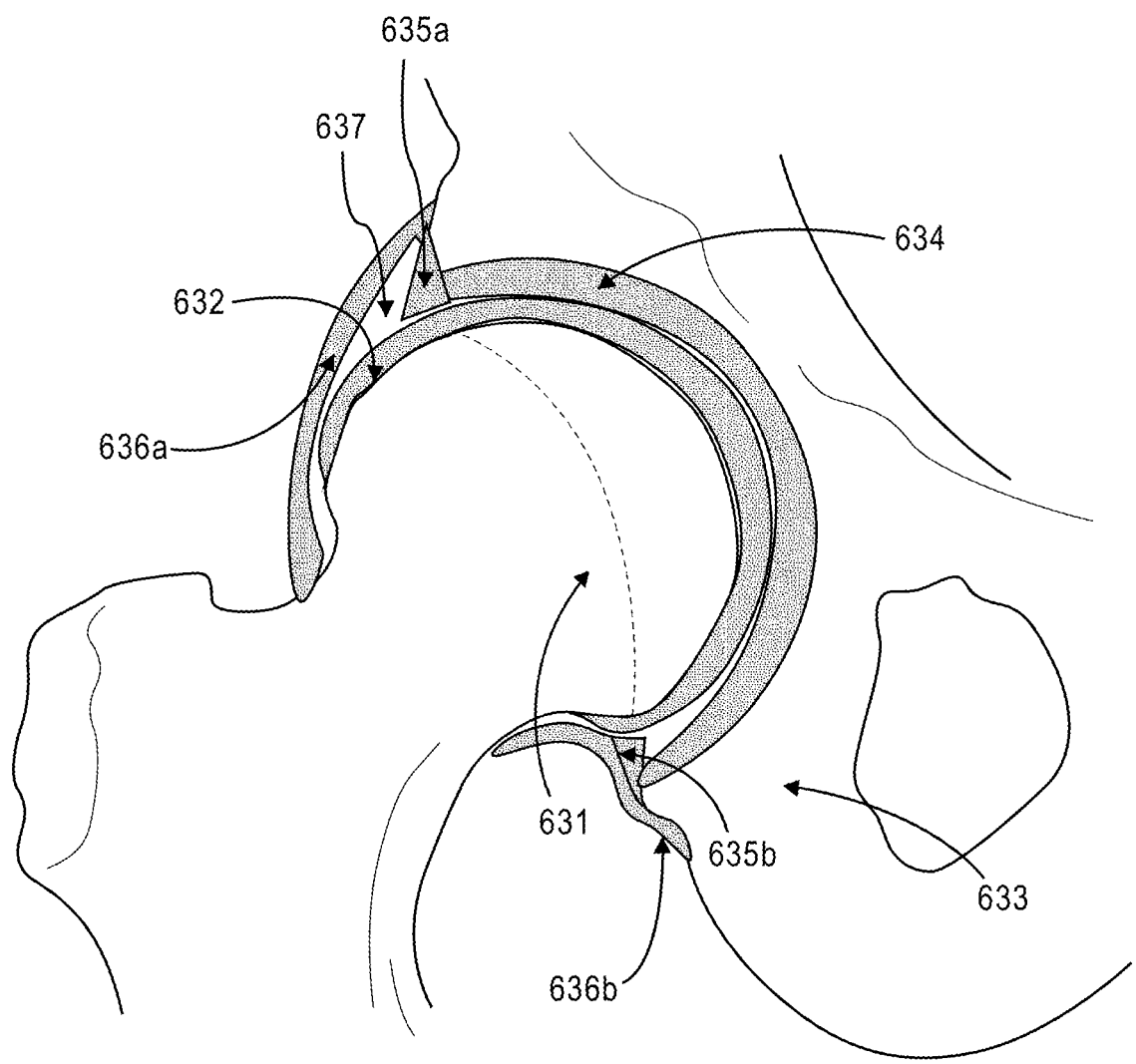
FIG. 61 shows a hip replacement system with cap-on-cup cartilage replacement implants such as the ones shown in FIG. 60, a synthetic joint capsule component, labral components and lubricant fluid according to one aspect of the invention.

FIGS. 60-61 illustrate placement of cap-on-cup, synthetic joint capsule and labral implants of a gradient polymer in a hip joint according to one aspect of the disclosure. FIG. 60 is a simplified version showing total cartilage replacement with convex articular component cap 632 over femoral head 631 and concave articular component cup 634 facing acetabulum 633 without a synthetic joint capsule or synthetic labral components in place. The components (e.g. cap and cup) are made from a gradient polymer alloy without a metal component.

FIG. 61 shows a total cartilage replacement device based on gradient polymer alloy components with the components shown in FIG. 60 and encapsulation of the hip joint with a capsule component 635, shown in superior cross-section 636a and inferior cross-section 636b, a labral component shown in superior cross-section 635a and inferior cross-section 635b, and containing lubricant fluid 637. In this embodiment, the capsule 635 encloses the entire joint, including the cap 632 and cup 634 described above. Capsule 635 may contact bone, joint implants or both to form its joint enclosure.

A joint capsule may be part of a gradient polymer and porous metal combination implant, or may be present in an implant having a gradient polymer without a porous metal component. A synthetic labral component may also be used in combination with the femoral and acetabular components, with or without a synthetic joint capsule component. The same holds true for the humeral head and glenoid in a shoulder joint.

The capsule's geometry and shape may similar to all or part of a natural joint capsule, which normally provides stability to the joint. In one example, a synthetic joint capsule contains a phosphate buffered saline or normal saline solution, which may serve as a lubricant fluid for a gradient polymer bearing surface(s). A synthetic capsule may be manufactured as an attached part of one or more bearing components, or may be a separate part. It may be assembled either pre-operatively or intra-operatively with another joint component(s). In another example, the capsule may be filled with a lubricant, such as a lubricating polymer (e.g. carboxymethyl cellulose, hyaluronic acid, or sodium polyacrylate).

The addition of a synthetic capsule may provide advantages, such as protection against dislocation, containment of wear debris, protection of the articular interface against host cells, or bone or cement particles, and/or creation of a one-piece device that may be implanted in a single step, much like an interpositional spacer device.

Figure 62:
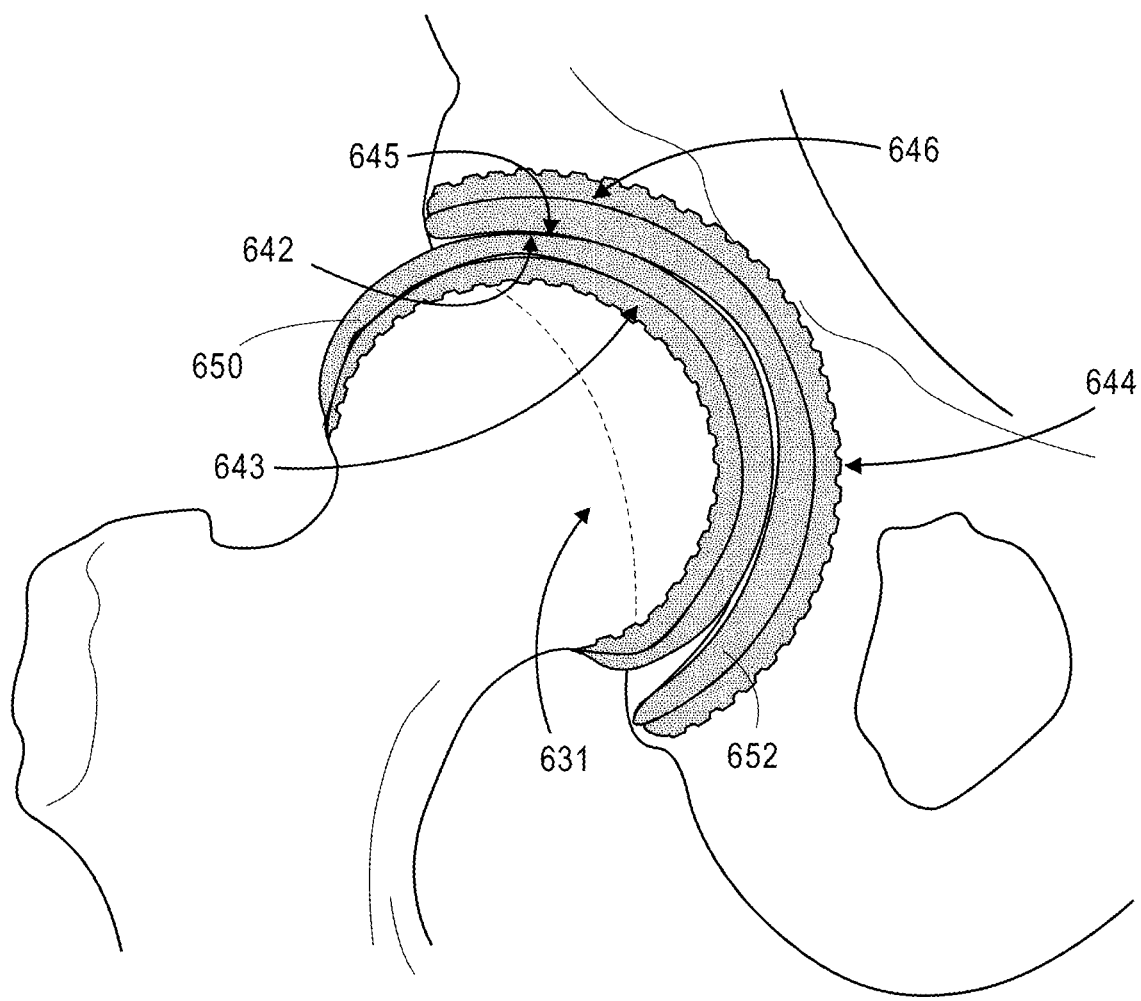
FIG. 62 shows a cartilage replacement system with cap-on-cup metal implants having gradient polymer alloy bearing surfaces.

A total cartilage replacement metal device with a polymer cap-on-cup surface may be placed in a joint. FIG. 62 shows a cartilage replacement device placed in a hip joint. Femoral component 650 is in place over femoral head 631. It includes has porous metal backing 643. Acetabular component 645 abuts acetabulum 644. Component surfaces 642, 645 mate to provide a joint interface. One or both component surfaces 645, 642 may be a polymer. FIG. 62 also shows porous metal backings 646, 643.

Figure 63:
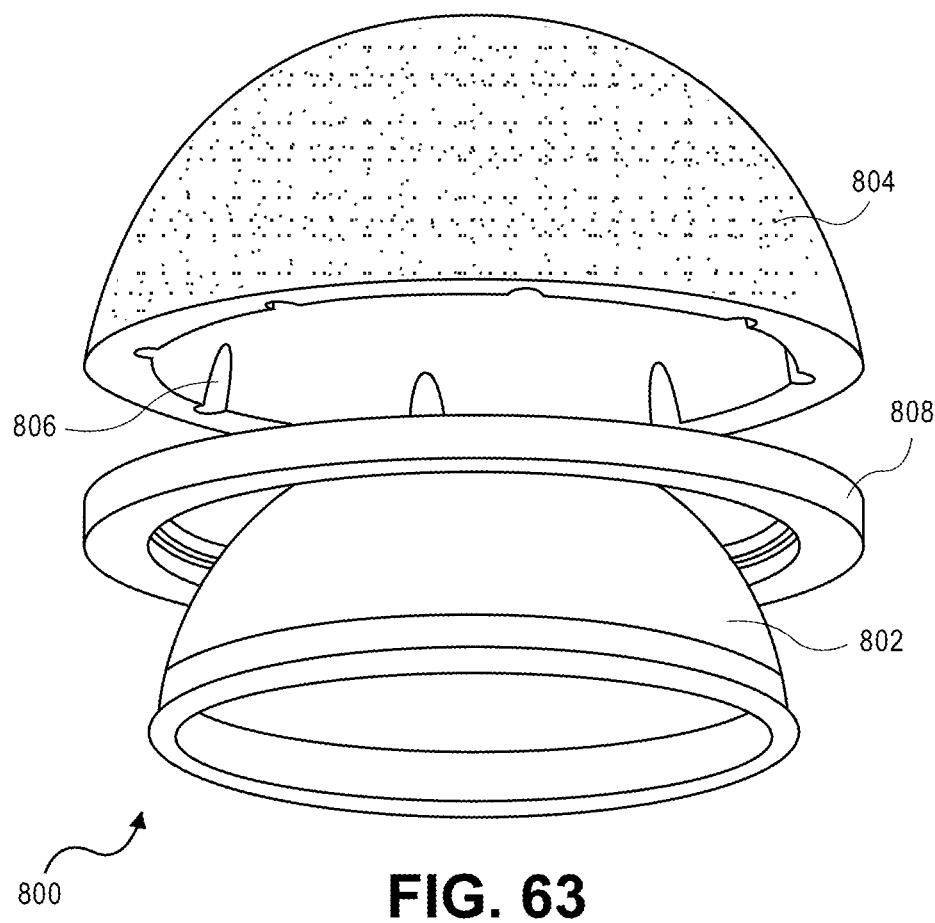
FIG. 63 shows another embodiment of a metal implant having a gradient polymer alloy bearing surface.

An implant according to the disclosure may be assembled before insertion into a joint region or two or more parts may be assembled intraoperatively while in the joint. FIG. 63 shows a metal implant and a gradient polymer liner that can be separately inserted into a joint. Metal cup 804 may be first placed in a joint, then gradient polymer liner 802 may be placed. Polymer liner 802 may be attached or adhered to metal cup 804 in any fashion. It may be held by chemical bonds or physical means. FIG. 63 shows grooves 806 for holding or flowing a material to aid in attaching a liner to a metal portion. The metal or the polymer liner may have features that change shape to aid in attachment, such as tabs. The metal cup and liner may be adhered using adhesive, cement (e.g. polymethylmethacrylate (PMMA)), epoxy, glue, or grout. FIG. 63 shows an optional ring to secure the liner to the metal. The ring may interlock or screw the liner to the metal. In one example, a liner can be removed and replaced with a new liner without removing the metal portion.

For a femoral device, a gradient IPN "cap" may be designed to fit on top of a metal femoral cap. A modular arrangement may allow a wider range of size interchangeability and tolerances in terms of the fit between a convex and concave joint surface. In addition, it may allow for various cup geometries for different pathologies. For example, it would allow for metal cups/backings with screw holes for additional fixation in the case of poor bone. It may also allow for a dysplasia cup and finned cups. A modular arrangement gives flexibility to adapt to patient needs and surgeon preference, which may be decided intra-operatively. The modularity may be enabled by mechanism. Modularity may be enabled by a locking mechanism, such as a taper, deforming tab, and a "screw-in" mechanisms. Typically, with modular systems on the market today, the liner (poly, ceramic, metal) is assembled to the metal cup as a last step. This allows the surgeon to perform a final trialing prior to final implantation. It also gives the surgeon the option to use a lipped liner for additional stability should he deem it necessary at time of surgery. Any of these mechanisms may also be used with a non-modular (e.g. preassembled) device. Modularity also provides the option of replacing just the bearing materials in the artificial joint for various reasons without disturbing the bone interfacing members.

Another aspect of the invention provides methods and implants for changing a shape of an implant. A metal, especially a porous metal, may have some ability to deform (e.g. bend, crimp, expand, fold, stretch, twist) or otherwise change a shape under an applied stress. A shape change may be transient. A metal may deform by bending one or more struts or regions along a metal meshwork.

In one example, an implant may cover an area greater than 180 degrees of a bone. For example, a hip implant for a femoral cap may encompass greater than 180 degrees, as shown in FIG. 62. The deformability of the porous metal and the polymer to which it is attached allows the entire cap to deform (e.g., open, stretch or otherwise change its spatial configuration or spatial conformation) to enable it to be placed over a spherical femoral head. A tool can be used to return the device to a different or preferred shape, such as to contact more of the femoral head or femoral neck surface. Metals with good shape memory properties would be useful in this particular embodiment.

An implant having a porous metal surface and a flexible or deformable polymer may change a shape. Any metal that can change a shape may be used. Any polymer that provides a biocompatible surface useful in a joint replacement may be used in an implant. A polymer on a surface may create a slippery, a soft, and/or a smooth surface. A polymer may be a lubricious polymer. In one example, an implant polymer is a gradient polymer alloy as described herein.

One aspect of the invention involves methods for inserting an orthopedic implant into a joint.

A shape of an implant may be changed for any reason. A change in shape may provide an implant with a smaller size to aid in implant insertion (e.g. for arthroscopic or minimally invasive surgery). A change in shape or size may allow an implant to fit into a joint region. For example, a shape may be changed to allow an implant to fit over a femoral head. A shape of an implant may be changed so that the implant conforms to at least a portion of a shape of a joint. For example, a portion of a joint may have an irregular surface and an implant shape may be changed to abut or fit a shape of the surface.

Figure 64:
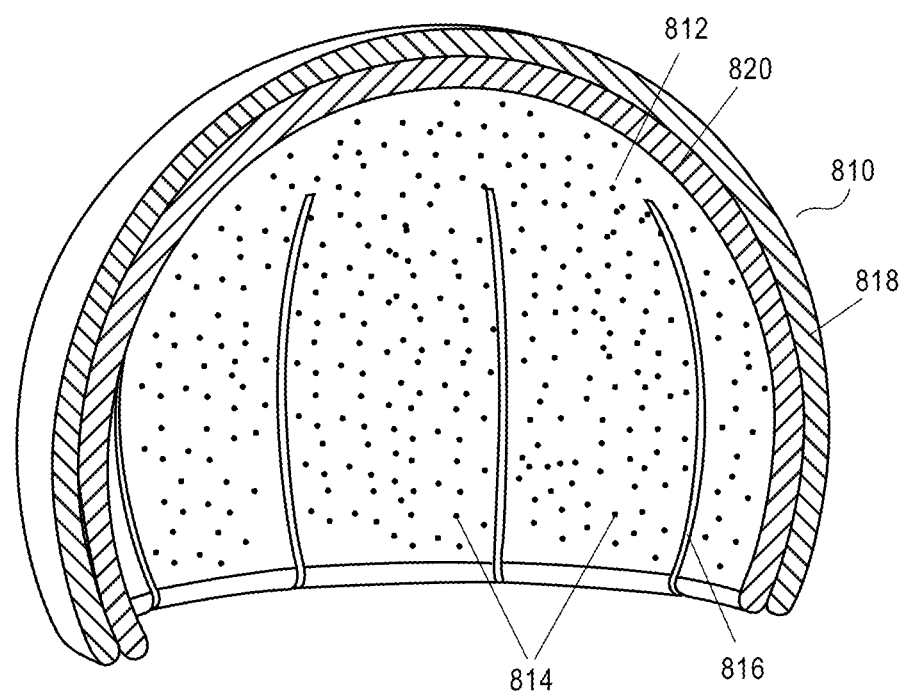
FIG. 64 shows a metal implant with expansion gaps and a deformable polymer for placement in a joint in a body.

FIG. 64 shows another embodiment of an orthopedic implant able to change a shape, e.g. to aid in insertion into a joint. FIG. 64 shows implant (cap) 810 with metal portion 812 attached to polymer 818. Polymer 818 may be any flexible or deformable biocompatible polymer useful for joint replacement. In one example, it is a gradient polymer as described herein. Metal portion or back 812 has two or more discontinuous segments (or leaves) 814. There may be lines of separation or gaps 816 between the segments to allow the implant to change shape. The lines of separation may run in a longitudinal direction anywhere from a few degrees from the opening (collar) to well beyond the equator. The lines may allow the device to "open" transiently in a radial direction (like a claw or petal on a flower). Individual segments may be deposited on or attached to the polymer. Metal may be laid down on the polymer, and then portions removed (e.g. by laser etching) to leave segments. In another embodiment, portions or segments may be hinged, connected, or otherwise attached at the north pole (like a clamshell) and may open as the implant stretches out while being lowered over the femoral head. The portions or segments may close after being lowered to surround the implant and femoral head. A metal may be sufficiently flexible and resilient, yet rigid enough to snap back into position after a transient deformation. In another embodiment, the metal segments or portions are mostly discontinuous, but retain some continuity through flexible connecting elements. The elements may be, for example, curves, zigzags, or springs.

Figure 65:
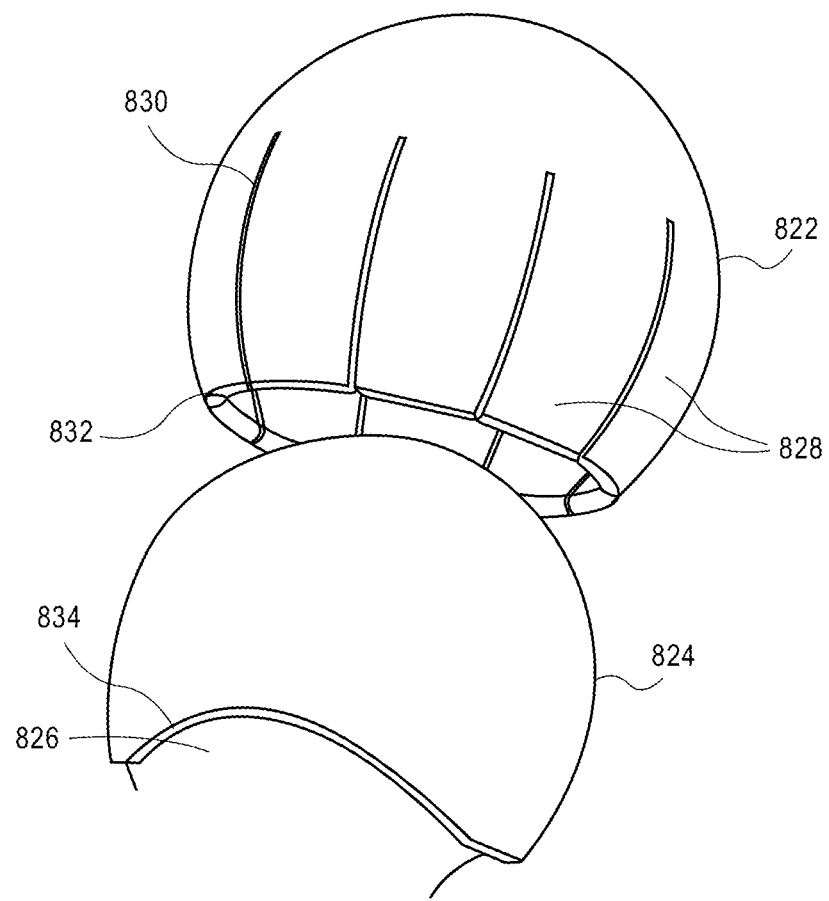
FIG. 65 shows an implant such as the one in FIG. 64 being placed over a femoral head.
Figure 66:
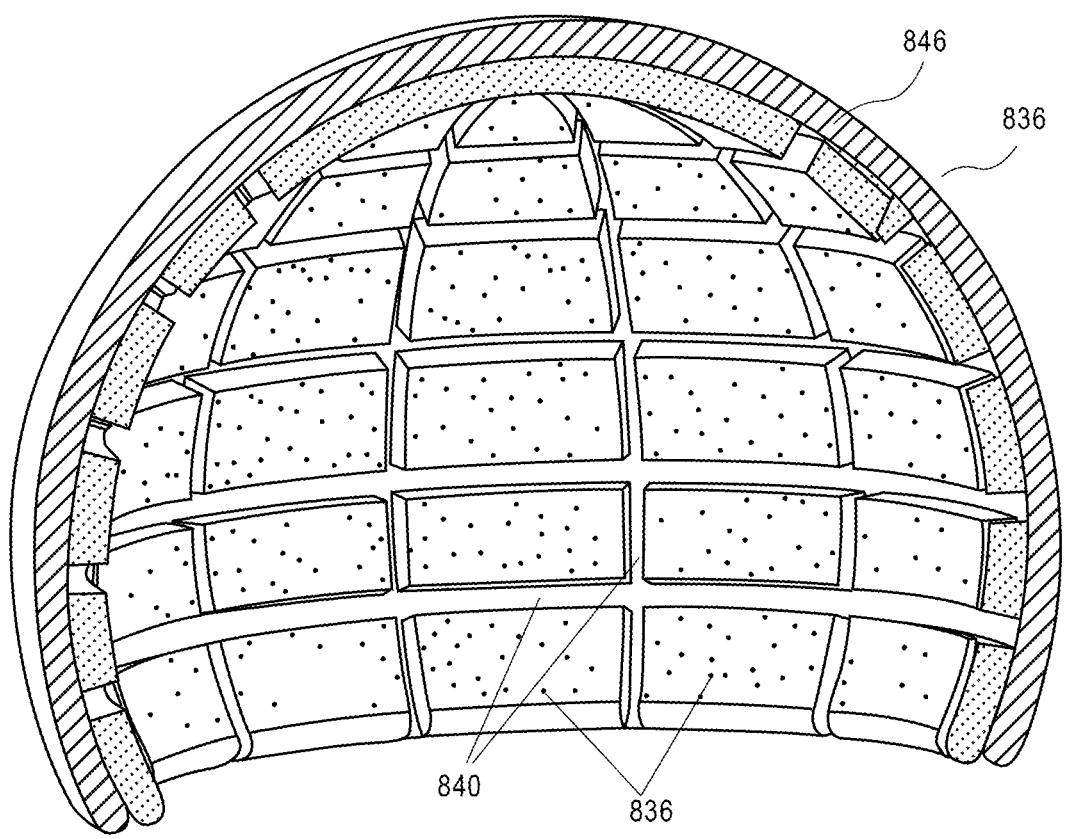
FIG. 66 shows an orthopedic implant with metal segments for placement in a joint.

FIG. 65 shows the metal portion of an orthopedic cap implant, like the one shown in FIG. 64, configured for placement on a femoral head. For simplicity, the polymer portion is not shown. Implant 822 has to fit over femoral head 824. In particular, the region of the implant near collar 832 as well as collar 832 need to pass over the large femoral head 824 and then rest on smaller edge of femoral head 834 and femoral neck 826. Lines of separation 830 between segments 828 in the implant along with a flexible metal allow the implant to expand for insertion. The metal may be sufficiently resilient to take a preferred shape after insertion, or may take a preferred shape after a treatment (e.g. heat) or application of a tool.

FIG. 65 shows another embodiment of an orthopedic implant able to change a shape. Segments 836 of metal separated by gaps 840 are embedded or otherwise attached or connected with flexible polymer 846. The segments (or elements) may be substantially solid, porous. The metallic elements may be arranged in a discontinuous fashion. The gaps may be strategically placed, with specific sizes and orientations, or they may be randomly placed. The entire device may as a whole flex and in turn, minimize the stress placed on each individual structure. The gradient polymer may be stretched or deformed (e.g. to change its spatial conformation or spatial configuration), while the individual metal components move relative to one another. The exact movement may depend on how the polymer is deformed and the orientation and structure of the metal segments. Metal-free gaps (or spaces) may be strategically placed. The gaps may be chosen to allow a predetermined location and direction for a metal to expand or collapse. Gaps and metal composition may be different for different purposes. In response to a stimulus, such as being stretched (e.g. by hand, heat, placement on a joint surface) the polymer stretches to accommodate to a new shape. After placement in the joint, the polymer may return to its original or a preferred shape and size. FIG. 65 shows that metal segments may separate radially from one another as the implant is brought down over a spherical femoral head, and stretched at the opening to clear the equator of the head. The figure depicts rectangular shaped segments, but the present invention can be comprised of segments of other shapes, including but not limited to circular (disc) shapes, squares, triangles, or any polyhedron with n-number of sides. The size and spacing between such segments can vary.

Figure 67:
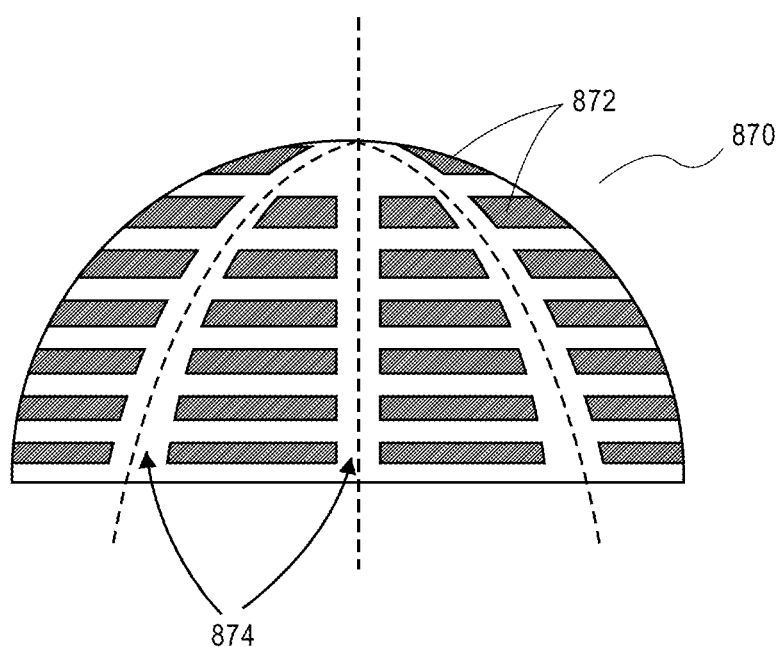
FIG. 67 shows another embodiment of an orthopedic implant with metal segments for placement in a joint.

FIG. 67 shows an acetabular component 870 with a segmented metal backing having a plurality of segments 872 attached to or embedded with a polymer member. Segments are discontinuous with slots or gaps 874 between segments to allow the implant to collapse, expand, or otherwise change its shape. The gaps in the figure are exaggerated to show how the polymer may stretch. The implant is able to flex and bend due to the gaps between the metal segments without putting undue stress or strain on the metal components themselves. The metal segments may be continuous or may have holes, pores, or slots. The implant or metal may transiently bend during placement in a body or in a joint. The metal may provide a bone contact surface for attaching to a bone. The metal may allow bone ingrowth.

In one aspect, a method of inserting an implant in a joint of a body may include inserting a polymer-metal implant into a joint space and changing a shape of the implant from a first shape to a second shape to conform to a shape of at least a portion of a bone forming the joint. The method may include returning the implant back to the first shape. The method may also include deforming the implant prior to the changing step from an original shape to a first shape. This may be useful, for example, to place the implant in the joint (e.g. through arthroscopic or minimally invasive surgery). For an implant configured to be placed on a femoral head of a hip joint, deforming may include expanding at least a portion of the implant to fit over the femoral head.

The various embodiments of the present invention are applicable to any joint in the body, including but not limited to the hand, feet, digits (of the hands and feet), ankle, intervertebral discs (cervical, thoracic, lumbar, or sacral), intervertebral facets, hip, knee, shoulder, and temporomandibular joint. The devices may be used with a, acromioclavicular joint, ankle joint, condyle, elbow joint, finger joint, glenoid, hip joint, intervertebral disc, intervertebral facet joint, labrum, meniscus, metacarpal joint, metatarsal joint, patella, tibial plateau, toe joint, temporomandibular joint, or wrist joint.

Any of the devices, features, materials, or methods described herein may be combined with any other devices, feature, material or method.

Figure 68:
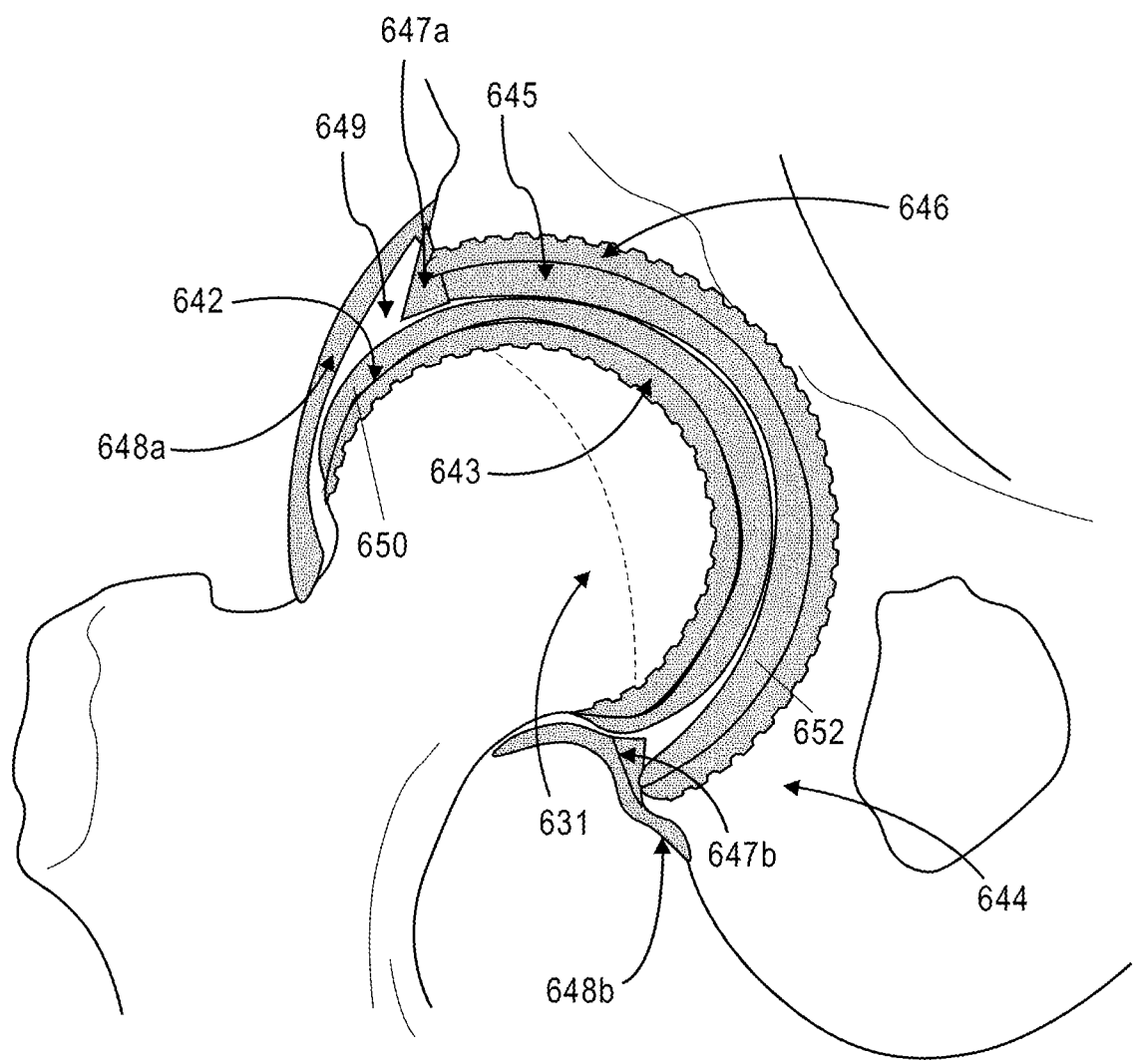
FIG. 68 shows a total cartilage replacement system, with cap-on-cup cartilage replacement implants, a synthetic joint capsule component, labral components, and lubricant fluid according to one aspect of the invention.

FIG. 68 shows a total hip cartilage and joint replacement system with gradient polymer metal alloy cap-on-cup implants according to one aspect of the disclosure. Both sides of the joint as well as labral and capsule components are replaced. The system may include femoral implant 650 and acetabular component 652. The bearing surfaces of the polymers on the two sides of the joint are configured to mate to provide a smooth, lubricious artificial joint interface. Lubricous IPN polymer 642 and lubricious IPN polymer 645 are respectively attached to metal bone interfacing members 646, 643 with porous metal backings which are in turn attached to femur 631 and acetabulum 644. The total replacement system may further include an artificial labral component shown in superior cross section 647a and inferior cross section 647b which may enclose lubricant 649. The system may also include an artificial capsule as shown in superior cross section 648a and inferior cross section 648b capsule components. A labral or capsule component may be made of any strong material with a smooth surface to provide support, stability, and/or lubriciousness to a joint. A labral or capsule component may be made from any of the IPNs or semi-IPNs described or referenced herein.

Figure 69:
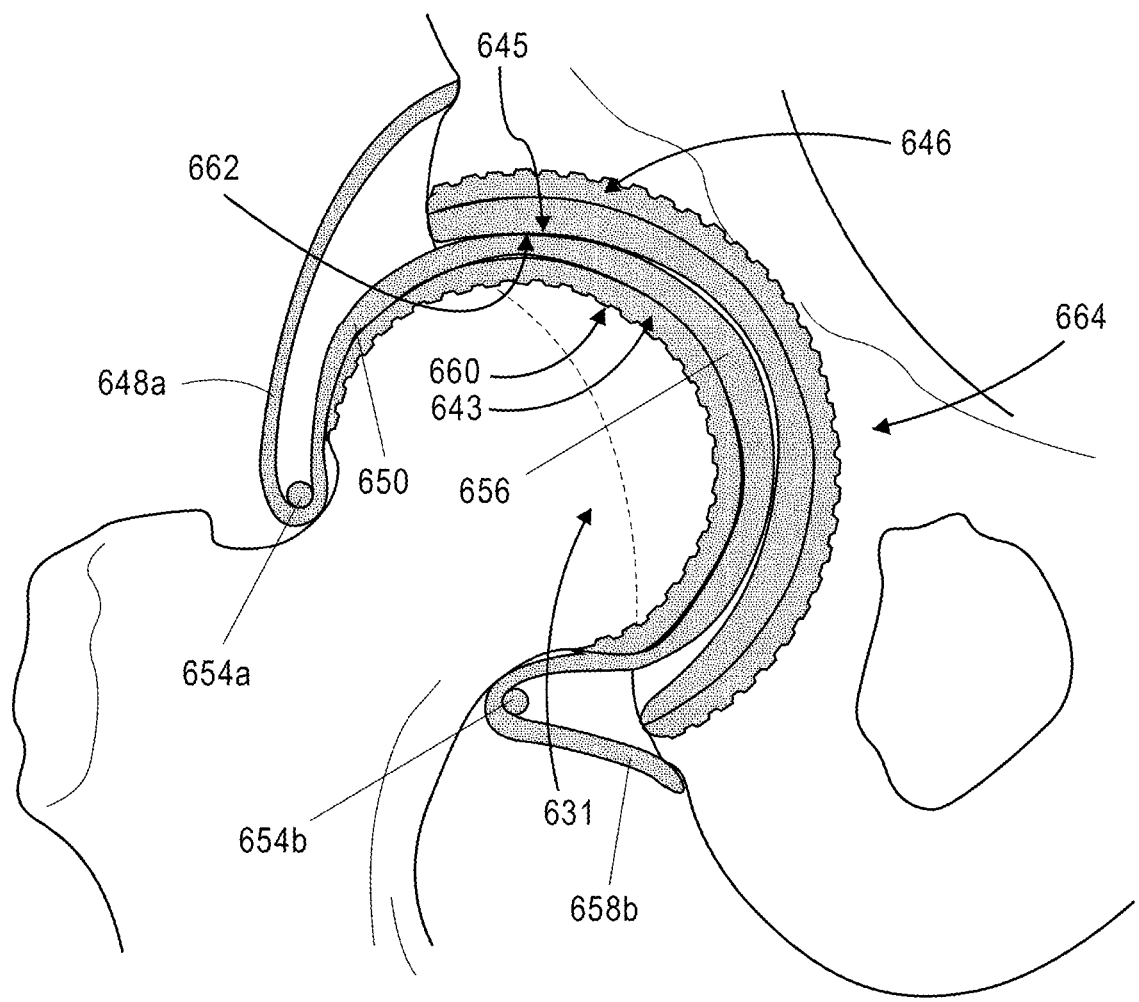
FIG. 69 shows an integrated joint and joint capsule replacement system according to one aspect of the invention.

FIG. 69 shows another embodiment of a hip total cartilage replacement system with an acetabular implant similar to the one described in FIG. 68 and with an integrated labral/femoral device. Femoral replacement implant 662 includes a femoral contacting portion and a labral replacement portion shown in superior cross section 648a and inferior cross section 658b continuous with the femoral contacting portion 650 and extending proximally toward the acetabular rim. The system may include an acetabular component. The bearing surfaces of the polymers on the femoral and acetabular side are configured to mate to provide a smooth, lubricious artificial joint interface. The devices may be attached to metal bone interfacing members 646, 643 with porous metal backings which are in turn attached to femur 631 and acetabulum 644. Features 660 may aid the implant in attaching to a bone. Features may be any structure that aid in placing or attaching an implant into a joint, such as cones, depressions, grooves, pegs, pillars, pins, and pyramids. An implant may have one feature or may have many (2-5, up to 10, up to 100, up to a 1000, or more) features. A feature(s) may be present on a bone contact surface of a metal or other bone interface member to aid in attaching an implant (e.g. a metal implant) to a bone. A feature(s) may be present on a surface or zone of a bone interface member that attaches to an attachment zone of an IPN or semi-IPN. The labral implant or portion of a labral implant may be fixed to bone through any means (e.g. screws, bone anchors, sutures, and/or welded polymer rivets). Superior 654a and inferior 654b collar sections are also shown in cross section. A collar may provide support or otherwise maintain a labral portion in a desired position. A collar may cinch over a labral portion. The ends of the labral portions may also (or instead) be continuous with an acetabular portion (not shown in this view).

Any of the implants described herein may be configured to correct large or small cartilage defects.

Figures 70A, 70B:
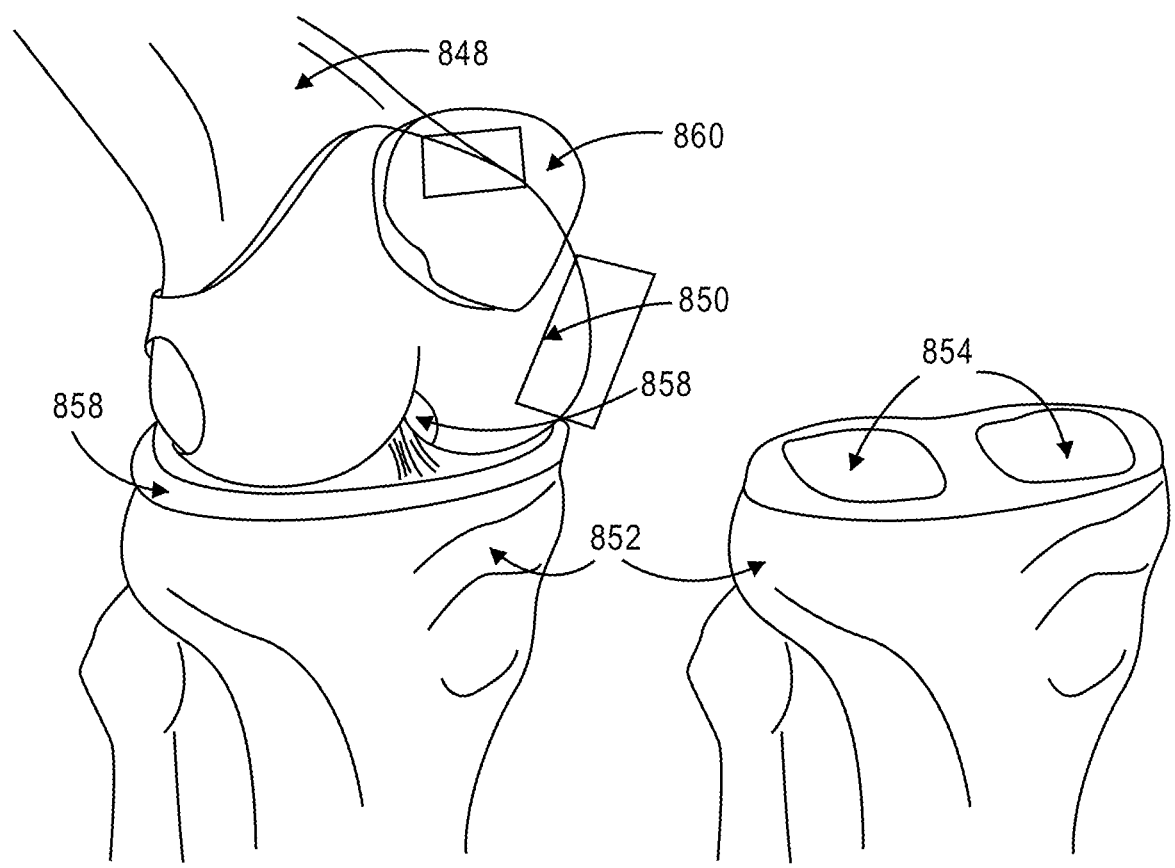
FIGS. 70 A-B show metal patches with gradient polymer alloy bearing surfaces in a knee joint.

FIGS. 70 A-B show metal-backed gradient polymer alloy used to correct both large and small cartilage defects. The knee has a distal femur 851 with a femoral condyle component 852 with space for the anterior and posterior cruciate ligaments 858. FIG. 70 also shows tibial plateau 852 with tibial implant 854 and meniscal implant 855. FIG. 70 also shows patella 860 with patellar implant 862. In this embodiment, the implants are made of polymer and metal components as described above, but shaped as patches. A patch-shaped implant of any size may be placed in any part of the knee joint needing repair.

Figure 71A:
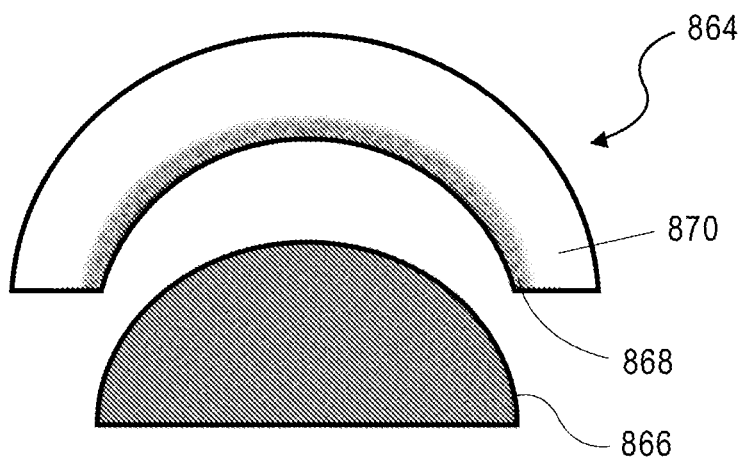
FIGS. 71A-C show metal caps, patches, and plugs with gradient polymer alloy bearing surfaces.
Figure 71B:
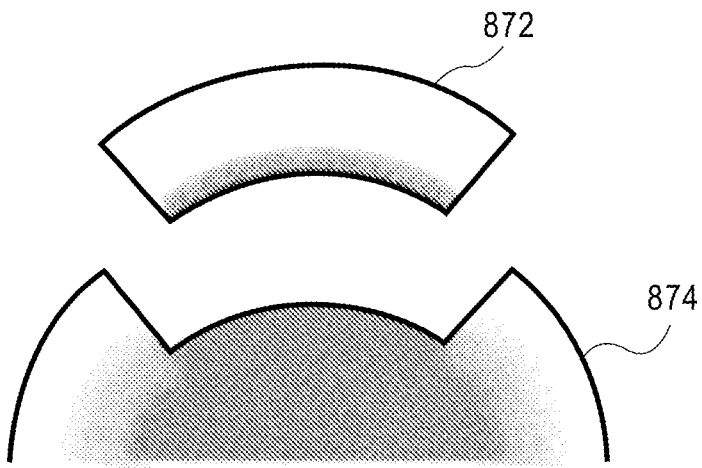
Figure 71C:
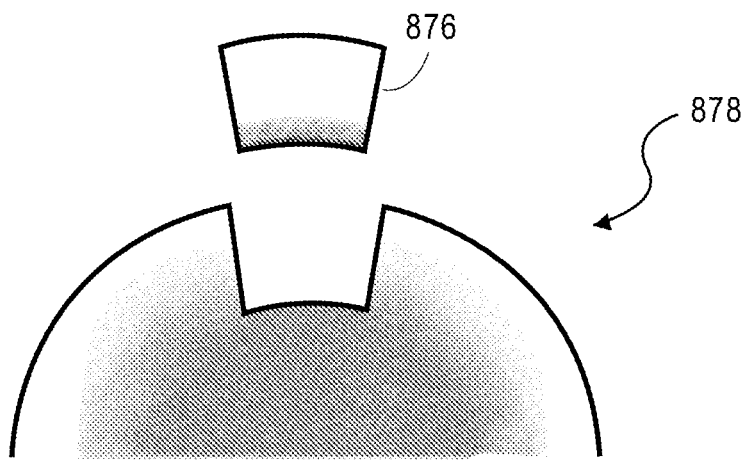

FIGS. 71A-C shows how caps, patches and plugs made from gradient polymer metal alloy with a hydrated surface 870 and a metal portion with a bone attachment surface 868 may be used. FIGS. 71 A-C depicts how cartilage defects can be addressed with the present invention by caps 864 replacing an entire surface of bone 866, patches 872, replacing a large, but subtotal area, or plugs 878, replacing a small, focal defect in the cartilage of a joint surface. Concave or flat geometries are also possible. For instance, a concave "cup" would be used to repair a concave joint such as the hip socket.

Another aspect of the invention provides variations of IPNs and semi-IPNs. The basic embodiment is the combination of a polyurethane, a polyelectrolyte polymer, water, and salts. One embodiment comprises the combination of a polyether urethane, the sodium salt of poly(acrylic acid), water, as well as other salts. The ratios between these components vary depending on the composition of polyurethane, initial concentration of acrylic acid monomer, and both the amount and type of crosslinking agents used.

One factor is the durometer of the polyurethane used, which typically ranges from about 80 A to 75D but can also be softer or harder than these, respectively. The durometer is usually determined by the ratio of hard-to-soft segment species in the polyurethane. A typical hard segment species used is methylene diphenyl diisocyanate (MDI), and a typical soft segment species used is poly(tetramethylene oxide) (PTMO). The ratio of MDI:PTMO in the polyurethane used can range from a predominance of soft segment constituents to a predominance of hard segment constituents. The exact ratio has a direct bearing on both the physical and mechanical properties of the polyurethane and its ability to be swollen by various monomers and/or solvents. In the present invention, a polyurethane with an intermediate durometer between 55 D and 75 D (i.e. 65D) yielded particularly excellent results in terms of equilibrium swelling of the material and mechanical properties. Other variations of polyurethane durometers can be used, such as 61 D, 63 D, or 67 D, which are expected to yield properties along the spectrum of those laid out by the 80 A, 55 D, 65 D, and 75 D polyurethanes described herein.

In the present invention, polyurethanes of varying durometers are swollen in a range of solution concentrations of acrylic acid monomers in water, along with a photoinitiator. A poly(acrylic acid) network is then formed by photoinitiated free radical polymerization and crosslinking of the acrylic acid monomers in the presence of the pre-existing polyurethane to form an interpenetrating polymer network of the two materials. The poly(acrylic acid) within the polyurethane is then neutralized in buffer solution to pH 7.4 and ionized and thus converted to sodium polyacrylate. Because this conversion takes place within the polyurethane matrix, the result is swelling of the IPN with additional water and salt (cations and anions) until a new equilibrium composition is reached between the polyurethane, sodium polyacrylate, water, and salts.

A second element of the present invention is the variation of the composition of this material across its thickness to form a gradient of hydration. This gradient is formed by controlling the amount of monomer that is allowed to penetrate the polyurethane matrix in a given plane prior to polymerization of the monomer to form the polyelectrolyte. The result is a material with differential swelling with water on one side versus the other. The ratio of polyurethane to polyelectrolyte varies as well, from one surface to the other, ranging from as high as 90% down to 0%.

The basic structure of this material mimics that seen in hyaline cartilage, where a tough structural matrix formed by organized collagen is interpenetrated by negatively charged proteoglycans that absorb water. Ions (namely sodium cations) play an important counterion role with the charged moieties on the proteoglycan molecules. It is the interplay between the proteoglycans, ions, water, and the surrounding collagen matrix that gives hyaline cartilage its unique load-bearing and low-friction properties. The present invention is a material that mimics the interplay between these key compositional structures, providing a structural matrix comprising polyurethane (which contains both ordered and amorphous domains), negatively charged sodium polyacrylate, ions, and water. As is described herein, variations on this combination of a polyurethane and polyelectrolyte can differ in terms of the type of polyurethane (e.g. polyether urethane, polycarbonate urethane, polyurethane urea, or a silicone-based derivative of these), polyelectrolyte (e.g. any homopolymer or copolymer system containing at least one of a carboxylic acid and/or a sulfonic acid functional group), as well as crosslinking agent or initiator (e.g. light-activated, chemical, or thermal). For the purposes of this disclosure, a polyelectrolyte is defined as a polymer or polymer network that bears a net negative charge. The polyelectrolyte network may have neutral (uncharged or ionizable) monomers and/or even positively charged monomers copolymerized with the charged or ionizable monomers, effectively forming a copolymer network. For instance, acrylic acid, acrylamido methyl propane sulfonic acid, hydroxyethyl methacrylate, and acrylamide can be copolymerized in various ratios relative to each other and still yield a polymer network with a net negative charge. The concentrations or identities of any of these elements can vary without deviating from the essence of this invention. For example, any of the monomers or combinations of monomers listed in U.S. 2008/0269370, U.S. 2009/0088846 A1, and/or herein can be used (e.g. dimethylacrylamide, acrylamide, NIPAAm, methyl acrylate, methyl methacrylate, hydroxyethyl acrylate/methacrylate, and any vinyl-based monomer containing sulfonic acid groups (e.g. acrylamido methyl propane sulfonic acid, vinyl sulfonic acid, 3-sulfopropyl acrylate (or methacrylate), 2-methyl-2-propene-1-sulfonic acid sodium salt, or any monomers in which sulfonic acid is conjugated (allyl ethers, acrylate/methacrylates, vinyl groups, or acrylamides). The monomer can also include any monomers containing carboxylic acid groups conjugated to allyl ethers, acrylate/methacrylates, vinyl groups, or acrylamides. In addition, the monomers can be used in combination, such as both carboxyl acid and sulfonic acid containing monomers, to create a carboxylate/sulfonate copolymer. The pendant functional groups on polymers resulting from these monomers and monomer combinations can be subject to subsequent chemical reactions to yield other functionalities to the final polymer. Other ionizable monomers include ones that contain negatively charged carboxylic acid or sulfonic acid groups, such as methacrylic acid, 2-acrylamido-2-methylpropanesulfonic acid, sulfopropyl methacrylate (or acrylate), vinyl sulfonic acid, or vinyl-conjugated versions of hyaluronic acid, heparin sulfate, and chondroitin sulfate, as well as derivatives, or combinations thereof.

Sulfonic acid functional groups may be incorporated into an already formed IPN or semi-IPN (including a gradient IPN or semi-IPN). The general principle is to replace the carboxylic acid groups present on a poly(acrylic acid) in an IPN with sulfonic acid-containing functional groups. This is an alternative way to bring sulfonic acid into an IPN, whereas a more direct way is to polymerize or co-polymerize sulfonic acid-containing monomers in a 2nd network formation step. The end result is the same (an IPN with a hydrophobic (e.g. polyurethane) first network and a copolymer containing of carboxylic acid groups and sulfonic acid groups in the second network). This may have advantages in some cases of possibly increasing the yield (percentage) of sulfonic acid in the second network, and could also make possible the formation of a gradient of sulfonation within the second network.

Any process may be used to incorporate sulfonic acid groups into a second network. One process to incorporate sulfonic acid groups into the second network of a polyurethane/poly(acrylic acid) IPN is as follows. To 200 mL 5 mM 1-Ethyl-3-(3-dimethylaminopropyl) carbodiimide (EDC) solution is added a 1 g slab of an IPN of polyurethane and poly(acrylic acid) and the pH of the solution is titrated to 5.5. After soaking for an hour, 1 g of taurine (aminoethanesulfonic acid) is added into the solution and incubated at 37 degrees C. for 6 hours. After the reaction, the IPN is washed repeatedly to remove the catalyst and residual taurine. Other water-soluble carbodiimides can be used as the catalyst in this reaction instead of EDC, for example, 1-cyclohexyl-3-[2-morpholinoethyl]carbodiimide. Also, other sulfonic acid containing chemicals can be used to attain sulfonic acid functionality on the second network, including ones that result in the formation of 2-acrylamido-2-methyl propane sulfonic acid. The final amount of sulfonic acid addition to the 2nd network can be varied through the time, temperature, molar ratio of reactants, and concentration and identity of catalyst, to attain anywhere from a very small percentage (e.g. 0.01% sulfonation) of the second network to a very high percentage (50% or greater). Examples of IPNs produced using this process include a semi-IPN of polyurethane/poly(acrylic acid-co-acrylamido ethane sulfonic acid) as well as polyurethane/poly(acrylic acid-co-2-acrylamido-2-methyl propane sulfonic acid). IPNs, gradient IPNs, and semi-IPNs containing sulfonic acid-containing second networks may also be created using the above process.

The solution (e.g. aqueous buffer) in which these materials are immersed and swollen may also differ without deviating from the essence of this invention.

FIGS. 72A-F is a schematic of equilibrium swelling that illustrates the structure of an IPN or semi-IPN according to one aspect of the disclosure. FIGS. 72A and 72C show a first "structural" network and an ionizable network, respectively, in schematic form. The former is described as a structural network in this case because it is not ionizable and does not take on a negative charge in aqueous solution, and therefore does not swell to any significant extent in response to the presence of water, a salt, or other ions (e.g., hydrogen or hydroxide). FIG. 72B shows an IPN (or semi-IPN) of the structural network and ionizable network in schematic form. FIGS. 72D-F show the structural network, the IPN (or semi-IPN), and the ionizable network after immersion in an aqueous solution such as buffered saline or a body fluid. The immersion process (followed by equilibrium swelling) is represented by the down arrow. A structural network, such as polyurethane, retains its shape 828 after treatment with water. An ionizable network, such as poly(acrylic acid), assumes a neutralized (negatively charged) form under such conditions. It is the carboxylic acid functional groups in the poly(acrylic acid) that become negatively charged (or ionized).

In other embodiments, the sulfonic acid functional groups may be present either alone or in combination with the carboxylic acid groups, and take on a negatively charged (ionized) state. The ionizable network takes on a fixed (negative) charge (838) and swells (compare 836 with 826) through the attraction of positive counterions (namely sodium) and water, as well as other ions that follow the water. When these two network elements are combined in an interpenetrating polymer network arrangement (FIGS. 72B, E), the swelling of the ionizable network 824, 832 is resisted by structural network 822, 830, yielding a material with a new equilibrium swelling point. The IPN or semi-IPN therefore swells to a lesser extent than does the ionizable network alone due to the presence of the structural network. Moreover, because of the presence of the ionizable network, the IPN or semi-IPN also contains fixed charge (834). The presence of fixed charge in a hydrated network may be significant because it creates a high degree of polarity in the system, and attracts sodium counterions as well as a significant amount of water into the system, which is the basis for the swelling behavior. It is well known that natural cartilage (including meniscal or labral cartilage) contains fixed charge, and that its swelling, frictional, and mechanical properties are all largely dependent on the presence of fixed charge within its matrix. The fixed charge in natural cartilage and meniscus is also derived from a combination of carboxylic acid and sulfonic acid functional groups present on the glycosaminoglycan macromolecules that interpenetrate a collagen matrix. The present invention emulates the structure-function relationships exhibited by natural cartilage and meniscal/labral tissue by combining a tough structural matrix like polyurethane (that behaves similarly to the collagen in the native tissue) with an ionizable network of synthetic polyelectrolytes (that contain carboxylic acid and/or sulfonic acid groups) that contain fixed charge and attract counterions and water. In this invention, the equilibrium swelling of the two polymer system typically ranges from about 3% water to up to 80% water, and more commonly about 25% to about 80% and attain a simultaneous combination of properties such as water content, stiffness, coefficient of friction, permeability, failure strain, and tear strength that are difficult to attain with conventional polymers and homopolymer hydrogels.

FIG. 73 shows a schematic of the polyurethane-polyelectrolyte system described in the present disclosure. Polyelectrolyte polymer 846 (with negative charges 848) course through the amorphous phase of the polyurethane 842 that is in turn held together by the ordered phase of hard segments 844.

FIGS. 74 A-B shows a schematic of the gradient polyurethane-polyelectrolyte system described in the present disclosure. The material shows a stiffness, hydration, and material gradient from one side 850 to the other side 852 of a composition. Polyelectrolyte polymer 860 (with negative charges 854) course through the amorphous phase of polyurethane 856 that is in turn held together by the ordered phase of hard segments 858. On one side 852 of the material, only polyurethane is present, whereas the relative amount of polyelectrolyte increases and achieves a maximum on the opposing side 850 of the material. Side 852 is therefore stiffer (and therefore provides a better bone or bone attachment element interface), and side 850 is more lubricious (and therefore provides a better joint bearing surface).

Figure 76:
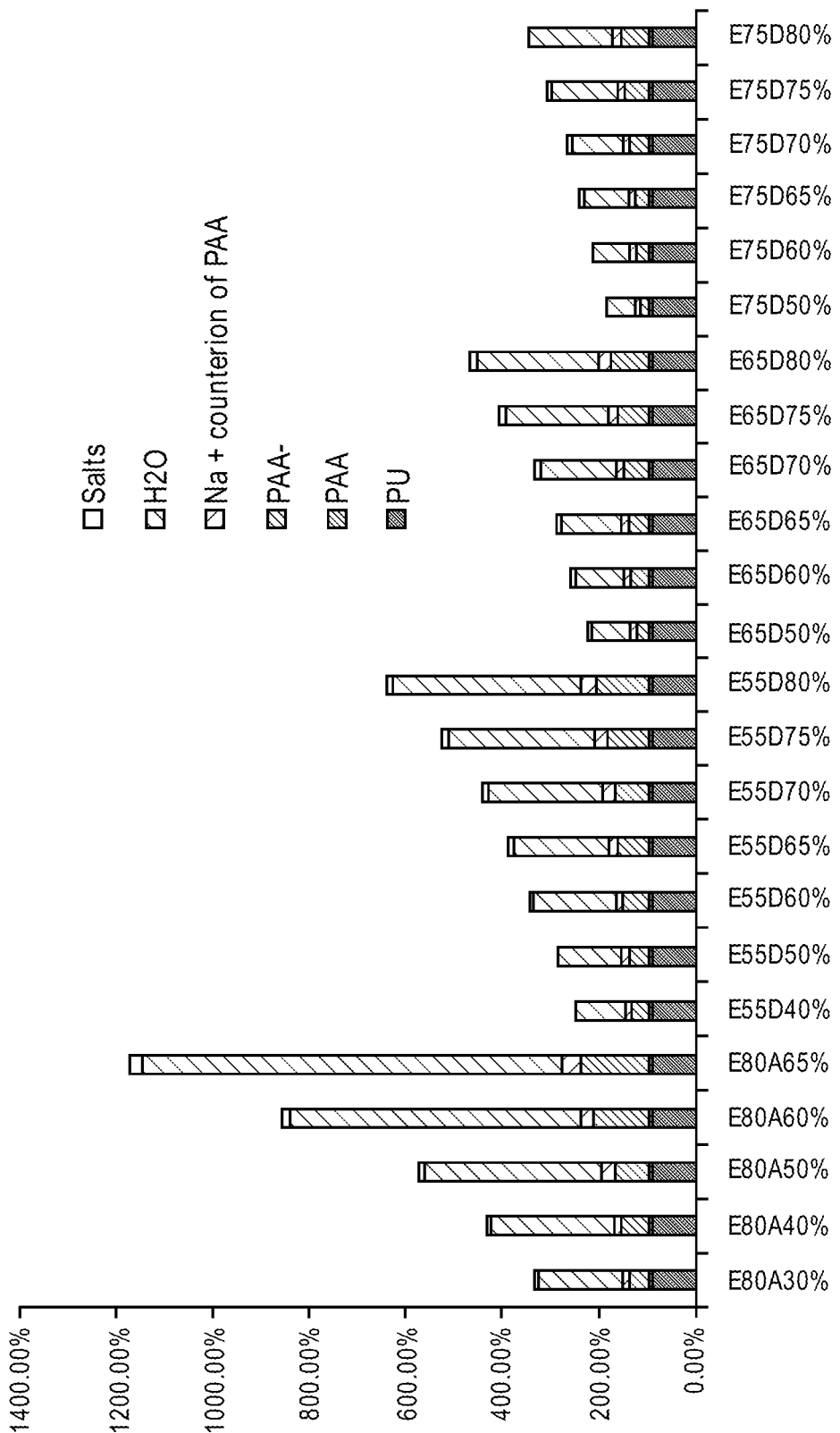
FIG. 76 is a graphical representation of the data shown in FIG. 75.

FIGS. 75 and 76 shows various polyurethane-polyelectrolyte systems produced by combining polyether urethane (Elasthane®) polymers with poly(acrylic acid), water, and salts. FIG. 76 shows a graphical representation of the data shown in FIG. 75. The nomenclature used here refers to the type of polyurethane, the durometer of the polyurethane, and the percentage acrylic acid monomers used prior to polymerization. For instance, "E80 A30%" means that an Elasthane® polyurethane of durometer 80 A was swollen in 30% acrylic acid in water. The Y-axis in this case represents the percent volumetric expansion at equilibrium swelling that the polyurethane underwent relative to its original volume. The expansion of the polyurethane is caused by the addition of various species into the system, including water, poly(acrylic acid) (PAA) in both the neutral and charged (PAA) state, the sodium ($Na^+$) counterion of PAA, polyurethane (PU), water (H$_2$O), and salts. Any of these combinations would be suitable to practice the inventions described herein.

Figure 78:
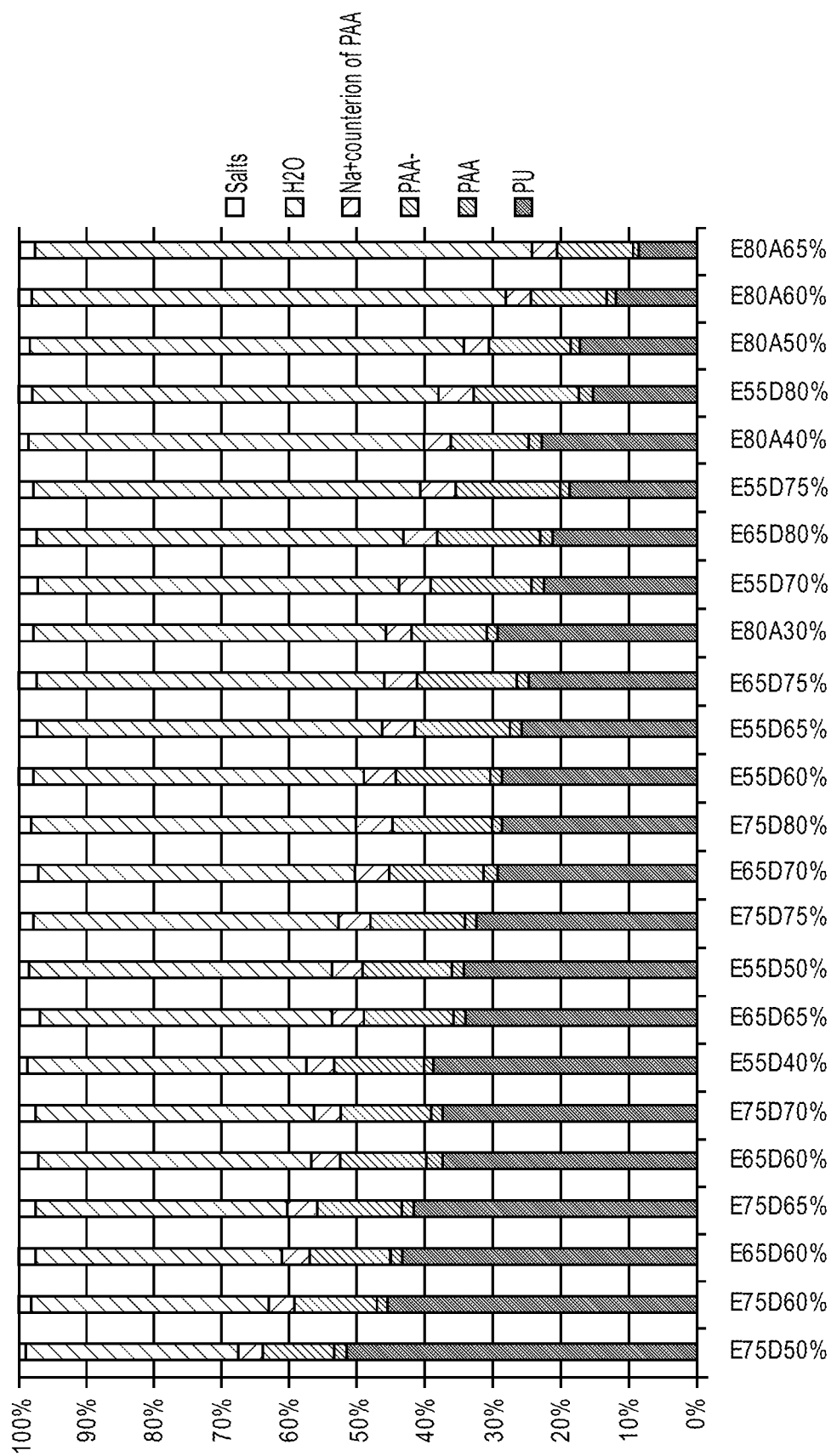
FIG. 78 is a graphical representation of the data shown in FIG. 77.

FIGS. 77 and 78 show an array of polyurethane-polyelectrolyte systems produced, by combining polyether urethane (Elasthane®) polymers with poly(acrylic acid), water, and salts. FIG. 78 shows a graphical representation of the data shown in FIG. 77. The nomenclature used here refers to the type of polyurethane, the durometer of the polyurethane, and the percentage acrylic acid monomers used prior to polymerization. For instance, "E80 A30%" means that an Elasthane® polyurethane of durometer 80 A was swollen in 30% acrylic acid in water. In this plot, the Y-axis represents the contribution, in percent, of each of the major elements in the system, including water, poly(acrylic acid) (PAA) in both the neutral and charged (PAA) state, the sodium (Na$^+$) counterion of PAA, polyurethane (PU), water (H$_2$O), and salts. Any of these combinations would be suitable to practice the inventions described herein. In one example, a composition of matter may have about 4% to about 90% w/w polyurethane, about 1% to about 40% w/w electrolyte of polyacrylic acid, and about 3% to about 80% water when analyzed at physiological pH (7.4) at 37° C. in a 0.9% aqueous salt solution. A composition may further include about 0.3% to about 13% sodium counterion of polyacrylic acid. In one example, the concentration of polyurethane in the composition may be from about 8% to about 55%. In another example, the concentration in the composition of an electrolyte of polyacrylic acid may be from about 9% to about 22%. In another example, the concentration in the composition of water may be from about 25% to about 80%. A composition may further contain about 0.3% to about 13% sodium counterion of polyacrylic acid.

Figure 79:
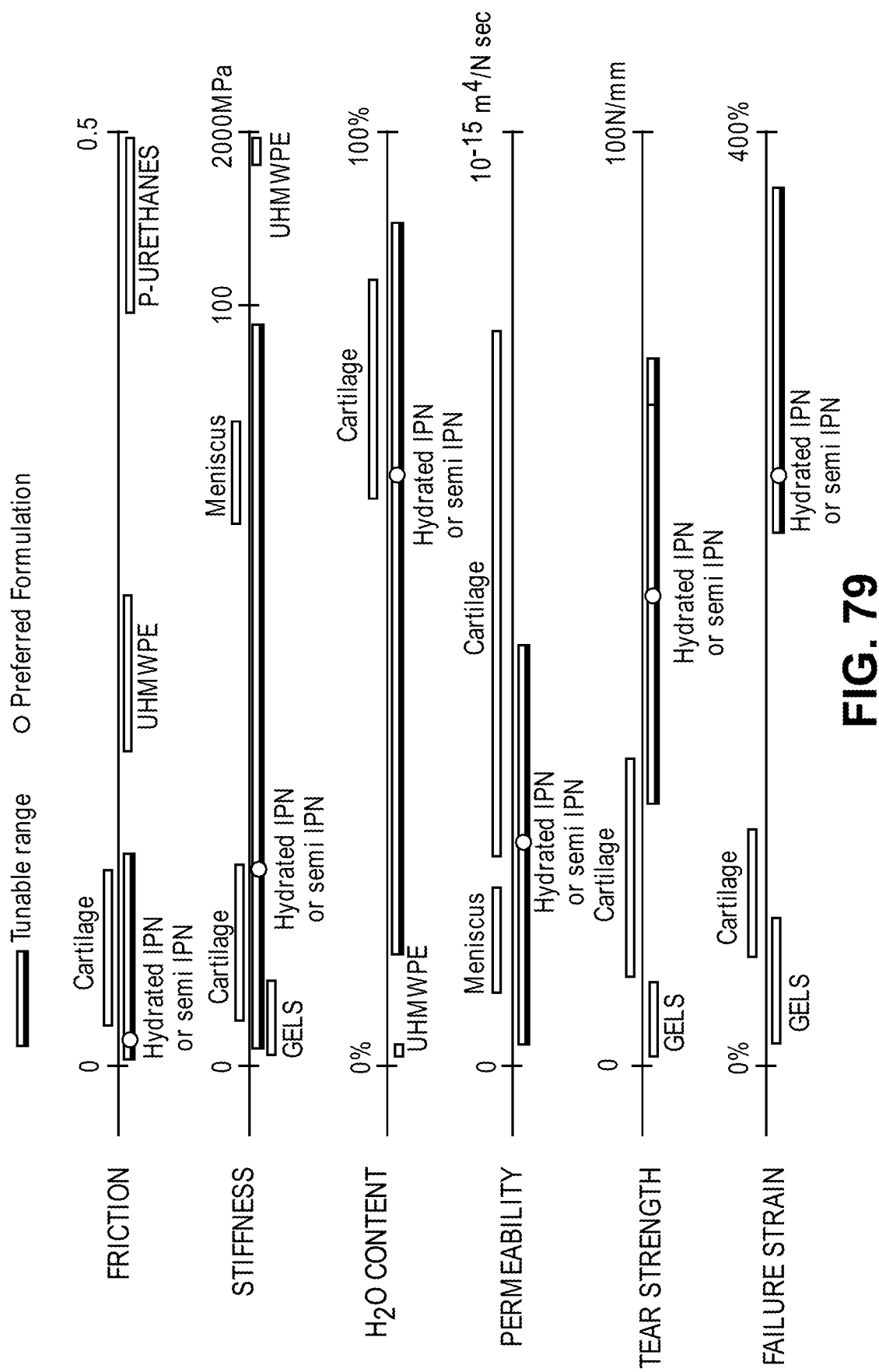
FIG. 79 shows characteristics of a gradient polymer such as those described in FIGS. 74-78 according to one aspect of the invention.

FIG. 79 shows material and mechanical properties of IPNS and semi-IPNS according to one aspect of the disclosure. FIG. 79 compares the range of properties exhibited by an IPN or semi-IPN according to the current disclosure in the hydrated state compared to the range of properties that have been described for natural cartilage, as well as commercially available polymers that are used in orthopaedic applications today, namely UHMWPE, polyurethanes alone, and hydrogel homopolymer networks. The open circles show material properties for a particular material.

In terms of friction (coefficient of friction (COF)), the hydrated IPN or semi-IPN overlaps with the range of values that have been published in the literature for natural hyaline cartilage. In contrast, the COF values of UHMWPE are higher, and those of polyurethanes alone are even higher, and neither overlap with the ranges known for cartilage.

In terms of stiffness (modulus), the hydrated IPN or semi-IPN can be synthesized to attain a wide range of values that overlap with the values that have been elucidated for natural hyaline cartilage ("cartilage") as well as those of the meniscus. In contrast, the stiffness of UHMWPE falls well above the range values known for either hyaline cartilage or meniscus. The stiffness of conventional homopolymer hydrogels ("GELS") are known to overlap to some degree with that of hyaline cartilage, but are limited in their upper range and generally speaking are not able to attain the stiffness values of the meniscus.

In terms of water (H$_2$O) content, the hydrated IPN or semi-IPN is able to obtain wide range of values that overlap with hyaline cartilage but also can attain higher and lower values as well. In contrast UHMWPE absorbs little to no water.

In terms of permeability (hydraulic permeability), the hydrated IPN or semi-IPN can achieve values that overlap with both the meniscus and hyaline cartilage. Generally speaking, the permeability of hyaline cartilage is lower the healthier the tissue is, and vice versa. Therefore, the hydrated IPN and semi-IPN is able to capture the permeability values of hyaline cartilage in its "healthy" spectrum.

In terms of tear strength, the hydrated IPN or semi-IPN can attain values that overlap or exceed the values known for that of hyaline cartilage. This is in contrast to most homopolymer hydrogel networks, which tend to have tear strength values below those known for hyaline cartilage.

In terms of failure strain (failure tensile strain), the hydrated IPN or semi-IPN according to the present invention is able to attain values that exceed those of either hyaline cartilage or most homopolymer hydrogel networks. This may be a consequence of the intrinsic extensibility of the first network material used, which is able to retain its capacity to be strained in spite of being swollen with water.

Other modifications will be apparent to those skilled in the art. As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. An orthopedic implant comprising:
a water swellable IPN or semi-IPN member having a bearing surface and a hydrophobic surface, the water swellable IPN or semi-IPN member comprising a hydrophobic thermoset or thermoplastic polymer first network and an ionic polymer second network configured to exhibit a compositional gradient between the bearing surface and the hydrophobic surface, wherein the hydrophobic surface is configured to attach to bone and comprises the hydrophobic first network and not the ionic polymer second network.

2. The orthopedic implant of claim 1, wherein the compositional gradient forms a stiffness gradient.

3. The orthopedic implant of claim 1, wherein the hydrophobic thermoset or thermoplastic polymer first network comprises polyurethane.

4. The orthopedic implant of claim 1, wherein the implant has a shape selected from the group consisting of a cap, a cup, a plug, a mushroom, a patch, a stem, a flat sheet, a pin, and a disc.

5. The orthopedic implant of claim 1 adapted to fit a shoulder joint, a finger joint, a hand joint, an ankle joint, a foot joint, a toe joint, a knee medial compartment joint, a patellofemoral joint, a total knee joint, a knee meniscus, a femoral joint, an acetabular joint, a labral joint, an elbow joint, an intervertebral facet, a vertebral joint, a condyle, tibial plateau, meniscus, labrum, or a glenoid.

6. The orthopedic implant of claim 1, further comprising a bonding agent adapted to attach said orthopedic implant to bone.

7. The orthopedic implant of claim 6, wherein the bonding agent is an adhesive, a cement, or a glue.

8. The orthopedic implant of claim 7, wherein the bonding agent is a light-curable adhesive.

9. The orthopedic implant of claim 1, further comprising a surface material bonded to the hydrophobic surface.

10. The orthopedic implant of claim 9, wherein the surface material is a metal, a glass, a plastic, a bone, or a synthetic bone.

11. An orthopedic implant comprising:

a water swellable IPN or semi-IPN member comprising a first portion, a second portion, a bearing surface, and a hydrophobic surface;

wherein the first portion includes an ionic polymer second network dispersed within a polyurethane first network, the ionic polymer second network exhibiting a compositional gradient within the polyurethane first network and decreases from the bearing surface towards the hydrophobic surface; and wherein the second portion comprises the polyurethane first network and not the ionic polymer second network.

12. The orthopedic implant of claim 11, wherein the compositional gradient forms a stiffness gradient.

13. The orthopedic implant of claim 11 wherein the implant has a shape selected from the group consisting of a cap, a cup, a plug, a mushroom, a patch, a stem, a flat sheet, a pin, and a disc.

14. The orthopedic implant of claim 11 adapted to fit a shoulder joint, a finger joint, a hand joint, an ankle joint, a foot joint, a toe joint, a knee medial compartment joint, a patellofemoral joint, a total knee joint, a knee meniscus, a femoral joint, an acetabular joint, a labral joint, an elbow joint, an intervertebral facet, a vertebral joint, a condyle, tibial plateau, meniscus, labrum, or a glenoid.

15. The orthopedic implant of claim 11, further comprising a bonding agent adapted to attach said orthopedic implant to bone.

16. The orthopedic implant of claim 15, wherein the bonding agent is an adhesive, a cement, or a glue.

17. The orthopedic implant of claim 16, wherein the bonding agent is a light-curable adhesive.

18. The orthopedic implant of claim 11, further comprising a surface material bonded to the hydrophobic surface.

19. The orthopedic implant of claim 18, wherein the surface material is a metal, a glass, a plastic, a bone, or a synthetic bone.

* * * * *